(12) United States Patent
Maharbiz et al.

(10) Patent No.: US 11,786,124 B2
(45) Date of Patent: Oct. 17, 2023

(54) IMPLANTS USING ULTRASONIC BACKSCATTER FOR RADIATION DETECTION AND ONCOLOGY

(71) Applicant: The Regents of the University of California, Oakland, CA (US)

(72) Inventors: Michel M. Maharbiz, El Cerrito, CA (US); Jose M. Carmena, Berkeley, CA (US); Mekhail Anwar, San Francisco, CA (US); Kristofer S. J. Pister, Oakland, CA (US); Stefanie V. Garcia, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1226 days.

(21) Appl. No.: 16/313,858

(22) PCT Filed: Jul. 7, 2017

(86) PCT No.: PCT/US2017/041260
§ 371 (c)(1),
(2) Date: Dec. 27, 2018

(87) PCT Pub. No.: WO2018/009908
PCT Pub. Date: Jan. 11, 2018

(65) Prior Publication Data
US 2019/0150881 A1 May 23, 2019

Related U.S. Application Data

(60) Provisional application No. 62/359,672, filed on Jul. 7, 2016.

(51) Int. Cl.
*A61B 5/00* (2006.01)
*A61B 6/00* (2006.01)
(Continued)

(52) U.S. Cl.
CPC ............ *A61B 5/0031* (2013.01); *A61B 5/076* (2013.01); *A61B 5/279* (2021.01); *A61B 5/686* (2013.01);
(Continued)

(58) Field of Classification Search
CPC ....... A61B 6/425; A61B 5/0031; A61B 5/686; A61B 6/4258; A61B 8/0808; A61B 8/085; A61B 8/0875; A61B 8/48
See application file for complete search history.

(56) References Cited

U.S. PATENT DOCUMENTS 2,830,274 A 4/1958 Rosen et al.
5,279,292 A 1/1994 Baumann et al.
(Continued)

FOREIGN PATENT DOCUMENTS

EP 2515996 A2 10/2012
EP 2355893 B1 12/2013
(Continued)

OTHER PUBLICATIONS

U.S. Office Action dated Jan. 10, 2018 issued in U.S. Appl. No. 15/702,301.
(Continued)

*Primary Examiner* — Dixomara Vargas
(74) *Attorney, Agent, or Firm* — Tom Hunter; Weaver Austin Villeneuve & Sampson LLP

(57) ABSTRACT

Described herein is an implantable device comprising a radiation-sensitive element (such as a transistor) configured to modulate a current as a function of radiation exposure to the transistor; and an ultrasonic device comprising an ultrasonic transducer configured to emit an ultrasonic backscatter that encodes the radiation exposure to the transistor. Further described herein is an implantable device comprising a radiation-sensitive element (such as a diode) configured to
(Continued)

generate an electrical signal upon encountering radiation; an integrated circuit configured to receive the electrical signal and modulate a current based on the received electrical signal; and an ultrasonic transducer configured to emit an ultrasonic backscatter based on the modulated current encoding information relating to the encountered radiation. Further described are systems including one or more implantable devices and an interrogator comprising one or more ultrasonic transducers configured to transmit ultrasonic waves to the one or more implantable devices or receive ultrasonic backscatter from the one or more implantable devices. Also describe are computer systems for operating implantable devices, methods of detecting radiation, methods of treating a solid cancer in a subject, and methods of monitoring a subject for recurrence of a solid cancer.

18 Claims, 30 Drawing Sheets

(51) Int. Cl.

| | | |
|---|---|---|
| *A61N 1/378* | (2006.01) | |
| *A61B 8/08* | (2006.01) | |
| *A61B 5/07* | (2006.01) | |
| *A61N 1/36* | (2006.01) | |
| *A61N 1/372* | (2006.01) | |
| *A61B 5/279* | (2021.01) | |
| *B06B 1/06* | (2006.01) | |
| *G01N 27/327* | (2006.01) | |
| *A61M 39/02* | (2006.01) | |
| *A61N 1/05* | (2006.01) | |
| *A61N 5/10* | (2006.01) | |
| *A61N 7/00* | (2006.01) | |

(52) U.S. Cl.
CPC ............ *A61B 6/4258* (2013.01); *A61B 8/085* (2013.01); *A61B 8/0808* (2013.01); *A61B 8/0875* (2013.01); *A61B 8/48* (2013.01); *A61N 1/3605* (2013.01); *A61N 1/3787* (2013.01); *A61N 1/37205* (2013.01); *B06B 1/06* (2013.01); *G01N 27/327* (2013.01); *A61B 2505/05* (2013.01); *A61B 2560/0219* (2013.01); *A61B 2562/028* (2013.01); *A61B 2562/12* (2013.01); *A61M 39/0208* (2013.01); *A61M 2205/04* (2013.01); *A61M 2205/825* (2013.01); *A61N 1/0534* (2013.01); *A61N 1/372* (2013.01); *A61N 5/1071* (2013.01); *A61N 2005/1087* (2013.01); *A61N 2007/0021* (2013.01)

(56) References Cited

U.S. PATENT DOCUMENTS

| | | |
|---|---|---|
| 5,662,109 A | 9/1997 | Hutson |
| 5,749,909 A | 5/1998 | Schroeppel et al. |
| 6,170,488 B1 | 1/2001 | Spillman, Jr. et al. |
| 6,200,265 B1 | 3/2001 | Walsh et al. |
| 6,216,022 B1 | 4/2001 | Tyrrell et al. |
| 6,239,724 B1 | 5/2001 | Doron et al. |
| 6,628,989 B1 | 9/2003 | Penner et al. |
| 6,654,638 B1 | 11/2003 | Sweeney |
| 7,024,248 B2 | 4/2006 | Penner et al. |
| 7,418,292 B2 | 8/2008 | Shafer |
| 7,479,112 B2 | 1/2009 | Sweeney et al. |
| 7,616,990 B2 | 11/2009 | Chavan et al. |
| 7,634,318 B2 | 12/2009 | Tran et al. |
| 7,757,565 B2 | 7/2010 | Chakrabartty |
| 7,769,442 B2 | 8/2010 | Shafer |
| 7,848,815 B2 | 12/2010 | Brisken et al. |
| 7,890,173 B2 | 2/2011 | Brisken et al. |
| 7,899,542 B2 | 3/2011 | Cowan et al. |
| 7,953,493 B2 | 5/2011 | Fowler et al. |
| 8,078,283 B2 | 12/2011 | Cowan et al. |
| 8,082,041 B1 | 12/2011 | Radziemski |
| 8,412,338 B2 | 4/2013 | Faltys |
| 8,480,585 B2 | 7/2013 | Slayton et al. |
| 8,494,637 B2 | 7/2013 | Cowan et al. |
| 8,494,639 B2 | 7/2013 | Cowan et al. |
| 8,494,642 B2 | 7/2013 | Cowan et al. |
| 8,494,643 B2 | 7/2013 | Cowan et al. |
| 8,494,644 B2 | 7/2013 | Cowan et al. |
| 8,612,002 B2 | 12/2013 | Faltys et al. |
| 8,634,908 B2 | 1/2014 | Cowan |
| 8,718,773 B2 | 5/2014 | Willis et al. |
| 8,787,526 B2 * | 7/2014 | Hyde .................. A61N 5/1048 378/65 |
| 8,788,034 B2 | 7/2014 | Levine et al. |
| 8,849,412 B2 | 9/2014 | Perryman et al. |
| 8,855,767 B2 | 10/2014 | Faltys et al. |
| 8,874,233 B2 | 10/2014 | Mclaughlin et al. |
| 8,886,339 B2 | 11/2014 | Faltys et al. |
| 8,934,972 B2 | 1/2015 | Penner |
| 8,996,116 B2 | 3/2015 | Faltys et al. |
| 9,162,064 B2 | 10/2015 | Faltys et al. |
| 9,174,041 B2 | 11/2015 | Faltys et al. |
| 9,199,089 B2 | 12/2015 | Perryman et al. |
| 9,211,410 B2 | 12/2015 | Levine et al. |
| 9,220,897 B2 | 12/2015 | Perryman et al. |
| 9,242,103 B2 | 1/2016 | Perryman et al. |
| 9,364,362 B2 | 6/2016 | Berkcan et al. |
| 9,409,030 B2 | 8/2016 | Perryman et al. |
| 9,452,286 B2 | 9/2016 | Cowan et al. |
| 9,544,068 B2 | 1/2017 | Arbabian et al. |
| 9,566,449 B2 | 2/2017 | Perryman et al. |
| 9,623,253 B2 | 4/2017 | Perryman et al. |
| 9,700,716 B2 | 7/2017 | Faltys et al. |
| 9,717,921 B2 | 8/2017 | Perryman et al. |
| 9,757,571 B2 | 9/2017 | Perryman et al. |
| 9,789,314 B2 | 10/2017 | Perryman et al. |
| 9,802,055 B2 | 10/2017 | Reinke et al. |
| 9,833,621 B2 | 12/2017 | Levine |
| 9,849,286 B2 | 12/2017 | Levine et al. |
| 9,925,384 B2 | 3/2018 | Perryman et al. |
| 9,974,593 B2 | 5/2018 | Barman |
| 9,974,965 B2 | 5/2018 | Perryman et al. |
| 9,993,651 B2 | 6/2018 | Faltys et al. |
| 10,118,054 B2 | 11/2018 | Maharbiz et al. |
| 10,201,706 B2 | 2/2019 | Schwab et al. |
| 10,220,203 B2 | 3/2019 | Faltys et al. |
| 10,300,309 B2 | 5/2019 | Maharbiz et al. |
| 10,300,310 B2 | 5/2019 | Maharbiz et al. |
| 10,576,305 B2 | 3/2020 | Maharbiz et al. |
| 10,682,530 B2 | 6/2020 | Maharbiz et al. |
| 10,744,347 B2 | 8/2020 | Maharbiz et al. |
| 10,765,865 B2 | 9/2020 | Maharbiz et al. |
| 10,898,736 B2 | 1/2021 | Maharbiz et al. |
| 11,033,746 B2 | 6/2021 | Maharbiz et al. |
| 11,320,588 B1 * | 5/2022 | Mazed .................. G16H 10/40 |
| 11,589,748 B2 | 2/2023 | Maharbiz et al. |
| 11,607,128 B2 | 3/2023 | Maharbiz et al. |
| 2005/0049492 A1 | 3/2005 | Sweeney et al. |
| 2005/0075702 A1 | 4/2005 | Shafer |
| 2005/0152946 A1 | 7/2005 | Hunter et al. |
| 2006/0195143 A1 | 8/2006 | McClure et al. |
| 2006/0224188 A1 | 10/2006 | Libbus et al. |
| 2007/0093875 A1 | 4/2007 | Chavan et al. |
| 2007/0293912 A1 | 12/2007 | Cowan et al. |
| 2008/0108915 A1 | 5/2008 | Penner |
| 2009/0018403 A1 | 1/2009 | Black et al. |
| 2009/0228078 A1 | 9/2009 | Zhang et al. |
| 2009/0275997 A1 | 11/2009 | Faltys et al. |
| 2010/0268078 A1 | 10/2010 | Scarantino et al. |
| 2011/0054569 A1 | 3/2011 | Zitnik et al. |
| 2011/0288615 A1 | 11/2011 | Armstrong et al. |
| 2013/0003184 A1 | 1/2013 | Duparre |
| 2013/0018438 A1 | 1/2013 | Chow |
| 2013/0062527 A1 | 3/2013 | Hyde et al. |
| 2013/0178915 A1 | 7/2013 | Radziemski et al. |

(56) References Cited

U.S. PATENT DOCUMENTS

| | | |
|---|---|---|
| 2013/0226259 A1 | 8/2013 | Penner |
| 2014/0128932 A1 | 5/2014 | Ewert et al. |
| 2014/0253435 A1 | 9/2014 | Boser et al. |
| 2014/0336474 A1 | 11/2014 | Arbabian et al. |
| 2014/0336727 A1 | 11/2014 | Perryman et al. |
| 2015/0100110 A1 | 4/2015 | Towe et al. |
| 2015/0112233 A1 | 4/2015 | Towe et al. |
| 2015/0190070 A1 | 7/2015 | Bonmassar et al. |
| 2015/0241447 A1 | 8/2015 | Zitnik et al. |
| 2015/0297900 A1 | 10/2015 | Perryman et al. |
| 2016/0000590 A1 | 1/2016 | Boyden et al. |
| 2016/0007893 A1 | 1/2016 | Roberts |
| 2016/0023003 A1 | 1/2016 | Perryman et al. |
| 2016/0038741 A1 | 2/2016 | Perryman et al. |
| 2016/0038769 A1 | 2/2016 | Sullivan et al. |
| 2016/0067497 A1 | 3/2016 | Levine et al. |
| 2016/0114165 A1 | 4/2016 | Levine et al. |
| 2016/0331952 A1 | 11/2016 | Faltys et al. |
| 2016/0331962 A1 | 11/2016 | Schwab et al. |
| 2017/0100588 A1 | 4/2017 | Schwab et al. |
| 2017/0100589 A1 | 4/2017 | Schwab et al. |
| 2017/0100604 A1 | 4/2017 | Schwab et al. |
| 2017/0100605 A1 | 4/2017 | Schwab et al. |
| 2017/0117753 A1 | 4/2017 | Charthad et al. |
| 2017/0125892 A1 | 5/2017 | Arbabian et al. |
| 2017/0197082 A1 | 7/2017 | Pang et al. |
| 2018/0008828 A1 | 1/2018 | Perryman et al. |
| 2018/0085605 A1* | 3/2018 | Maharbiz ............... A61B 8/48 |
| 2018/0117319 A1 | 5/2018 | Chew et al. |
| 2018/0117320 A1 | 5/2018 | Levine et al. |
| 2018/0169423 A1 | 6/2018 | Perryman et al. |
| 2018/0236248 A1 | 8/2018 | Perryman et al. |
| 2018/0264277 A1 | 9/2018 | Perryman et al. |
| 2018/0289970 A1 | 10/2018 | Faltys et al. |
| 2019/0022427 A1 | 1/2019 | Maharbiz et al. |
| 2019/0022428 A1 | 1/2019 | Maharbiz et al. |
| 2019/0150882 A1 | 5/2019 | Maharbiz et al. |
| 2019/0150883 A1 | 5/2019 | Maharbiz et al. |
| 2019/0150884 A1 | 5/2019 | Maharbiz et al. |
| 2019/0154439 A1* | 5/2019 | Binder ............... G01B 11/26 |
| 2019/0247664 A1 | 8/2019 | Irazoqui et al. |
| 2019/0321640 A1 | 10/2019 | Carmena et al. |
| 2019/0321644 A1 | 10/2019 | Maharbiz et al. |
| 2019/0336057 A1* | 11/2019 | Alford ............... A61B 5/0261 |
| 2020/0023208 A1 | 1/2020 | Maharbiz et al. |
| 2020/0023209 A1 | 1/2020 | Maharbiz et al. |
| 2020/0114175 A1 | 4/2020 | Maharbiz et al. |
| 2020/0230441 A1 | 7/2020 | Maharbiz et al. |
| 2020/0289857 A1 | 9/2020 | Maharbiz et al. |
| 2020/0324148 A1 | 10/2020 | Maharbiz et al. |
| 2020/0410189 A1* | 12/2020 | Kitchens ............... G06F 21/32 |
| 2021/0268294 A1 | 9/2021 | Maharbiz et al. |
| 2021/0308462 A1 | 10/2021 | Carmena et al. |
| 2022/0047869 A1 | 2/2022 | Carmena et al. |
| 2022/0062650 A1* | 3/2022 | Maharbiz ............... H02J 50/15 |
| 2022/0104822 A1* | 4/2022 | Shelton, IV ....... A61B 17/1155 |
| 2022/0143414 A1* | 5/2022 | Maharbiz ............... A61B 5/024 |
| 2023/0095948 A1* | 3/2023 | Maharbiz ............. A61B 5/1459 600/476 |

FOREIGN PATENT DOCUMENTS

| | | |
|---|---|---|
| EP | 2667942 A2 | 12/2013 |
| EP | 2694154 A1 | 2/2014 |
| EP | 2741810 A1 | 6/2014 |
| EP | 2162185 B1 | 7/2015 |
| EP | 2928557 A2 | 10/2015 |
| EP | 2707094 B1 | 2/2016 |
| EP | 2755718 B1 | 12/2017 |
| EP | 2736592 B1 | 1/2018 |
| EP | 3285856 A | 2/2018 |
| EP | 3294376 A | 3/2018 |
| EP | 3338855 A1 | 6/2018 |
| EP | 2440284 B1 | 9/2018 |
| EP | 3403690 A1 | 11/2018 |
| JP | S482192 U | 1/1973 |
| JP | 2000506410 A | 5/2000 |
| JP | 2001513679 A | 9/2001 |
| JP | 2009512505 A | 3/2009 |
| JP | 2011505963 A | 3/2011 |
| JP | 2013059633 A | 4/2013 |
| JP | 2014521403 A | 8/2014 |
| JP | 2015521067 A | 7/2015 |
| JP | 2015211801 A | 11/2015 |
| JP | 2016517283 A | 6/2016 |
| JP | 2019527568 A | 10/2019 |
| WO | WO-9733513 A1 | 9/1997 |
| WO | WO-9837926 A1 | 9/1998 |
| WO | WO/2005/032653 A1 | 4/2005 |
| WO | WO-2005103873 A2 | 11/2005 |
| WO | WO/2007/050657 A1 | 5/2007 |
| WO | WO/2007/090159 A1 | 8/2007 |
| WO | WO/2010/059617 A2 | 5/2010 |
| WO | WO/2010/144578 A2 | 12/2010 |
| WO | WO/2011/028763 A2 | 3/2011 |
| WO | WO/2011/079309 A2 | 6/2011 |
| WO | WO/2012/057868 A1 | 5/2012 |
| WO | WO/2012/103519 A2 | 8/2012 |
| WO | WO/2012/138782 A1 | 10/2012 |
| WO | WO/2012/154865 A2 | 11/2012 |
| WO | WO/2013/019757 A2 | 2/2013 |
| WO | WO/2013/025632 A1 | 2/2013 |
| WO | WO/2013/040549 A1 | 3/2013 |
| WO | WO/2013/044207 A1 | 3/2013 |
| WO | WO/2013/134479 A1 | 9/2013 |
| WO | WO-2013174414 A1 | 11/2013 |
| WO | WO/2014/089299 A2 | 6/2014 |
| WO | WO-2014130960 A1 | 8/2014 |
| WO | WO/2014/153218 A1 | 9/2014 |
| WO | WO/2014/153219 A1 | 9/2014 |
| WO | WO/2014/153223 A1 | 9/2014 |
| WO | WO/2014/153228 A1 | 9/2014 |
| WO | WO/2014/169145 A1 | 10/2014 |
| WO | WO/2015/127476 A1 | 8/2015 |
| WO | WO/2015/142842 A2 | 9/2015 |
| WO | WO-2016098405 A1 | 6/2016 |
| WO | WO/2016/170510 A1 | 10/2016 |
| WO | WO/2016/183353 A1 | 11/2016 |
| WO | WO/2016/187114 A1 | 11/2016 |
| WO | WO-2017030900 A1 | 2/2017 |
| WO | WO/2018/009905 A2 | 1/2018 |
| WO | WO/2018/009908 A1 | 1/2018 |
| WO | WO/2018/009910 A1 | 1/2018 |
| WO | WO/2018/009911 A1 | 1/2018 |
| WO | WO/2018/009912 A1 | 1/2018 |
| WO | WO/2018/081763 A1 | 1/2018 |
| WO | WO/2018/081826 A1 | 5/2018 |
| WO | WO/2018/087193 A1 | 5/2018 |
| WO | WO/2018/089895 A2 | 5/2018 |
| WO | WO/2018/118857 A1 | 6/2018 |
| WO | WO/2018/118860 A1 | 6/2018 |
| WO | WO/2018/118861 A1 | 6/2018 |
| WO | WO/2018/118864 A1 | 6/2018 |
| WO | WO/2018/118866 A1 | 6/2018 |
| WO | WO-2021168163 A1 | 8/2021 |
| WO | WO-2021168229 A1 | 8/2021 |

OTHER PUBLICATIONS

U.S. Final Office Action dated Jul. 27, 2018 issued in U.S. Appl. No. 15/702,301.

U.S. Notice of Allowance dated Aug. 24, 2018 issued in U.S. Appl. No. 15/702,301.

U.S. Notice of Allowance dated Jan. 11, 2019 issued in U.S. Appl. No. 16/141,902.

U.S. Notice of Allowance dated Jan. 9, 2019 issued in U.S. Appl. No. 16/141,930.

PCT International Search Report and Written Opinion dated Jan. 2, 2018 issued in PCT/US2017/041257.

PCT International Preliminary Report on Patentability and Written Opinion dated Jan. 17, 2019 issued in PCT/US2017/041257.

(56) References Cited

OTHER PUBLICATIONS

PCT International Search Report and Written Opinion dated Nov. 15, 2017 issued in PCT/US2017/041260.
PCT International Preliminary Report on Patentability and Written Opinion dated Jan. 17, 2019 issued in PCT/US2017/041260.
PCT International Search Report and Written Opinion dated Nov. 13, 2017 issued in PCT/US2017/041263.
PCT International Preliminary Report on Patentability and Written Opinion dated Jan. 17, 2019 issued in PCT/US2017/041263.
PCT International Search Report and Written Opinion dated Sep. 20, 2017 issued in PCT/US2017/041262.
PCT International Preliminary Report on Patentability and Written Opinion dated Jan. 17, 2019 issued in PCT/US2017/041262.
PCT International Search Report and Written Opinion dated Nov. 2, 2017 issued in PCT/US2017/041264.
PCT International Preliminary Report on Patentability and Written Opinion dated Jan. 17, 2019 issued in PCT/US2017/041264.
Afroz et al., "Implantable Sic Based RF Antenna Biosensor for Continuous Glucose Monitoring", IEEE, 2013, 4 pages.
Ahmadi et al., "A Wireless-Implantable Microsystem for Continuous Blood Glucose Monitoring", IEEE Transactions on Biomedical Circuits and Systems, vol. 3 No. 3, Jun. 2009, pp. 169-180.
Alivisatos et al., "Nanotools for Neuroscience and Brain Activity Mapping", ACS Nano, vol. 7, No. 3, 2013, pp. 1850-1866.
Bai et al., "Single-Unit neural Recording with Active Microelectrode Arrays", IEEE Transactions on Biomedical Engineering, vol. 48, No. 8, Aug. 2001, pp. 911-920.
Bartlett et al., "Strategies for the Development of Amperometric Enzyme Electrodes", Biosensors, vol. 3, 1987, pp. 359-379.
Bertrand et al., "Beamforming Approaches for Untethered, Ultrasonic Neural Dust Motes for Cortical Recording: A Simulation Study", 36th Annual International Conference of the IEEE Engineering in Medicine and Biology Society, 2014, pp. 2625-2628.
Beuter et al., "Closed-Loop Cortical Neuromodulation in Parkinson's Disease: An Alternative to Deep Brain Stimulation?", Clinical Neurophysiology, vol. 125, 2014, pp. 874-885.
Beyer et al., "An Implantable MOSFET Dosimeter for the Measurement of Radiation Dose in Tissue During Cancer Therapy", IEEE Sensors Journal, vol. 8, No. 1, 2008, pp. 38-51.
Bhadra et al., "High-Frequency Electrical Conduction Block of Mammalian Peripheral Motor Nerve", Muscle Nerve, vol. 32, No. 6, Dec. 2005, pp. 782-790.
Biederman et al., "A 4.78 mm 2 Fully-Integrated Neuromodulation SoC Combining 64 Acquisition Channels with Digital Compression and Simultaneous Dual Stimulation", IEEE Journal of Solid-State Circuits, vol. 50, No. 4, 2015, pp. 1038-1047.
Biederman et al., "A Fully-Integrated, Miniaturized (0.125 mm$^2$) 10.5 µW Wireless Neural Sensor", IEEE Journal of Solid-State Circuits, vol. 48, No. 4, 2013, pp. 960-970.
Birmingham et al., "Bioelectronic Medicines: A Research Roadmap", Nature Reviews Drug Discovery, vol. 13, No. 6, 2014, pp. 399-400.
Boretius et al., "A Transverse Intrafascicular Multichannel Electrode (Time) to Interface with the Peripheral Nerve", Biosensors and Bioelectronics, vol. 26, No. 1, Sep. 2010, pp. 62-69.
Cardin et al., "Targeted Optogenetic Stimulation and Recording of Neurons in Vivo Using Cell-Type-Specific Expression of Channelrhodopsin-2", Nature Protocols, vol. 5, 2010, pp. 247-254.
Carmena et al., "Learning to Control a Brain-Machine Interface for Reaching and Grasping by Primates", PLoS Biology, vol. 1, No. 2, 2003, pp. 193-208.
Carvalho-De-Souza et al., "Photosensitivity of Neurons Enabled by Cell-Targeted Gold Nanoparticles", Neuron, vol. 86, No. 1, Apr. 8, 2015, pp. 207-217.
Celinskis, Dmitrijs et al., "Wireless impedance measurements for monitoring peripheral vascular disease", 36th Annual International Conference of the IEEE Engineering in Medicine and Biology Society, IEEE, 2014, pp. 6937-6940.
Chapin et al., "Real-Time Control of a Robot Arm Using Simultaneously Recorded Neurons in the Motor Cortex", Nature Neuroscience, vol. 2, 1999, pp. 664-670.

Charthad et al., "A mm-Sized Implantable Medical Device (IMD) with Ultrasonic Power Transfer and a Hybrid Bi-Directional Data Link", IEEE Journal of Solid-State Circuits, vol. 50, No. 8, 2015, pp. 1741-1753.
Chestek et al., "Long-Term Stability of Neural Prosthetic Control Signals From Silicon Cortical Arrays in Rhesus Macaque Motor Cortex", Journal of Neural Engineering, vol. 8, 2011, pp. 1-11.
Cogan et al., "Plasma-Enhanced Chemical Vapor Deposited Silicon Carbide as an Implantable Dielectric Coating", Journal of Biomedical Research: Part A, vol. 67A, No. 3, Oct. 20, 2003, pp. 856-867.
Creasey et al., "An Implantable Neuroprosthesis for Restoring Bladder and Bowel Control to Patients with Spinal Cord Injuries: A Multicenter Trial", Archives of Physical Medicine and Rehabilitation, vol. 82, No. 11,, Nov. 2001, pp. 1512-1519.
Dadarlat et al., "A Learning-Based Approach to Artificial Sensory Feedback Leads to Optimal Integration", Nature Neuroscience, vol. 18, No. 1, Jan. 2015, pp. 138-144.
Delivopoulos et al., "Concurrent Recordings of Bladder Afferents from Multiple Nerves Using a Microfabricated PDMS Microchannel Electrode Array", Lab on a Chip, vol. 12, No. 14, Jul. 2012, pp. 2540-2551.
Dellis, Jean-Luc, "Zfit", version 1.2, MathWorks, Updated on 2010, 6 pages.
Denison et al., "A 2 µW, 100 nV/rtHz, Chopper-Stabilized Instrumentation Amplifier for Chronic Measurement of Neural Field Potentials", IEEE Journal of Solid-State Circuits, vol. 42 No. 12, 2007, pp. 2934-2945.
Dingli et al., "Successful Therapy Must Eradicate Cancer Stem Cells", Stem Cells, vol. 24, 2006, pp. 2603-2610.
Du et al., "Multiplexed, High Density Electrophysiology with Nanofabricated Neural Probes", PLOS One, vol. 6, No. 10, Oct. 2011, pp. e26204.1-11.
Epoxy Technology, "EPO-TEK H20E", Rev. XIII, Jul. 2015, 2 pages.
Famm et al., "Drug Discovery: A Jump-Start for Electroceuticals", Nature, vol. 496, Apr. 2013, pp. 159-161.
Fan et al., "A Wireless Multi-Channel Recording System for Freely Behaving Mice and Rats", PLoS One, vol. 6, No. 7, Jul. 2011, pp. e22033.1-9.
Food and Drug Administration, "Information for Manufacturers Seeking Marketing Clearance of Diagnostic Ultrasound Systems and Transducers", Guidance for Industry and FDA Staff, Sep. 9, 2008, 68 pages.
Foster et al., "A Freely-Moving Monkey Treadmill Model", Journal of Neural Engineering, vol. 11, 2014, pp. 1-14.
Frewin et al., "Silicon Carbide Materials for Biomedical Applications", Carbon for Sensing Devices, Oct. 8, 2014, pp. 153-207.
Ganguly et al., "Emergence of a Stable Cortical Map for Neuroprosthetic Control", PLoS Biology, vol. 7, No. 7, Jul. 2009, pp. e1000153.1-13.
Girman et al., "Rat Experimental Transplantation Surgery: A Pactical Guide", Springer, eBook, 2015, 257 pages.
Gold et al., "Using Extracellular Action Potential Recordings to Constrain Compartmental Models", Journal of Computational Neuroscience, vol. 23, 2007, pp. 39-58.
Grahn et al., "A Neurochemical Closed-Loop Controller for Deep Brain-Stimulation: Toward Individualized Smart Neuromodulation Therapies", Frontiers in Neuroscience, vol. 8, Article 169, Jun. 2014, pp. 1-11.
Gruner et al., "Nonlinear Muscle Recruitment During Intramuscular and Nerve Stimulation", Journal of Rehabilitation Research and Development, vol. 26, No. 2, 1989, pp. 1-16.
Halperin et al., "Perez and Brady's Principles and Practice of Radiation Oncology", Lippincott Williams & Wilkins, 6th Edition, 2013, 2 pages.
Harman-Boehm et al., "Noninvasive Glucose Monitoring: A Novel Approach", Journal of Diabetes Science and Technology, vol. 3, No. 2, Mar. 2009, pp. 253-260.
Harrison et al., "A Low-Power Integrated Circuit for a Wireless 100-Electrode Neural Recording System", IEEE Journal of Solid-State Circuits, vol. 42, No. 1, 2007, pp. 123-133.

(56) References Cited

OTHER PUBLICATIONS

Harrison, Reid R., "Designing Efficient Inductive Power Links for Implantable Devices", IEEE International Symposium on Circuits and Systems, 2007, pp. 2080-2083.

He et al., "Nanoscale Neuro-Integrative Coatings for Neural Implants", Biomaterials, vol. 26, 2005, pp. 2983-2990.

Hess et al., "PECVD Silicon Carbide as a Thin Film Packaging Material for Microfabricated Neural Electrodes", Materials Research Society Symposium Proceedings, vol. 1009, 2007, pp. 8-13.

Hochberg et al., "Reach and Grasp by People with Tetraplegia Using a Neurally Controlled Robotic Arm", Nature, vol. 485, May 2012, pp. 372-375.

Holland, Richard, "Resonant Properties of Piezoelectric Ceramic Rectangular Parallelepipeds", The Journal of the Acoustical Society of America, vol. 43, No. 5, 1968, pp. 988-997.

Holmes-Siedle et al., "RADFET: A Review of the Use of Metal-Oxide-Silicon Devices as Dosimeters", International Journal of Radiation Applications and Instrumentation, Part C, Radiation Physics and Chemistry, vol. 28, No. 2, 1986, pp. 235-244.

Holmes-Siedle et al., "The Physics of Failure of MIS Devices Under Radiation", IEEE Transactions on Reliability, vol. R-17, No. 1, 1968, pp. 34-44.

Hoskins et al., "Diagnostic Ultrasound: Physics and Equipment", 2003, 276 pages.

Hynynen et al., "Demonstration of Potential Noninvasive Ultrasound Brain Therapy through an Intact Skull", Ultrasound in Medicine and Biology, vol. 24, No. 2, Feb. 1998, pp. 275-283.

IEEE, "IEEE Standard for Safety Levels with Respect to Human Emposure to Radio Frequency Electromagnetic Fileds, 3khz to 300 Ghz", IEEE Standards Coordinating Committee 28 on Non-Ionizing Radiation Hazards, 1991, 72 pages.

IEEE, "IEEE Standard for Safety Levels with Respect to Human Exposure to Radio Frequency Electromagnetic Fields, 3 kHz to 300 GHz", IEEE International Committee on Electromagnetic Safety (SCC39), Apr. 2006, 250 pages.

Ishida et al., "Insole Pedometer With Piezoelectric Energy Harvester and 2 V Organic Circuits", IEEE Journal of Solid-State Circuits, vol. 48, No. 1, 2013, pp. 255-264.

Jow et al., "Design and Optimization of Printed Spiral Coils for Efficient Transcutaneous Inductive Power Transmission", IEEE Transactions on Biomedical Circuits and Systems, vol. 1, No. 3, 2007, pp. 193-202.

Kay, Joshua, "Rodent Wearable Ultrasound Interrogation System for Wireless Neural Recording", Berkeley EECS, Technical Report No. UCS/EECS-2017-27, May 4, 2017, 50 pages.

Kim et al., "Injectable, Cellular-Scale Optoelectronics with Applications for Wireless Optogenetics", Science, vol. 340, Apr. 12, 2013, pp. 211-216.

Kiourti et al., "A Wireless Fully Passive Neural Recording Device for Unobtrusive Neuropotential Monitoring", IEEE Transactions on Biomedical Engineering, vol. 63, No. 1, 2016, pp. 131-137.

Klueh et al., "Metabolic Biofouling of Glucose Sensors in Vivo: Role of Tissue Microhemorrhages", Journal of Diabetes Science and Technology, vol. 5, No. 3, May 2011, pp. 583-595.

Koralek et al., "Corticostriatal Plasticity is Necessary for Learning Intentional Neuroprosthetic Skills", Nature, vol. 483, Mar. 15, 2012, pp. 331-335.

Kozai et al., "Ultrasmall Implantable Composite Microelectrodes with Bioactive Surfaces for Chronic Neural Interfaces", Nature Materials, vol. 11, 2012, pp. 1065-1073.

Krimholtz et al., "New Equivalent Circuits for Elementary Piezoelectric Transducers", Electronics Letters, vol. 6, No. 13, 1970, pp. 398-399.

Krook-Magnuson, "Neuroelectronics and Biooptics: CLoed Loop Technologies in Neurological Disorders", JAMA Neurology, vol. 72, No. 7, Jul. 2015, pp. 823-829.

Kuo et al., "Associations Between Periodontal Diseases and Systematic Disease: A Review of the Inter-relationships and Interactions with Diabetes, Respiratory Diseases, Cardiovascular Diseases and Osteoporosis", Public Health, vol. 122, No. 4, Apr. 2008, pp. 417-433.

Lapatki et al., "A Thin, Flexible Multielectrode Grid for High-Density Surface EMG", Journal of Applied Physiology, vol. 96, No. 1, Jan. 2004, pp. 327-336.

Larson et al., "Miniature Ultrasonically Powered Wireless Nerve Cuff Stimulator", Proceedings of the 5th International IEEE/EMBS Conference on Neural Engineering, 2011, pp. 265-268.

Ledochowitsch et al., "Fabrication and Testing of a Large Area, High Density, Parylene MEMS µECOG Array", IEEE 24th International Conference on Micro Electro Mechanical Systems, 2011, pp. 1031-1034.

Lee et al., "A Wideband Dual-Antenna Receiver for Wireless Recording from Animals Behaving in Large Arenas", IEEE Transactions on Biomedical Engineering, vol. 60, No. 7, 2013, pp. 1993-2004.

Lee et al., "An Inductively Powered Scalable 32-Channel Wireless Neural Recording System-on-a-Chip for Neuroscience Applications", IEEE Transactions on Biomedical Circuits and Systems, vol. 4, No. 6, 2010, pp. 360-371.

Lefurge et al., "Chronically Implanted Intrafascicular Recording Electrodes", Annals of Biomedical Engineering, vol. 19, No. 2, 1991, pp. 197-207.

Leighton, Timothy G., "What is Ultrasound", Progress in Biophysics and Molecular Biology, vol. 93, 2007, pp. 3-83.

Lin et al., "Low Phase Noise Array-Composite Micromechanical Wine-Glass Disk Oscillator", IEEE InternationalElectron Devices Meeting, IEDM Technical Digest, 2005, pp. 1-4.

Lind et al., "The Density Difference Between Tissue and Neural Probes is A Key Factor for Glial Scarring", Scientific Reports, vol. 3, 2013, pp. 2942.1-7.

Liu et al., "Monte Carlo Simulation Studies of EEG and MEG Localization Accuracy", Human Brain Mapping, vol. 16, 2002, pp. 47-62.

Lu et al., "Current Challenges to the Clinical Translation of Brain Machine Interface Technology", International Review of Neurobiology, vol. 107, 2012, pp. 137-160.

Maleki et al., "An Ultrasonically Powered Implantable Micro-Oxygen Generator (IMOG)", IEEE Transactions on Biomedical Engineering, 2011, pp. 3104-3111.

Malmivuo et al., "Effect of Skull Resistivity on the Spatial Resolutions of EEG and MEG", IEEE Transactions on Biomedical Engineering, , vol. 51 No. 7, Jul. 7, 2004, pp. 1276-1280.

Marblestone et al., "Physical Principles for Scalable Neural Recording", Frontiers in Computational Neuroscience, vol. 7, Article 137, Oct. 2013, pp. 1-34.

Martinez-Valdes et al., "High-Density Surface Electromyography Provides Reliable Estimates of Motor Unit Behaviour", Clinical Neurophysiology, vol. 127, No. 6, 2016, pp. 2534-2541.

Maynard et al., "The Utah Intracortical Electrode Array: a Recording Structure for Potential Brain-Computer Interfaces", Electroencephalography and Clinical Neurophysiology, vol. 102, 1997, pp. 228-239.

Mazzilli et al., "In-Vitro Platform to study Ultrasound as Source for Wireless Energy Transfer and Communication for Implanted Medical Devices", 32nd Annual International Conference of the IEEE EMBS, 2010, pp. 3751-3754.

Meacham et al., "A Lithographically-Patterned, Elastic Multi-Electrode Array for Surface Stimulation of the Spinal Cord", Biomedical Microdevices, vol. 10, 2008, pp. 259-269.

Meng et al., "An Electroacoustic Recording Device for Wireless Sensing of Neural Signals", 35th Annual International Conference of the IEEE Engineering in Medicine and Biology Society (EMBC), 2013, pp. 3086-3088.

Mezzarane et al., "Experimental and Simulated EMG Responses in the Study of the Human Spinal Cord", Chapter 4, Electrodiagnosis in New Frontiers of Clinical Research, 2013, pp. 57-87.

Miranda et al., "HermesD: A High-Rate Long-Range Wireless Transmission System for Simultaneous Multichannel Neural Recording Applications", IEEE Transactions on Biomedical Circuits and Systems, vol. 4, No. 3, Jun. 2010, pp. 181-191.

(56) References Cited

OTHER PUBLICATIONS

Mohan et al., "Simple Accurate Expressions for Planar Spiral Inductances", IEEE Journal of Solid-State Circuits, vol. 34, No. 10, Oct. 1999, pp. 1419-1424.
Mohseni et al., "Guest Editorial Closing the Loop Via Advanced Neurotechnologies", IEEE Transactions on Neural Systems and Rehabilitation Engineering, vol. 20, No. 4, Jul. 2012, pp. 407-409.
Muller et al., "A 0.013 mm2, 5 µW, DC-Coupled Neural Signal Acquisition IC With 0.5 V Supply", IEEE Journal of Solid-State Circuits, vol. 47, No. 1, Jan. 2012, pp. 232-243.
Muller et al., "A Minimally Invasive 64-Channel Wireless µECoG Implant", IEEE Journal of Solid-State Circuits, vol. 50, No. 1,, Jan. 2015, pp. 1-16.
Nicolelis et al., "Chronic, Multisite, Multielectrode Recordings in Macaque Monkeys", PNAS, vol. 100, No. 19, Sep. 16, 2003, pp. 11041-11046.
Nicolelis, Miguel A. L., "Brain-Machine Interfaces to Restore Motor Function and Probe Neural Circuits", Nature Reviews Neuroscience, vol. 4, May 2003, pp. 417-422.
O'Doherty et al., "Active Tactile Exploration Using a Brain-Machine-Brain Interface", Nature, vol. 479, Nov. 10, 2011, pp. 228-231.
Ozeri et al., "Ultrasonic Transcutaneous Energy Transfer for Powering Implanted Devices", Ultrasonics, vol. 50, 2010, pp. 556-566.
Pavlov et al., "The Vagus Nerve and the Inflammatory Reflex-Linking Immunity and Metabolism", Nat Rev Endocrinol., vol. 8, No. 12, Dec. 2012, pp. 743-754.
Peisino, Michela, "Deeply implanted medical device based on a novel ultrasonic telemetry technology", Ecole Polytechnique Federale De Lausanne, 2013, pp. 147. Retrieved from the Internet: URL:https://infoscience.epfl.ch/record/186391/files/EPFL_TH5730.pdf [retrieved on Mar. 23, 2015].
Polikov et al., "Response of Brain Tissue to Chronically Implanted Neural Electrodes", Journal of Neuroscience Methods, vol. 148, 2005, pp. 1-18.
Polikov, et al., "In Vitro Model of Glial Scarring Around Neuroelectrodes Chronically Implanted in the CNS", Biomaterials, vol. 27, 2006, pp. 5368-5376.
Potter et al., "Stab Injury and Device Implantation within the Brain Results in Inversely Multiphasic Neuroinflammatory and Neurodegenerative Responses", Journal of Neural Engineering, vol. 9, No. 4, 2012, pp. 046020.
Rabaey et al., "Powering and Communicating with mm-Size Implants", IEEE, Design, Automation & Test in Europe, 2011, pp. 1-6.
Ramachnadran et al., "A Study of Parylene C Polymer Deposition Inside Microscale Gaps", IEEE Transactions on Advanced Packaging, vol. 30, 2007, pp. 712-724.
Randals, J.E.B, "Kinetics of Rapid Electrode Reactions", Discussions of the Faraday Society, vol. 1, 1947, pp. 11-19.
Rebrin et al., "Subcutaneous Glucose Monitoring by Means of Electrochemical Sensors: Fiction or Reality? ", Journal of Biomedical Engineering, vol. 14, Jan. 1992, pp. 33-40.
Richards et al., "Efficiency of Energy Conversion for Devices Containing A Piezoelectric Component", Journal of Micromechanics and Microengineering, vol. 14, 2004, pp. 717-721.
Roa-Prada et al., "An Ultrasonic Through-Wall Communication (UTWC) System Model", Journal of Vibration and Acoustics, vol. 135, No. 1, 2013, pp. 1-12.
Robinson et al., "Nanowire Electrodes for High-Density Stimulation and Measurement of Neural Circuits", Frontiers in Neural Circuits, vol. 7, Article 38, Mar. 2013, pp. 1-5.
Rogers et al., "Materials and Mechanics for Stretchable Electronics", Science, vol. 327, Mar. 26, 2010, pp. 1603-1607.
Rosas-Ballina et al., "Acetylcholine-Synthesizing T Cells Relay Neural Signals in a Vagus Nerve Circuit", Science, vol. 334, No. 6052, Oct. 7, 2011, pp. 98-101.
Saddow et al., "Advances in Silicon Carbide Processing and Applications", Artech House, Inc., 2004, 223 pages.
Sadek et al., "Wiring Nanoscale Biosensors with Piezoelectric Nanomechanical Resonators", Nano Letters, vol. 10, 2010, pp. 1769-1773.
Schwarz et al., "Chronic, Wireless Recordings of Large Scale Brain Activity in Freely Moving Rhesus Monkeys", Nat Methods, vol. 11, No. 6, 2014, pp. 670-676.
Schwerdt et al., "A Fully Passive Wireless Microsystem for Recording of Neuropotentials Using RF Backscattering Methods", Journal of Microelectromechanical Systems, vol. 20, No. 5, 2011, pp. 1119-1130.
Seo et al., "Model Validation of Untethered, Ultrasonic Neural Dust Motes for Cortical Recording", Journal of Neuroscience Methods, vol. 244, 2015, pp. 114-122.
Seo et al., "Neural Dust: An Ultrasonic, Low Power Solution for Chronic Brain-Machine Interfaces", Neurons and Cognition, Jul. 2013, pp. 1-11.
Seo et al., "Ultrasonic Beamforming System for Interrogating Multiple Implantable Sensors", Conf Proc IEEE Eng Med Biol Soc., 2015, pp. 2673-2676.
Seo et al., "Wireless Recording in the Peripheral Nervous System with Ultrasonic Neural Dust", Neuron, vol. 91, Aug. 3, 2016, pp. 529-539.
Seo, Dongjin, "Design of Ultrasonic Power Link for Neural Dust", Technical Report No. UCB/EECS-2016-21, Electrical Engineering and Computer Sciences University of California at Berkeley, May 1, 2016, 71 pages.
Serruya et al., "Instant Neural Control of a Movement Signal", Nature, vol. 416, Mar. 14, 2002, pp. 141-142.
Seymour et al., "Neural Probe Design for Reduced Tissue Encapsulation in CNS", Biomaterials, vol. 28, 2007, pp. 3594-3607.
Shapiro et al., "Infrared Light Excites Cells by Changing their Electrical Capacitance", Nature Communications, vol. 3, Article 736, 2012, 10 pages.
Shen, Konlin, "Assembly of a Wireless Ultrasonic Backscatter System", Spring 2016, 61 pages.
Shenoy et al., "Neural Prosthetic Control Signals from Plan Activity", NeuroReport, vol. 14, No. 4, Mar. 24, 2003, pp. 591-596.
Sodagar et al., "Capacitive Coupling for Power and Data Telemetry to Implantable Biomedical Microsystems", Proceedings of the 4th International IEEE EMBS Conference on Neural Engineering, Apr. 29-May 2, 2009, pp. 411-414.
Srinivasan, Ramesh, "Methods to Improve the Spatial Resolution of EEG", International Journal of Bioelectromagnetism, vol. 1, No. 1, 1999, pp. 102-111.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, vol. 20, No. 4, Jul. 2012, pp. 410-421.
Stark, Nancy, "Literature Review: Biological Safety of Parylene C", Medical Device and Diagnostic Industry, Mar. 1996, 7 pages.
Stevenson et al., "How Advances in Neural Recording Affect Data Analysis", Nature Neuroscience, vol. 14, No. 2, Feb. 2011, pp. 139-142.
Steyaert et al., "A Micropower Low-Noise Monolithic Instrumentation Amplifier for Medical Purposes", IEEE Journal of Solid-State Circuits, vol. Section-22, No. 6, Dec. 1987, pp. 1163-1168.
Strollo et al., "Upper-Airway Stimulation for Obstructive Sleep Apnea", New England Journal of Medicine, vol. 370, Jan. 9, 2014, pp. 139-149.
Stypulkowski et al., "Brain Stimulation for Epilepsy—Local and Remote Modulation of Network Excitability", Brain Stimulation, vol. 7, No. 3, 2014, pp. 350-358.
Sudhakar, Akulapalli, "History of Cancer, Ancient and Modern Treatment Methods", Journal of Cancer Science and Therapy, vol. 1, No. 2, 2009, 4 pages.
Suner et al., "Reliability of Signals from a Chronically Implanted, Silicon-Based Electrode Array in Non-Human Primate Primary Motor Cortex", IEEE Transactions on Neural Systems and Rehabilitation Engineering, vol. 13, No. 4, Dec. 2005, pp. 524-541.
Swett et al., "Motoneurons of the Rat Sciatic Nerve", Experimental Neurology, vol. 93, 1986, pp. 227-252.
Swisher et al., "Impedance Sensing Device Enables Early Detection of Pressure Ulcers in Vivo", Nature Communications, vol. 6, 2015, 17 pages.

(56) References Cited

OTHER PUBLICATIONS

Szuts et al., "A wireless Multi-Channel Neural Amplifier for Freely Moving Animals", Nature Neuroscience, vol. 14, 2011, pp. 263-269.
Tang et al., "Integrated Ultrasonic System for Measuring Body-Fat Composition", IEEE International Solid-State Circuits Conference, 2015, 3 pages.
Tang et al., "Miniaturizing Ultrasonic System for Portable Health Care and Fitness", IEEE Transactions on Biomedical Circuits and Systems, vol. 9, No. 6, Dec. 2015, pp. 767-776.
Trolier-Mckinstry et al., "Thin Film Piezoelectrics for MEMS", Journal of Electroceramics, vol. 12, 2004, pp. 7-17.
Turner et al., "Cerebral Astrocyte Response to Micromachined Silicon Implants", Experimental Neurology, vol. 156, 1999, pp. 33-49.
Updike et al., "Enzymatic Glucose Sensors: Improved Long Term Performance in Vitro and in Vivo", ASAIO Journal, vol. 40, 1994, pp. 157-163.
Venkatraman et al., "Active Sensing of Target Location Encoded by Cortical Microstimulation", IEEE Transactions on Neural Systems and Rehabilitation Engineering, vol. 19, No. 3, Jun. 2011, pp. 317-324.
Watanabe et al., "Reconstruction of Movement-Related Intracortical Activity From Micro-Electrcorticogram Array Signals in Monkey Motor Cortex", Journal of Neural Engineering, vol. 9, 2012, 58 pages.
Weissleder et al., "Molecular imaging", Radiology, vol. 219, 2001, 316-333.
Wells et al., "Optical Stimulation of Neural Tissue in Vivo", Optics Letters, vol. 30, No. 5, 2005, pp. 504-506.
Wilkins et al., "Glucose Monitoring: State of the Art and Future Possibilities", Medical Engineering and Physics, vol. 18, No. 4, 1996, pp. 273-288.
Williamson et al., "Localized Electrical Nerve Blocking", IEEE Transactions on Biomedical Engineering, vol. 52, No. 3, Mar. 2005, pp. 362-370.
Wilson et al., "Better Speech Recognition with Cochlear Implants", Letters to Nature, vol. 352, Jul. 18, 1991, pp. 236-238.
Wolgemuth, Lonny, "Assessing the Performance and Suitability of Parylene Coating", Medical Device and Diagnostic Industry, Aug. 2000, 6 pages.
Wong et al., "Advantages of Capacitive Micromachined Ultrasonics Transducers (CMUTs) for High Intensity Focused Ultrasound (HIFU)", IEEE Ultrasonics Symposium, 2007, pp. 1313-1316.
Xu et al., "Stretchable Batteries with Self-Similar Serpentine Interconnects and Integrated Wireless Recharging Systems", Nature Communications, 2013, 36 pages.
Yakolev et al., "Implantable Biomedical Devices: Wireless Powering and Communication", IEEE Communications Magazine, Apr. 2012, pp. 152-159.
Yin et al., "Wireless Neurosensor for Full-Spectrum Electrophysiology Recordings During Free Behavior", NeuroResource, Neuron, vol. 84, Dec. 17, 2014, p. 1170-1182.
Zenner et al., "Human Studies of a Piezoelectric Transducer and A Microphone For a Totally Implantable Electronic Hearing Device", The American Journal of Otology, vol. 21, No. 2, Mar. 2000, pp. 196-204 [Abstract Only].
Zorman, CH., "Silicon Carbide as a material for Biomedical Microsystems", EDA Publishing Association, 2009, 8 pages.
U.S. Office Action dated Sep. 18, 2019 issued in U.S. Appl. No. 16/380,944.
U.S. Notice of Allowance dated Dec. 17, 2019 issued in U.S. Appl. No. 16/380,944.
U.S. Office Action dated Oct. 24, 2019 issued in U.S. Appl. No. 16/398,086.
U.S. Notice of Allowance dated Feb. 11, 2020 issued in U.S. Appl. No. 16/398,086.
U.S. Office Action dated Nov. 15, 2019 issued in U.S. Appl. No. 16/401,028.
U.S. Notice of Allowance dated Jan. 10, 2020 issued in U.S. Appl. No. 16/401,028.
U.S. Notice of Allowance dated Apr. 30, 2020 issued in U.S. Appl. No. 16/401,028.
U.S. Office Action dated Jan. 9, 2020 issued in U.S. Appl. No. 16/401,041.
U.S. Final Office Action dated Jul. 2, 2020 issued in U.S. Appl. No. 16/401,041.
U.S. Notice of Allowance dated Sep. 21, 2020 issued in U.S. Appl. No. 16/401,041.
U.S. Notice of Allowance dated Apr. 20, 2020 issued in U.S. Appl. No. 16/401,060.
EP Office Action dated May 18, 2020 issued in EP 17742596.4.
AU office action dated Nov. 3, 2021, in application No. 2017292929.
AU Office Action dated Aug. 3, 2021, in Application No. AU2017292924.
AU Office Action dated Jul. 20, 2021, in Application No. AU2017292931.
CN 2nd Office Action dated Jan. 26, 2022 issued in CN 201780054777.8.
CN Office Action dated Jan. 25, 2022, in Application No. CN201780042348.9 with English Translation.
CN Office Action dated Jan. 26, 2022, in Application No. CN201780054417.8 with English translation.
CN Office Action dated Jun. 15, 2022, in Application No. CN201780042348.9.
CN Office Action dated Jun. 15, 2022, in Application No. CN201780054417.8.
CN Office Action dated Jun. 15, 2022, in Application No. CN201780054777.8.
CN Office Action dated May 7, 2021 issued in CN 201780042348.9.
CN Office Action dated May 8, 2021 issued in CN 201780054417.8.
CN Office Action dated May 8, 2021 issued in CN 201780054777.8.
EP Extended Search Report dated Feb. 23, 2021 issued in EP 20198662.7.
Extended European Search Report dated Nov. 22, 2021, in Application No. EP21193250.
JP Office Action dated Apr. 19, 2022, in Application No. JP2019-500381 with English translation.
JP Office Action dated Aug. 17, 2021, in Application No. JP2018-568204 with English translation.
JP office action dated Jun. 15, 2021, in application No. JP20190500515 with English Translation.
JP Office Action dated Jun. 29, 2021 issued in JP 2019-500381.
JP Office Action dated May 10, 2022, in Application No. JP2019-500515.
Ozeri, S., et al., "Simultaneous Backward Data Transmission and Power Harvesting in an Ultrasonic Transcutaneous Energy Transfer Link Employing Acoustically Dependent Electric Impedance Modulation," Ultrasonics, vol. 54(7), 2014, pp. 1929-1937.
Tracey, K.J., "The Inflammatory Reflex", Nature, Dec. 2002, vol. 420, pp. 853-859.
U.S. Final office Action dated Jun. 15, 2022 in U.S. Appl. No. 16/313,860.
U.S. Non-Final office Action dated Jun. 2, 2022 in U.S. Appl. No. 16/739,084.
U.S. Office Action dated Feb. 3, 2022 issued in U.S. Appl. No. 16/313,860.
U.S. Restriction Requirement dated Apr. 12, 2022 for U.S. Appl. No. 16/313,865.
U.S Restriction Requirement dated Apr. 12, 2022 in U.S. Appl. No. 16/313,862.
Webster, John G. "Medical Instrumentation: Applciation and Design", 1998, 358-371.
Arbabian, A. et al., "Sound Technologies, Sound Bodies", IEEE Microwave Magazine, Dec. 2016, pp. 39-54.
Chan, W.P. et al., "A Monolithically Integrated Pressure/Oxygen/Temperature Sensing SoC for Multimodality Intracranial Neuromonitoring", IEEE Journal of Solid-State Circuits, 2014, vol. 49, No. 11, pp. 2449-2461.
Chang, T.C. et al., "A 30.5mm$^3$ Fully Packaged Implantable Device with Duplex Ultrasonic Data and Power Links Achieving 95kb/s

(56) References Cited

OTHER PUBLICATIONS with $10^{-4}$ BER at 8.5cm Depth", Biomedical Circuits, 27.7, IEEE ISSCC, 2017, Session 27, pp. 460-461.
CN Office Action dated Jun. 15, 2022, in Application No. CN201780054417.8 with English translation.
CN Office Action dated Jun. 15, 2022, in Application No. CN201780042348.9 with English translation.
CN Office Action dated Jun. 15, 2022, in Application No. CN201780054777.8 with English translation.
Ghanbari, M.M. et al., "A 0.8mm³ Ultrasonic Implantable Wireless Neural Recording System With Linear AM Backscattering", Technologies for Human Interaction & Health, 17.5, Session 17, IEEE ISSCC, 2019, pp. 284-286.
International Preliminary Report on Patentability dated Sep. 1, 2022, in PCT Application No. PCT/US2021/018751.
International Search Report and Written Opinion dated Apr. 29, 2021 in Application No. PCT/US2021/018644.
International Search Report and Written Opinion dated Jul. 9, 2021 in Application No. PCT/US2021/018751.
Johannessen, E.A. et al., "Implementation of Multichannel Sensors for Remote Biomedical Measurements in a Microsystems Format", IEEE Transactions on Biomedical Engineering, Mar. 2004, vol. 51, No. 3, pp. 525-535.
JP Office Action dated Jun. 21, 2022 in Application No. JP2018-568204 with English translation.
JP Office Action dated May 10, 2022, in Application No. JP2019-500515 with English translation.
Sanni, A., et al "Inductive and Ultrasonic Multi-tier Interface for Low-power, Deeply Implantable Medical Devices", IEEE transactions on biomedical circuits and systems, Aug. 2012, vol. 6 No. 4, pp. 297-308.
Shen, K. et al., "Ceramic packaging in neural implants", Journal of Neural Engineering, 2021, vol. 18, No. 2, 025002, 19 pages.
Shen, K. et al., "Design of Ceramic Packages for Ultrasonically Coupled Implantable Medical Devices", IEEE Transactions on Bio-medical Engineering, Aug. 2020, vol. 67, No. 8, pp. 2230-2240.
Turchetta, R. et al.,"Monolithic active pixel sensors (MAPS) in a VLSI CMOS technology", Nuclear Instruments and Methods in Physics Research, 2003, vol. 501, pp. 251-259.
U.S. Non-Final office Action dated Sep. 15, 2022 in U.S. Appl. No. 16/313,862.
U.S. Non-Final office Action dated Sep. 28, 2022 in U.S. Appl. No. 16/313,865.
U.S. Notice of Allowance dated Sep. 19, 2022 in U.S. Appl. No. 16/739,084.
U.S. Appl. No. 17/799,891, inventors Maharbiz et al., filed Aug. 15, 2022.
U.S. Appl. No. 17/799,895, inventors Maharbiz et al., filed Aug. 15, 2022.
Yao, L. et al., "Sensitivity-Enhanced CMOS Phase Luminometry System Using Xerogel-Based Sensors", IEEE Transactions on Biomedical Circuits and Systems, Oct. 2009, vol. 3, No. 5, pp. 304-311.
CN Office Action dated Oct. 10, 2022, in Application No. CN201780054777.8 with English translation.
JP Office Action dated Feb. 21, 2023, in Application No. JP2019-500515.
JP Office Action dated Feb. 28, 2023, in Application No. JP2018-568204.
U.S. Corrected Notice of Allowance dated Nov. 28, 2022 in U.S. Appl. No. 16/313,860.
U.S. Notice of Allowance dated Dec. 7, 2022 in U.S. Appl. No. 16/739,084.
U.S. Notice of Allowance dated Nov. 18, 2022, in U.S. Appl. No. 16/313,860.
U.S. Appl. No. 18/099,882, Inventors Maharbiz et al., filed Jan. 20, 2023.

\* cited by examiner

Implantable device    tumor hotspot

FIG. 21A
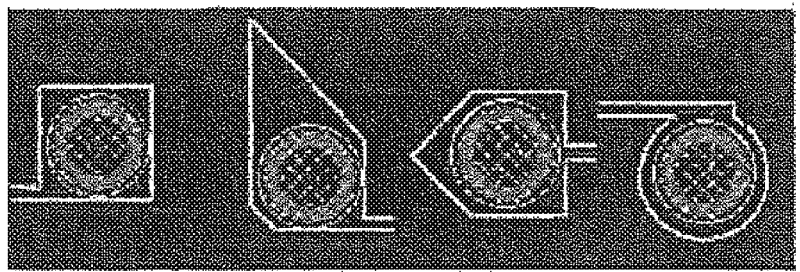
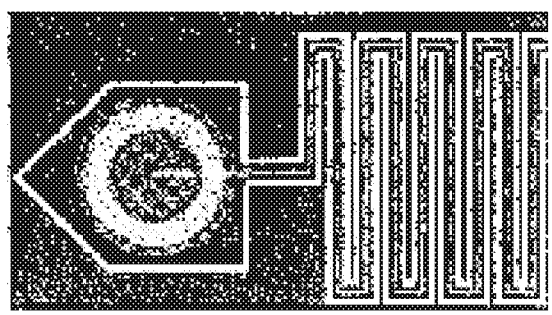
FIG. 21B
FIG. 22
Silver Epoxy Cure Time vs Temperature
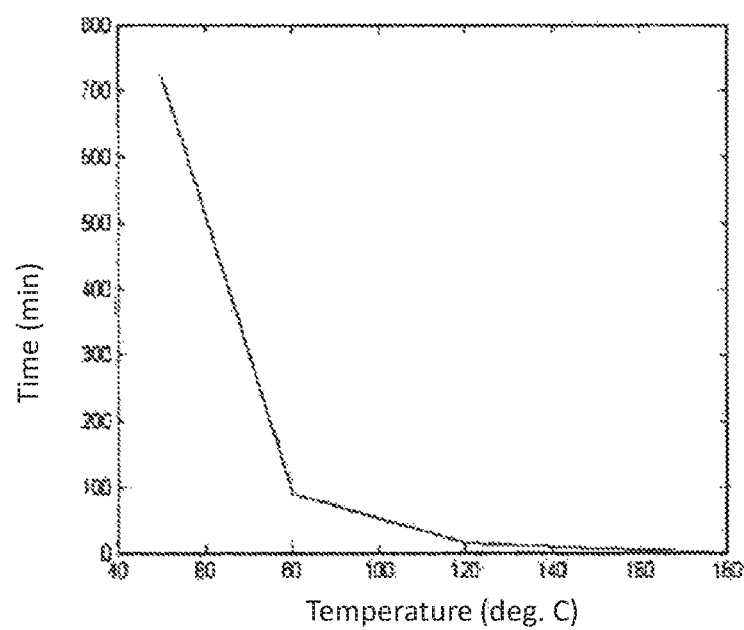

1. Start w/ SCS

2. Spin PI layer

3. PECVD a-SiC

4. RIE openings for electrodes

5. Evaporate ruthenium and plate gold onto electrode sites

6. Die/Piezo attach and wirebond

7. PECVD a-SiC encapsulation

8. RIE emboss topside, remove film from backside

9. Dissolve wafer (TMAH)

27A

27B

27C

IMPLANTS USING ULTRASONIC BACKSCATTER FOR RADIATION DETECTION AND ONCOLOGY

CROSS-REFERENCE TO RELATED APPLICATIONS

This application is a U.S. National Phase Application of International Application No. PCT/US2017/041260, filed Jul. 7, 2017, which claims priority to and the benefit of U.S. Provisional Application No. 62/359,672, filed on Jul. 7, 2016, entitled "NEURAL DUST AND ULTRASONIC BACKSCATTER IMPLANTS AND SYSTEMS, AND APPLICATIONS FOR SUCH SYSTEMS," the disclosure of each of which is incorporated herein by reference in its entirety and for all purposes.

STATEMENT REGARDING FEDERALLY SPONSORED RESEARCH

This invention was made with government support under HR0011-15-2-0006 awarded by the Defense Advanced Research Projects Agency. The government has certain rights in the invention.

TECHNICAL FIELD

The present invention relates to implantable devices for sensing radiation and tumor location in a subject using ultrasonic backscatter.

BACKGROUND

A previously known "neural dust" system includes small, implantable devices (referred to as "neural dust" or "motes"), an implantable ultrasound transceiver that communicates with each of the motes using ultrasound transmissions and backscatter transmissions reflected from the motes, and an external transceiver that communicates wirelessly with the implantable ultrasound transceiver. See Seo et al., *Neural dust: an ultrasonic, low power solution for chronic brain-machine interfaces*, arXiv: 1307.2196v1 (Jul. 8, 2013); Seo et al., *Model validation of untethered, ultrasonic neural dust motes for cortical recording*, Journal of Neuroscience Methods, vol. 224, pp. 114-122, available online Aug. 7, 2014; and Bertrand et al., *Beamforming approaches for untethered, ultrasonic neural dust motes for cortical recording: a simulation study*, IEEE EMBC (August 2014). The neural dust system described in these papers is used for cortical recording (i.e., the recording of brain electrical signals). In that application as shown in the papers, the motes are implanted in the brain tissue (cortex), the ultrasound transceiver (i.e., an "interrogator") is implanted below the dura, on the cortex, and the external transceiver is placed against the head of the patient proximate to where the sub-dural ultrasound transceiver is implanted. This neural dust system is illustrated in FIG. 1.

Despite significant progress in cancer therapeutics, patients are largely incurable if cancer returns after their initial treatment because they develop distant metastatic disease. Unfortunately, the resolution of current imaging platforms (MRI, CT, PET, etc.) is limited, and cannot image micro-metastatic cancers of less than 100,000 to 1,000,000 cells. This lack of resolution stems from 2 factors. (1) Imaging is done from outside the body, inherently limiting sensitivity and resolution by being far from the tumor cells. (2) Current imagers do not rely on molecular identification to distinguish tumor from normal tissue.

Furthermore, despite the continuous improvements in medical physics treatment plan simulations, no method or device exist to accurately measure the actual dose of radiation delivered to a tissue in vivo Improper tissue irradiation can easily occur if there is a shift in the tumor and/or critical organs during the irradiation process (e.g. patient movement). In some cases, this can result in large doses of radiation to be administered to healthy tissue, which is very important to identify in real time for tumors near critical organ areas. This takes on increased importance with the greater utilization of proton therapy, which has greater inaccuracies in dose-prediction due to tissue interactions along the radiation path. Proton therapy has a large Bragg peak, where the majority of the energy is deposited, making both radiation flux and radiation energy measurements important. High-dose per fraction treatments to moving organs, such as the lung, liver and pancreas are more frequently used to treat malignancies in these organs— however ensuring proper dose delivery to these moving organs remains a challenge. Similarly, measuring off-target dose to critical structures such as the spinal cord, are also important to ensure patient safety. What is needed is a device capable of measuring a large range of dose (from direct radiation to scatter radiation) along with relative organ position.

SUMMARY OF THE INVENTION

Described herein are implantable devices configured to detect radiation or the location of a radiation source, such as a radiolabeled cancer or a proton beam. Further described are systems including one or more implantable devices and an interrogator configured to operate said devices. Also described are methods of using the implantable devices, methods of detecting radiation, methods of detecting the location of radiation, and methods for monitoring a subject for the recurrence of a solid cancer.

In some embodiments, there is provided an implantable device, comprising a radiation-sensitive transistor configured to modulate a current as a function of radiation exposure to the transistor; and an ultrasonic device comprising an ultrasonic transducer configured to emit an ultrasonic backscatter that encodes the radiation exposure to the transistor. In some embodiments, the modulated current flows through the ultrasonic transducer. In some embodiments, the ultrasonic device comprises an integrated circuit configured to detect the current modulated by the radiation-sensitive transistor and transmit a signal encoding the exposure of the transistor to radiation to the ultrasonic transducer. In some embodiments of the implantable device, the radiation-sensitive transistor comprises silicon. In some embodiments, the radiation is proton radiation, alpha particles, beta particles, or gamma-rays.

In some embodiments, there is provided an implantable device, comprising a radiation-sensitive diode configured to generate an electrical signal upon encountering radiation; an integrated circuit configured to receive the electrical signal and modulate a current based on the received electrical signal; and an ultrasonic transducer configured to emit an ultrasonic backscatter based on the modulated current encoding information relating to the encountered radiation. In some embodiments, the magnitude of the electrical signal is based on the energy of the encountered radiation. In some embodiments, the radiation-sensitive diode is part of an array comprising a plurality of pixels, each pixel comprising a radiation-sensitive diode configured to generate an electrical signal upon encountering radiation. In some embodiments, the implantable device comprises two or more arrays comprising a plurality of pixels, each pixel comprising a radiation-sensitive diode configured to generate an electrical signal upon encountering radiation. In some embodiments, the arrays in the plurality of arrays are stacked. In some embodiments, the arrays in the plurality of arrays are separated by about 1 mm or less. In some embodiments, each pixel within the array is assigned a unique address.

In some embodiments, the implantable device is configured to determine a directional vector for the encountered radiation. In some embodiments, the implantable device is configured to determine a location of origin of the encountered radiation. In some embodiments, the location of origin is a radiolabeled cell, a radiolabeled cluster of cells, a radiolabeled molecule, or a radiation beam. In some embodiments, the location of origin is a radiolabeled cancer. In some embodiments, the location of origin is radiolabeled using a radiolabeled molecular probe. In some embodiments, the molecular probe comprises an antibody, an antibody mimetic, or a nucleic acid. In some embodiments, the molecular probe is radiolabeled using phosphorus-32 (P-32) or fluorine-18 (F-18).

In some embodiments, the implantable device is configured to filter radiation below a predetermined energy threshold. In some embodiments, the radiation is filtered based on the magnitude of the electrical signal generated by the radiation sensitive diode upon encountering the radiation. In some embodiments, the implantable device comprises three or more arrays comprising a plurality of pixels comprising a radiation-sensitive diode, and wherein the radiation is filtered based on a changed directional vector between the three or more arrays.

In some embodiments of the implantable device, the radiation comprises protons, beta particles, alpha particles, or gamma waves.

In some embodiments, the implantable device comprises a memory configured to store information related to the encountered radiation.

In some embodiments, the implantable device comprises a clock, and wherein the information related to the encountered radiation comprises information related to the time the radiation-sensitive diode encountered the radiation.

In some embodiments of the implantable device, the diode is covered by a scintillator material.

In some embodiments of any of the implantable devices described above, the ultrasonic transducer is configured to receive ultrasonic waves that power the implantable device. In some embodiments, the ultrasonic transducer is configured to receive ultrasonic waves from an interrogator comprising one or more ultrasonic transducers. In some embodiments, the ultrasonic transducer is a bulk piezoelectric transducer, a piezoelectric micro-machined ultrasonic transducer (PMUT), or a capacitive micro-machined ultrasonic transducer (CMUT).

In some embodiments, the implantable device is about 5 mm or less in length in the longest dimension. In some embodiments, the implantable device has a volume of about 5 mm$^3$ or smaller.

In some embodiments, the implantable device is implanted in a subject. In some embodiments, the subject is a human.

In some embodiments of the implantable device, the integrated circuit comprises a power circuit. In some embodiments, the integrated circuit comprises a modulation circuit. In some embodiments, the integrated circuit comprises an analog-to-digital converter (ADC). In some embodiments, the integrated circuit comprises a digital circuit. In some embodiments, the digital circuit is configured to operate the modulation circuit. In some embodiments, the digital circuit is configured to transmit a digitized signal to the modulation circuit, wherein the digitized signal is based on detected radiation.

In some embodiments, the implanted device is at least partially encapsulated by a biocompatible material.

In some embodiments, the implantable device further comprises a non-responsive reflector.

Also provided herein is a system comprising one or more implantable devices described above and an interrogator comprising one or more ultrasonic transducers configured to transmit ultrasonic waves to the one or more implantable devices or receive ultrasonic backscatter from the one or more implantable devices. In some embodiments, the system comprises a plurality of implantable devices. In some embodiments, the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator is configured to transit ultrasonic waves to the plurality of implantable devices or receive ultrasonic backscatter from the plurality of implantable devices using time division multiplexing, spatial multiplexing, or frequency multiplexing. In some embodiments, the interrogator is configured to be wearable by a subject.

In some embodiments, there is provided herein a computer system, comprising one or more processors; and non-transitory computer-readable storage medium storing one or more programs configured to be executed by the one or more processors, the one or more programs comprising instructions for determining an amount of radiation exposed to one or more implantable devices between a first time point and a second time point based on ultrasonic backscatter emitted by the one or more implantable devices at the first time point and the second time point.

Also provided herein is a computer system, comprising one or more processors; and a non-transitory computer-readable storage medium storing one or more programs configured to be executed by the one or more processors, the one or more programs comprising instructions for determining a location of a radiation source relative to one or more implantable devices based on ultrasonic backscatter emitted by the one or more implantable devices. In some embodiments, the one or more programs comprise instructions for determining a plurality of directional vectors for a plurality of radiation particles or waves based on the ultrasonic backscatter emitted by the one or more implantable devices; and determining the location of the radiation source based on the plurality of directional vectors. In some embodiments, the radiation source is a radiolabeled cancer.

In some embodiments of any one of the computer systems described above, the computer system comprises one or more ultrasonic transducers. In some embodiments, the one or more programs comprises instructions for operating the one or more ultrasonic transducers.

In some embodiments of the computer system, the one or more programs comprise instructions for determining a location for the one or more implantable devices relative to the one or more ultrasonic transducers, or movement of the one or more implantable devices, based on the ultrasonic backscatter emitted by the one or more implantable devices. In some embodiments, the one or more programs comprise instructions for determining angular or lateral movement of the one or more implantable devices based on the ultrasonic backscatter emitted by the one or more implantable devices.

Also described herein is a method of detecting radiation, comprising receiving ultrasonic waves that power one or more implantable devices comprising an ultrasonic transducer and a radiation-sensitive transistor; converting energy from the ultrasonic waves into an electrical current; exposing the radiation-sensitive transistor to an amount of radiation; modulating the electrical current as a function of radiation exposed to the radiation-sensitive transistor; transducing the modulated electrical current into an ultrasonic backscatter that encodes the amount of radiation exposed to the radiation-sensitive transistor; and emitting the ultrasonic backscatter to an interrogator comprising one or more transducers configured to receive the ultrasonic backscatter. In some embodiments, the electrical current flows through an integrated circuit, the method further comprising flowing a second electrical current through the integrated circuit and the radiation-sensitive transistor; modulating the second electrical current as a function of radiation exposed to the radiation-sensitive transistor; modulating the electrical current transduced into the ultrasonic backscatter based on the modulated second electrical current.

In some embodiments, there is provided herein a method of treating a solid cancer in a subject, comprising targeting the cancer with radiation; and monitoring targeted radiation exposure, comprising transmitting ultrasonic waves from an interrogator comprising one or more ultrasonic transducers to one or more implantable devices comprising an ultrasonic transducer and a radiation-sensitive transistor implanted proximal to the cancer, and receiving from the one or more implantable devices ultrasonic backscatter encoding an amount of radiation exposed to the one or more implantable devices. In some embodiments, the method comprises determining the location or direction of origin of the radiation. In some embodiments, the one or more implantable devices are located adjacent to, on, or within the cancer. In some embodiments, the method comprises re-targeting the cancer with the radiation based on the amount of radiation exposed to the one or more implantable devices. In some embodiments, the method comprises determining an amount of radiation exposed to the radiation-sensitive transistor between a first time point and a second time point. In some embodiments, the method comprises determining an amount of radiation exposed to the radiation-sensitive transistor between the first time point and a third time point. In some embodiments, the method comprises determining a rate of radiation exposed to the radiation-sensitive transistor.

Further described herein is a method of detecting radiation, comprising receiving ultrasonic waves that power one or more implantable devices comprising an ultrasonic transducer, an integrated circuit, and a radiation-sensitive diode configured to generate a signal upon encountering radiation; converting energy from the ultrasonic waves into an electrical current that flows through the integrated circuit; exposing the diode to a radiation particle or wave from a radiation source; transmitting a signal to the integrated circuit indicating exposure of the diode to the radiation particle or wave; modulating the electrical current based the signal transmitted to the integrated circuit; transducing the modulated electrical current into an ultrasonic backscatter that encodes the radiation exposure; and emitting the ultrasonic backscatter to an interrogator comprising one or more transducer configured to receive the ultrasonic backscatter. In some embodiments, the diode is within an array comprising a plurality of pixels, each pixel comprising a radiation-sensitive diode configured to generate a signal upon encountering radiation. In some embodiments, the signal transmitted to the integrated circuit indicating exposure of the pixel to radiation comprises a pixel address.

Further described herein is a method of detecting radiation, comprising receiving ultrasonic waves that power one or more implantable devices comprising an ultrasonic transducer, an integrated circuit, and two or more arrays comprising a plurality of pixels, each pixel comprising a radiation-sensitive diode configured to generate a signal upon encountering radiation; converting energy from the ultrasonic waves into an electrical current that flows through the integrated circuit; exposing one or more of the pixels to a radiation particle or wave from a radiation source; transmitting a signal to the integrated circuit indicating exposure of the one or more of the pixels to the radiation particle or wave; modulating the electrical current based the signal transmitted to the integrated circuit; transducing the modulated electrical current into an ultrasonic backscatter that encodes the radiation exposure; and emitting the ultrasonic backscatter to an interrogator comprising one or more transducer configured to receive the ultrasonic backscatter. In some embodiments, the signal transmitted to the integrated circuit indicating exposure of the one or more pixels to the radiation particle or wave comprises a pixel address. In some embodiments, a first pixel on a first array and a second pixel on a second array are exposed to the same radiation particle or wave. In some embodiments, the method comprises determining a directional vector for the radiation particle or wave. In some embodiments, the ultrasonic backscatter encodes the directional vector of the radiation particle or wave. In some embodiments, the method comprises determining a plurality of directional vectors for a plurality of radiation particles or waves. In some embodiments, the method comprises determining the location of the radiation source relative to the implantable device based on the plurality of directional vectors. In some embodiments, the ultrasonic backscatter encodes the pixel address. In some embodiments, the ultrasonic backscatter encodes the location of the radiation source relative to the implantable device.

In some embodiments, there is provided herein a method of monitoring a subject for recurrence of a solid cancer, comprising administering to the subject a radiolabeled molecular probe that emits a radiation particle or wave and that specifically binds to the solid cancer; transmitting ultrasonic waves from an interrogator comprising one or more ultrasonic transducers to one or more implantable devices comprising an ultrasonic transducer and two or more stacked arrays, each array comprising a plurality of pixels comprising a radiation-sensitive diode configured to generate an electrical signal upon encountering the radiation particle or wave; and receiving from the one or more implantable devices ultrasonic backscatter that encodes information related to the encountered radiation particle or wave. In some embodiments, the one or more implantable devices are powered by the ultrasonic waves transmitted form the interrogator. In some embodiments, the radiation particle counters a first pixel on a first array and a second pixel on a second array, and wherein the information related to the encountered radiation comprises a first pixel address of a first pixel that encountered the radiation particle or wave, and a second pixel address of a second pixel that encountered the radiation particle or wave. In some embodiments, the method comprises determining a direction vector of the radiation particle or wave emitted from the solid cancer. In some embodiments, the information related to the encountered radiation particle or wave comprises a directional vector of the radiation particle or wave emitted from the solid cancer. In some embodiments, the method comprises determining the location of the solid cancer. In some embodiments, the information related to the encountered radiation particle or wave comprises a location of the solid cancer relative to the one or more implantable devices. In some embodiments, the one or more implantable devices are implanted at or proximal to a location of a previously excised solid cancer. In some embodiments, the method comprises monitoring the movement of the solid cancer over a period of time. In some embodiments, the molecular probe comprises an antibody, an antibody mimetic, or a nucleic acid molecule. In some embodiments, the molecular probe is radiolabeled with phosphorus-32 (P-32) of fluorine-18 (F-18). In some embodiments, the information related to the encountered radiation particle or wave comprises information related to the time the radiation particle or wave that encountered the diode. In some embodiments, the method comprises determining a first radiation particle or wave and a second radiation particle or wave that originated from the same location based on the information related to the time the first radiation particle or wave encountered a first diode on a first implantable device and information related to the time the second radiation particle or wave that encountered a second diode on a second implantable device. In some embodiments, the first radiation particle or wave is a first photon, and the second radiation particle or wave is a second photon, wherein the first photon and the second photon originated from a positron. In some embodiments, the solid cancer has a radius of about 500 µm or less.

In some embodiments of the methods described above, the method comprises filtering background radiation particles or waves with an energy below a predetermined threshold.

In some embodiments of the methods described above, the radiation or the radiation particles or waves comprise protons, alpha particles, beta particles, or gamma waves.

In some embodiments of the methods described above, the radiation source comprises phosphorus-32 (P-32) or fluorine-18 (F-18).

In some embodiments of the methods described above, the method comprises receiving the ultrasonic backscatter using the interrogator.

In some embodiments of the methods described above, the method comprises transmitting the ultrasonic waves using the interrogator configured to transmit the ultrasonic waves.

In some embodiments of the methods described above, the method implanting the one or more implantable devices.

In some embodiments of the methods described above, the method determining a location or movement of the one or more implantable devices.

In some embodiments of the methods described above, the radiation comprises a proton beam.

In some embodiments of the methods described above, the radiation source is a radiolabeled cluster of cells. In some embodiments, the cluster of cells is a solid cancer. In some embodiments, the solid cancer is in a subject. In some embodiments, the subject is a human.

In some embodiments of the methods described above, the one or more implantable devices are implanted in a human.

BRIEF DESCRIPTION OF THE FIGURES

In FIG. 15A shows a previous cancer treatment paradigm for pancreas and prostate cancer. After resection, CT or MRI imaging is done to monitor the body for signs of recurrence. Unfortunately, even if a blood marker like PSA is elevated, no spatial localization is provided and microscopic disease cannot be seen until it spreads and grows, resulting in metastatic disease and an incurable patient. In FIG. 15B, the proposed platform utilizes sensors placed in the tumor bed. At each regular surveillance scan, a radiolabeled target agent is injected; binding to the tumor cells in the body and the sensors will detect the local radiation signal. Power to the sensor and data to the clinician will be transmitted via ultrasound. Identifying the exact location of microscopic recurrent disease can enable focal curative therapy before the cancer spreads.

FIG. 21A shows different geometries of vias used to connect components of the implantable device. FIG. 21B shows a serpentine trace configuration for deformable interconnects.

FIG. 22 shows the relationship between time and temperature for curing silver epoxy, an exemplary material for attaching wirebonds during the manufacture of the implantable device.

DETAILED DESCRIPTION OF THE INVENTION

Figure 1:
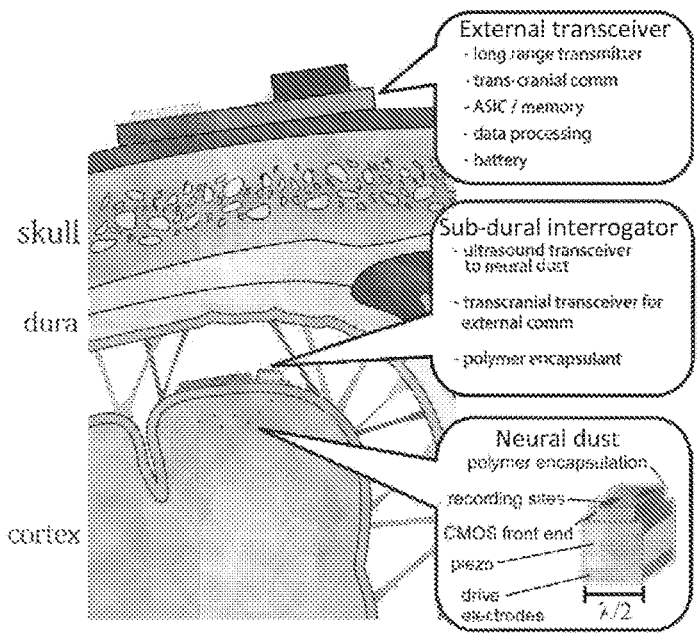
FIG. 1 is a schematic of a neural dust system, including an external transceiver, a sub-dural interrogator, and a neural dust mote, as described in Seo et al., *Neural dust: an ultrasonic, low power solution for chronic brain-machine interfaces*, arXiv: 1307.2196v1 (Jul. 8, 2013).

It has been found that ultrasonic power harvesting and backscatter communication can be used to wirelessly power and communicate with implantable devices (including CMOS implants). In one aspect, present disclosure describes the use of implantable devices in the field of radiation oncology. In some embodiments, the implantable device is an implantable dosimeter for localized organ dosimetry (also referred to as "Dosimetry Dust"). Dosimetry dust can be used, for example, with proton beam therapy. The implantable device can detect protons, for example a large dose up to ~60Gy. In some embodiments, the implantable device is useful for the detection of cells within a body, such as recurrent cancers (also referred to as "Oncology Dust). The implantable device can use, for example, beta radiation as a sensing modality, and is designed to detect small beta radiation signals amidst a large amount of background radiation. The Oncology Dust can be useful for determining the location of a radiolabeled cell (such as a cancer), or for other intra-body imaging (such as determining the location of other radiolabeled molecules such as nucleic acids or proteins). For example the Oncology Dust can be useful for determining the presence or location of cells or other substance at a location by radiolabeling the cells or substances and detecting emitted radiation. As an example, tumor infiltrating lymphocytes can be detected at a location by binding a radiolabel to the tumor infiltrating lymphocytes and detecting radiation at the location. Imaging from within the patient using the implantable device can achieve orders of magnitude greater sensitivity and spatial location, allowing for treatment at early stages of microscopic disease.

Although there have been notable advances in miniaturization of CMOS devices for radiation detection, the current state of the art in implantable dosimetry uses RF as a communication modality. Limitations in RF technologies must still be investigated when used for implantable radiation detectors in vivo, and there is still exists a challenge to wirelessly communicate through tissue that must be addressed. The implantable device described herein utilizes ultrasound as the communication platform as an alternative to RF modalities. The overall power transmission efficiency in a piezoelectric transducer is higher for ultrasound compared to RF as the receiver size is scaled, and position the receiver farther away from an ultrasound interrogator. This indicates that we have better energy harvesting in vivo for an ultrasound-based device, allowing us to have deeper depth of device penetration in tissue and a larger backscattered signal than the RF device alternatives.

The size of the implantable device is aggressively miniaturized for radiation detection. In some embodiments, the system described herein has the potential to be scaled to tens of microns, allowing for extremely non-invasive, long-term implantable devices.

The implantable device described herein includes a miniaturized ultrasonic transducer (such as a miniaturized piezoelectric transducer). The miniaturized ultrasonic transducer receives ultrasonic energy from an interrogator (which may be external or implanted), which powers the implantable device. The interrogator includes a transmitter and a receiver (which may be integrated into a combined transceiver), and the transmitter and the receiver may be on the same component or different components. Mechanical energy from the ultrasonic waves transmitted by the interrogator vibrates the miniaturized ultrasonic transducer on the implantable device, which generates an electrical current. The current flowing through the miniaturized ultrasonic transducer is modulated by the electrical circuitry in the implantable device based on detected radiation, and the modulated current returns to the miniaturized ultrasonic transducer. The miniaturized ultrasonic transducer emits an ultrasonic backscatter communicating information indicative of the sensed radiation, which is detected by the receiver components of the interrogator.

In some embodiments, the implantable device includes a radiation-sensitive element (such as a transistor, a diode, or a memory cell). A radiation-sensitive transistor modulates current based on the exposure of the transistor to radiation over time. This device can be useful, for example, to monitor localized radiation exposure in a subject. For example, proton beam therapies can be used to irradiate a cancer in a subject. By placing an implantable device adjacent to the tumor, it is possible to monitor the amount of off-target radiation exposure. A radiation sensitive diode can detect radiation and produce a transient electrical current to signal the detected radiation. The diode can also relay information about the energy of the encountered radiation particle or wave based on the transient current.

In some embodiments, the implantable device includes one or more arrays comprising a plurality of radiation-sensitive pixels (with each pixel including a radiation-sensitive diode). When a radiation particle contacts a pixel in the array, a transient current is generated. The array signals the location within the array of the pixel contacted with the radiation particle to an application specific integrated circuit (ASIC) located on the implantable device. By including two or more arrays on the implantable device, it is possible to determine the originating location of the radiation particle or wave that excites the diode. The radiation source can be, for example, a radiation beam (which can be used, for example, to treat a cancer) or a radiolabeled cell or molecule (such as a cancer cell or tumor marker).

A significant advantage of the implantable device is the ability to detect radiation in deep tissue while being wirelessly powered, and wirelessly transmit information relating the detected radiation to an interrogator, which can be external or relay the information to an external component. Thus, the implantable devices can remain in a subject for an extended period of time without needing to charge a battery or retrieve information stored on the device. These advantages, in turn, allow the device to be smaller and less expensive to manufacture. In another advantage, use of ultrasound allows for the relative time for data communication to be related to distance, which can aid in determining location or movement of the implantable device in real time.

Electromagnetic (EM) power transfer is not practical for powering small implantable devices due to power attenuation through tissue and the relatively large apertures (e.g. antennas or coils) required to capture such energy. See, for example, Seo et al., *Neural dust: an ultrasonic, low power solution for chronic brain-machine interfaces*, arXiv paper (July 2013). Use of EM to supply sufficient power to an implanted device would either require a shallow depth of the implant or would require excessive heating of the tissue to pass the EM waves through the tissue to reach the implantable device. In contrast to EM, ultrasonic power transfer provides low power attenuation in tissue due to the relatively low absorption of ultrasonic energy by tissue and the shorter wavelength of the ultrasonic waves (as compared to electromagnetic waves).

Ultrasonic transducers have found application in various disciplines including imaging, high intensity focused ultrasound (HIFU), nondestructive testing of materials, communication and power delivery through steel walls, underwater communications, transcutaneous power delivery, and energy harvesting. See, e.g., Ishida et al., *Insole Pedometer with Piezoelectric Energy Harvester and 2 V Organic Circuits*, IEEE J. Solid-State Circuits, vol. 48, no. 1, pp. 255-264

(2013); Wong et al., *Advantages of Capacitive Micromachined Ultrasonics Transducers (CMUTs) for High Intensity Focused Ultrasound (HIFU)*, IEEE Ultrasonics Symposium, pp. 1313-1316 (2007); Ozeri et al., *Ultrasonic Transcutaneous Energy Transfer for Powering Implanted Devices*, Ultrasonics, vol. 50, no. 6, pp. 556-566 (2010); and Richards et al., *Efficiency of Energy Conversion for Devices Containing a Piezoelectric Component*, J. Micromech. Microeng., vol. 14, pp. 717-721 (2004). Unlike electromagnetics, using ultrasound as an energy transmission modality never entered into widespread consumer application and was often overlooked because the efficiency of electromagnetics for short distances and large apertures is superior. However, at the scale of the implantable devices discussed herein and in tissue, the low acoustic velocity allows operation at dramatically lower frequencies, and the acoustic loss in tissue is generally substantially smaller than the attenuation of electromagnetics in tissue.

The relatively low acoustic velocity of ultrasound results in substantially reduced wavelength compared to EM. Thus, for the same transmission distance, ultrasonic systems are much more likely to operate in the far-field, and hence obtain larger spatial coverage than an EM transmitter. Further, the acoustic loss in tissue is fundamentally smaller than the attenuation of electromagnetics in tissue because acoustic transmission relies on compression and rarefaction of the tissue rather than time-varying electric/magnetic fields that generate displacement currents on the surface of the tissue.

It has been found that ultrasonic waves can be used to power and communicate with miniaturized implantable devices containing a miniaturized ultrasonic transducer (such as a bulk piezoelectric, a PMUT, or a CMUT). The implantable devices are able to detect radiation, and emit ultrasonic backscatter waves that encode information relating to the detected radiation. The effects of radiation on silicon have been previously described, and it has been demonstrated that electron-hole pairs (EHP) can be generated in a depletion region of silicon-based MOS devices. It has been demonstrated that electron-hole pairs (EHP) can be generated in a depletion region of silicon-based MOS devices. The generation of EHP is CMOS devices can be used to generate a current, which can be used to modulate the backscattered ultrasound signal, including a modulated amplitude. By correlating a known received dose to the backscatter changes seen in the backscatter signal, the device can be calibrated to respond to varying radiation doses.

The implantable devices described herein can be implanted in or used in a subject (i.e., an animal), preferably a vertebrate. In some embodiments, the subject is a mammal. Exemplary subjects include a rodent (such as a mouse, rat, or guinea pig), cat, dog, chicken, pig, cow, horse, sheep, rabbit, etc. In some embodiments, the subject is a human Definitions As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "miniaturized" refers to any material or component about 5 millimeters or less (such as about 4 mm or less, about 3 mm or less, about 2 mm or less, about 1 mm or less, or about 0.5 mm or less) in length in the longest dimension. In certain embodiments, a "miniaturized" material or component has a longest dimension of about 0.1 mm to about 5 mm (such as about 0.2 mm to about 5 mm, about 0.5 mm to about 5 mm, about 1 mm to about 5 mm, about 2 mm to about 5 mm, about 3 mm to about 5 mm, or about 4 mm to about 5 mm) in length. "Miniaturized" can also refer to any material or component with a volume of about 5 $mm^3$ or less (such as about 4 $mm^3$ or less, 3 $mm^3$ or less, 2 $mm^3$ or less, or 1 $mm^3$ or less). In certain embodiments, a "miniaturized" material or component has a volume of about 0.5 $mm^3$ to about 5 $mm^3$, about 1 $mm^3$ to about 5 $mm^3$, about 2 $mm^3$ to about 5 $mm^3$, about 3 $mm^3$ to about 5 $mm^3$, or about 4 $mm^3$ to about 5 $mm^3$.

A "piezoelectric transducer" is a type of ultrasonic transceiver comprising piezoelectric material. The piezoelectric material may be a crystal, a ceramic, a polymer, or any other natural or synthetic piezoelectric material.

A "non-responsive" ultrasonic wave is an ultrasonic wave with a reflectivity independent of a detected signal. A "non-responsive reflector" is a component of an implantable device that reflects ultrasonic waves such that the reflected waveform is independent of the detected signal.

The term "subject" refers to an animal.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features.

The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein. Further, sectional headings are provide for organizational purposes and are not to be considered limiting. Finally, the entire disclosure of the patents and publications referred in this application are hereby incorporated herein by reference for all purposes.

Interrogator

The interrogator can wirelessly communicate with one or more implantable devices using ultrasonic waves, which are used to power and/or operate the implantable device. The interrogator can further receive ultrasonic backscatter from the implantable device, which encodes information indicative of detected radiation. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device. In some embodiments, the transducers in the array can have regular spacing, irregular spacing, or be sparsely placed. In some embodiments the array is flexible. In some embodiments the array is planar, and in some embodiments the array is non-planar.

Figure 2A:
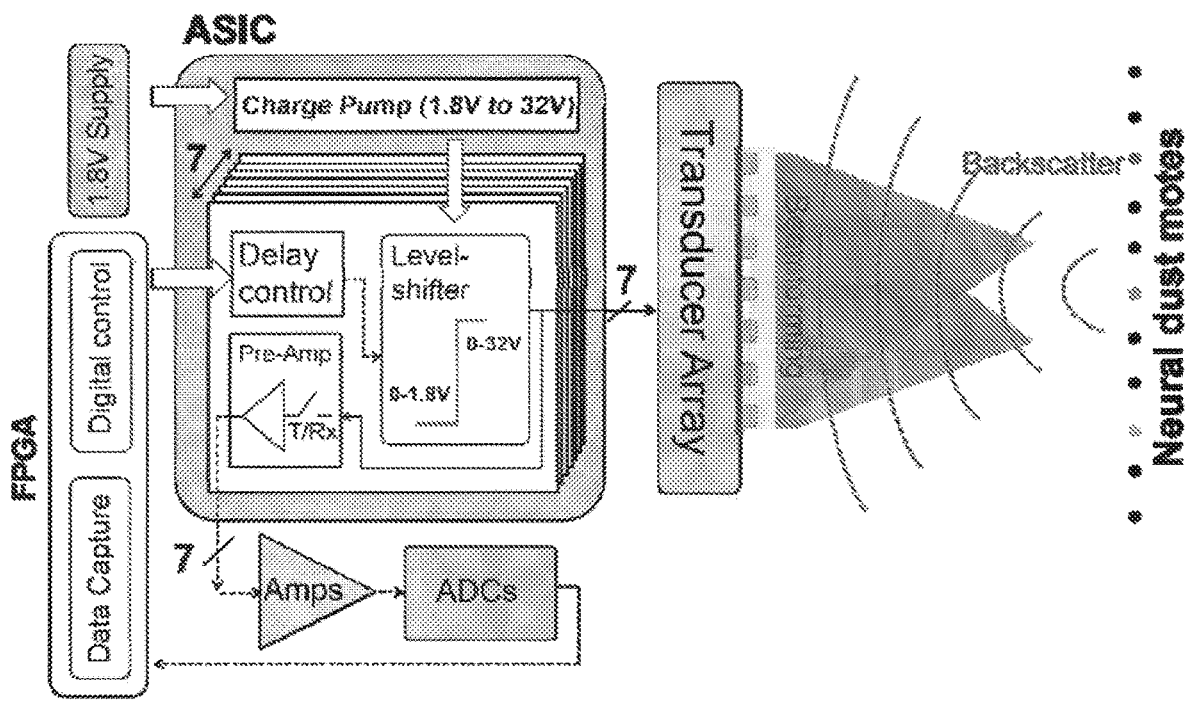
FIG. 2A is a block diagram of an exemplary interrogator for a system described herein. The illustrated interrogator includes an ultrasonic transducer array comprising a plurality of ultrasonic transducers. Each of the ultrasonic transducers in the array is operated by a channel, which includes a switch to alternatively configure the transducer to receive or transmit ultrasonic waves.

An exemplary interrogator is shown in FIG. 2A. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels. The interrogator shown in FIG. 2A illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an ASIC, which includes a channel for each transducer in the transducer array. In some embodiments, the channel includes a switch (indicated in FIG. 2A by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit. In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 2A) to convert a first voltage supplied to the ASIC to a higher second voltage, which is applied to the channel. The channels can be controlled by a controller, such as a digital controller, which operates the delay control. In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier, or a time-gain-controlled variable-gain-amplifier which compensates for tissue loss, and/or a band pass filter is included in the receiving circuit. The ASIC can draw power from a power supply, such as a battery (which is preferred for a wearable embodiment of the interrogator). In the embodiment illustrated in FIG. 2, a 1.8V supply is provided to the ASIC, which is increased by the charge pump to 32V, although any suitable voltage can be used. In some embodiments, the interrogator includes a processor and/or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

Figure 2B:
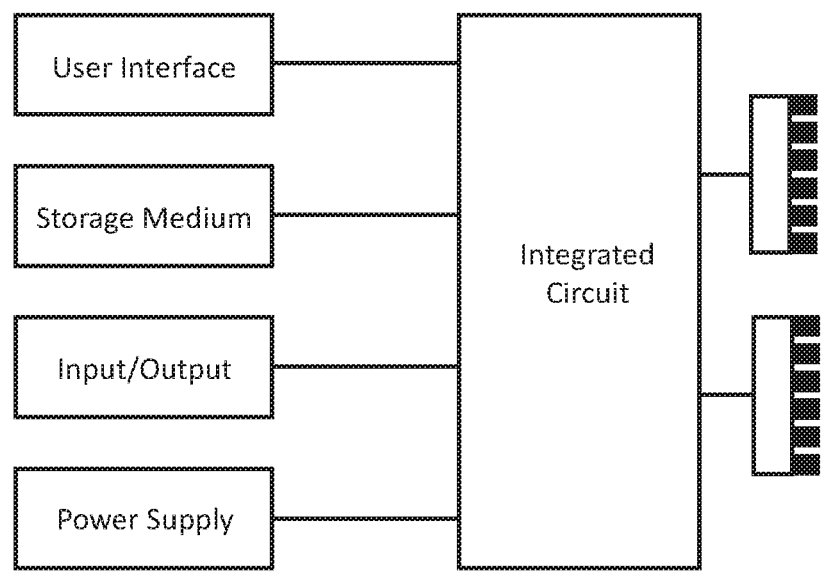
FIG. 2B is a schematic of another exemplary interrogator for a system described herein. The illustrated interrogator includes two ultrasonic transducer arrays, with each ultrasonic transducer array including a plurality of ultrasonic transducers. The interrogator also includes an integrated circuit (which can include a digital circuit, which can include a processor). The integrated circuit is connected to a user interface (which can include a display, keyboard, buttons, etc.), a storage medium (i.e., a non-transitory memory), an input/output (which may be wireless, such as BLUETOOTH® wireless technology), and a power supply (such as a battery).

FIG. 2B illustrates another embodiment of interrogator. As shown in FIG. 2B, the interrogator includes one or more transducers 202. Each transducer 202 is connected to a transmitter/receiver switch 204, which can alternatively configure the transducer to transmit or receive ultrasonic waves. The transmitter/receiver switch is connected to a processor 206 (such as a central processing unit (CPU), a custom dedicated processor ASIC, a field programmable gate array (FPGA), microcontroller unit (MCU), or a graphics processing unit (GPU)). In some embodiments, the interrogator further includes an analog-digital converter (ADC) or digital-to-analog converter (DAC). The interrogator can also include a user interface (such as a display, one or more buttons to control the interrogator, etc.), a memory, a power supply (such as a battery), and/or an input/output port (which may be wired or wireless).

In some embodiments, the interrogator is implantable. An implanted interrogator may be preferred when the implantable devices are implanted in a region blocked by a barrier that does not easily transmit ultrasonic waves. For example, the interrogator can be implanted subcranially, either subdurally or supradurally. A subcranial interrogator can communicate with implantable devices that are implanted in the brain. Since ultrasonic waves are impeded by the skull, the implanted subcranial interrogator allows for communication with the implantable devices implanted in the brain. In another example, an implantable interrogator can be implanted as part of, behind or within another implanted device, such as a bone plate. The implanted interrogator can communicate with an external device, for example by EM or RF signals.

Figure 3A:
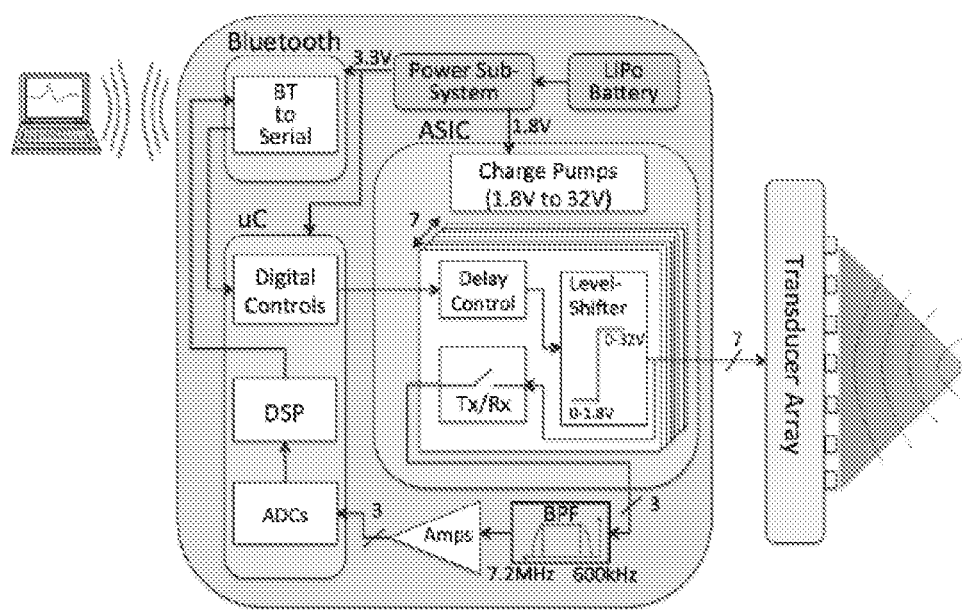
FIG. 3A shows a block diagram of an exemplary interrogator that can be worn by a subject. The interrogator includes a wireless communication system (BLUETOOTH® wireless technology radio, in the illustration), which can be used to communicate with a computer system.
Figure 3B:
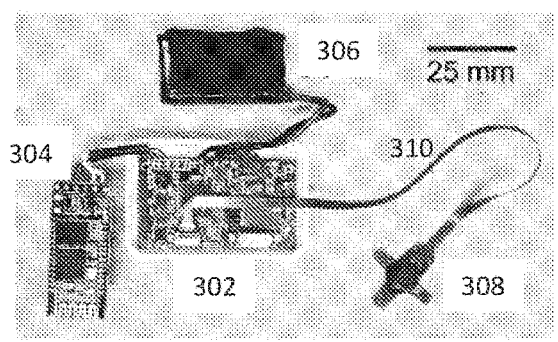
FIG. 3B shows an exploded view of a wearable interrogator. The interrogator includes a battery, a wireless communication system, and a transducer array.
Figure 3C:
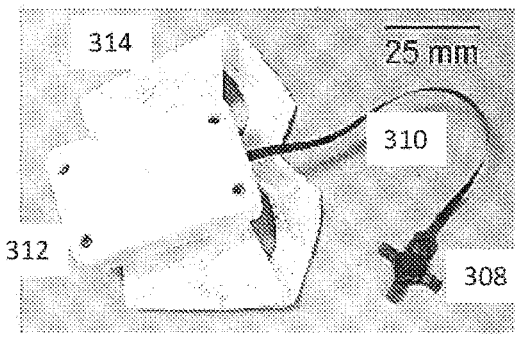
FIG. 3C shows the wearable interrogator shown in FIG. 3B fully assembled with a harness for attachment to a subject.
Figure 3D:
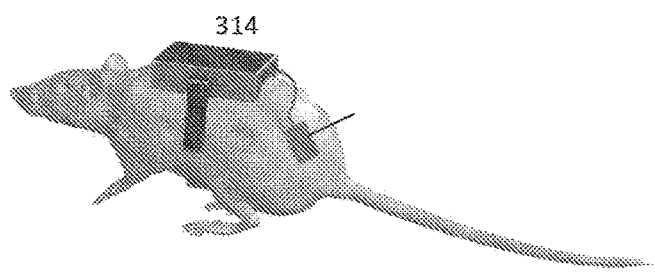
FIG. 3D illustrates the wearable interrogator attached a subject, namely a rodent (although could be any other animal, such as a human, dog, cat, horse, cow, pig, sheep, goat, chicken, monkey, rat or mouse). The interrogator includes a transducer array, which is fixed to the body of the subject by an adhesive.
Figure 3E:
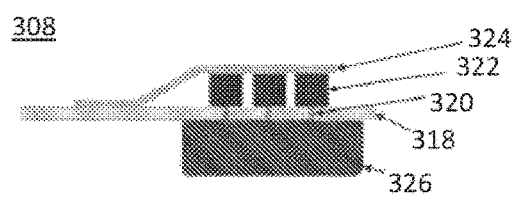
FIG. 3E illustrates a cross-section of the transducer array of the interrogator shown in FIGS. 3A-D.

In some embodiments, the interrogator is external (i.e., not implanted). By way of example, the external interrogator can be a wearable, which may be fixed to the body by a strap or adhesive. In another example, the external interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator. FIG. 3A-E shows an example of a wearable external interrogator. FIG. 3A shows a block diagram of the interrogator, which includes a transducer array comprising a plurality of transducers, an ASIC comprising a channel for each transducer in the transducer array, a battery (lithium polymer (LiPo) battery, in the illustrated example), and a wireless communication system (such as a BLUETOOTH® wireless technology system). FIG. 3B illustrates an exploded view of a wearable interrogator, including a printed circuit board (PCB) 302, which includes the ASIC, a wireless communication system 304, a battery 306, an ultrasonic transducer array 308, and a wire 310 tethering the ultrasonic transducer array 308 to the ASIC. FIG. 3C shows the wearable interrogator 312 shown in FIG. 3B with a harness 314, which can be used to attach the interrogator to a subject. FIG. 3D shows the assembled interrogator 316 attached to a subject, with the transducer array 308 attached at a first location, and the rest of the interrogator attached to a second location. FIG. 3E shows a cross-section schematic of an exemplary ultrasonic transducer array 308, which includes a circuit board 318, vias 320 attaching each transducer 322 to the circuit board 318, a metalized polyester film 324, and an absorptive backing layer 326. The metalized polyester film 324 can provide a common ground and acoustic matching for the transducers, while the absorptive backing layer 326 (such as tungsten powder filled polyurethane) can reduce ringing of the individual transducers.

The specific design of the transducer array depends on the desired penetration depth, aperture size, and the size of individual the transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and $\lambda$ is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Communication Between an Implantable Device and an Interrogator

The implantable device and the interrogator wirelessly communicate with each other using ultrasonic waves. The implantable device receives ultrasonic waves from the interrogator through a miniaturized ultrasonic transducer on the implantable device. Vibrations of the miniaturized ultrasonic transducer on the implantable device generate a voltage across the electric terminals of the transducer and current flows through the device, including, if present, the ASIC. Depending on the radiation detected by the sensor (e.g., the radiation-sensitive transistor or other element, such as a diode), information relating to the detected radiation can alter the current, which in turns modulates the backscatter from the miniaturized ultrasonic transducer. The information relating to the detected radiation can be, for example, the presence or absence of radiation, lifetime radiation exposure, or trajectory of a radiation particle. The system (including the optional ASIC) presents an electrical impedance to the electric terminals on the transducer. If this impedance changes, the mechanical impedance of the transducer (as seen from outside the device) changes, resulting in changes in backscatter. Thus, the sensor system modulates the electrical impedance presented to the transducer to effect backscatter communication. The backscatter is then received by an external ultrasonic transceiver (which may be the same or different from the external ultrasonic transceiver that transmitted the initial ultrasonic waves). The information from the detected radiation can thus be encoded by changes in amplitude, frequency, or phase of the backscattered ultrasound waves.

Figure 4:
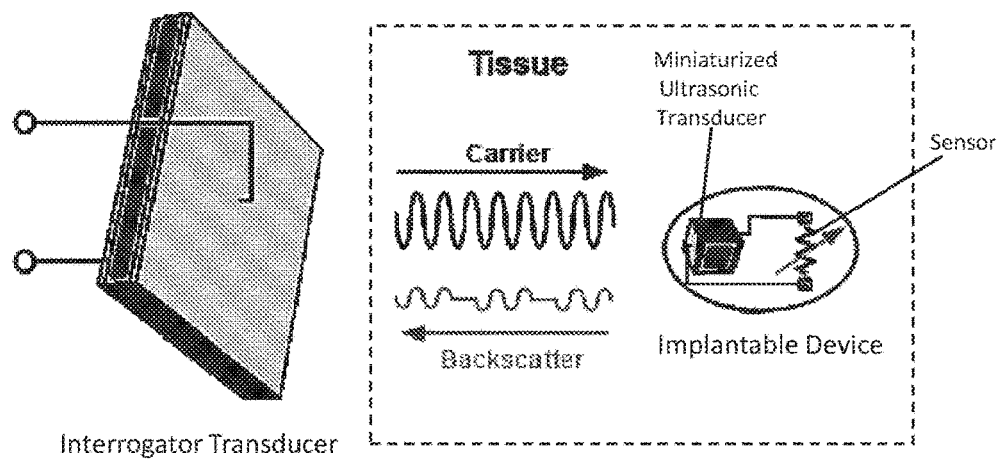
FIG. 4 provides a schematic showing the communication between a transducer from an interrogator and an implantable device having a miniaturized ultrasonic transducer. The interrogator transmits ultrasonic waves to the implantable device, and the miniaturized ultrasonic transducer emits ultrasonic backscatter modulated by the sensor. The backscatter is then received by the interrogator.

FIG. 4 illustrates an interrogator in communication with an implantable device. The external ultrasonic transceiver emits ultrasonic waves ("carrier waves"), which can pass through tissue. The carrier waves cause mechanical vibrations on the miniaturized ultrasonic transducer (e.g., a miniaturized bulk piezoelectric transducer, a PMUT, or a CMUT). A voltage across the miniaturized ultrasonic transducer is generated, which imparts a current flowing through a sensor on the implantable device. In some embodiments, the implantable device includes an ASIC, and current flows from the miniaturized ultrasonic transducer, through the ASIC, to the radiation detector, back to the ASIC, and returns to the miniaturized ultrasonic transducer. The current flowing through the miniaturized ultrasonic transducer causes the transducer on the implantable device to emit backscatter ultrasonic waves. The current flowing through the miniaturized ultrasonic transducer changes the amplitude, frequency, and/or phase of the backscatter ultrasonic wave emitted or reflected from the ultrasonic transducer. Since the detected radiation affects the current returning to the ASIC and/or the miniaturized ultrasonic transducer, the backscatter waves encode information relating to the detected radiation. The backscatter waves can be detected by the interrogator, and can be deciphered to determine information regarding the detected radiation or location of the radiation.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. In some embodiments, the pulses are about 200 nanoseconds (ns) to about 1000 ns in length (such as about 300 ns to about 800 ns in length, about 400 ns to about 600 ns in length, or about 540 ns in length). In some embodiments, the pulses are about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the pulses are about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are separated by a dwell time. In some embodiments, the dwell time is about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the dwell time is about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are square, rectangular, triangular, sawtooth, or sinusoidal. In some embodiments, the pulses output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period. In some embodiments, the one or more pulses in the cycle includes about 1 to about 10 pulses (such as about 2 to about 8, or about 4 to about 7, or about 6) pulses of ultrasonic waves in any given cycle. In some embodiments, the one or more pulses in the cycle includes about 1 or more, 2 or more, 4 or more, 6 or more, 8 or more, or 10 or more pulses of ultrasonic waves in any given cycle. In some embodiments, the one or more pulses in the cycle includes about 20 or fewer, about 15 or fewer, about 10 or fewer, about 8 or fewer, or about 6 or fewer pulses in the cycle. The pulse cycle can be regularly repeated, for example every about 50 microseconds (μs) to about 300 μs (such as about every 75 μs to about 200 μs, or every about 100 μs) during operation. In some embodiments, the cycle is reaped every 50 μs or longer, every 100 μs or longer, every 150 μs or longer, every 200 μs or longer, every 250 μs or longer, or every 300 μs or longer. In some embodiments, the cycle is repeated every 300 μs or sooner, every 250 μs or sooner, every 200 μs or sooner, every 150 μs or sooner, or every 100 μs or sooner. The cycle frequency can set, for example, based on the distance between the interrogator and the implantable device and/or the speed at which the transducer can toggle between the transmitting and receiving modes.

Figure 5:
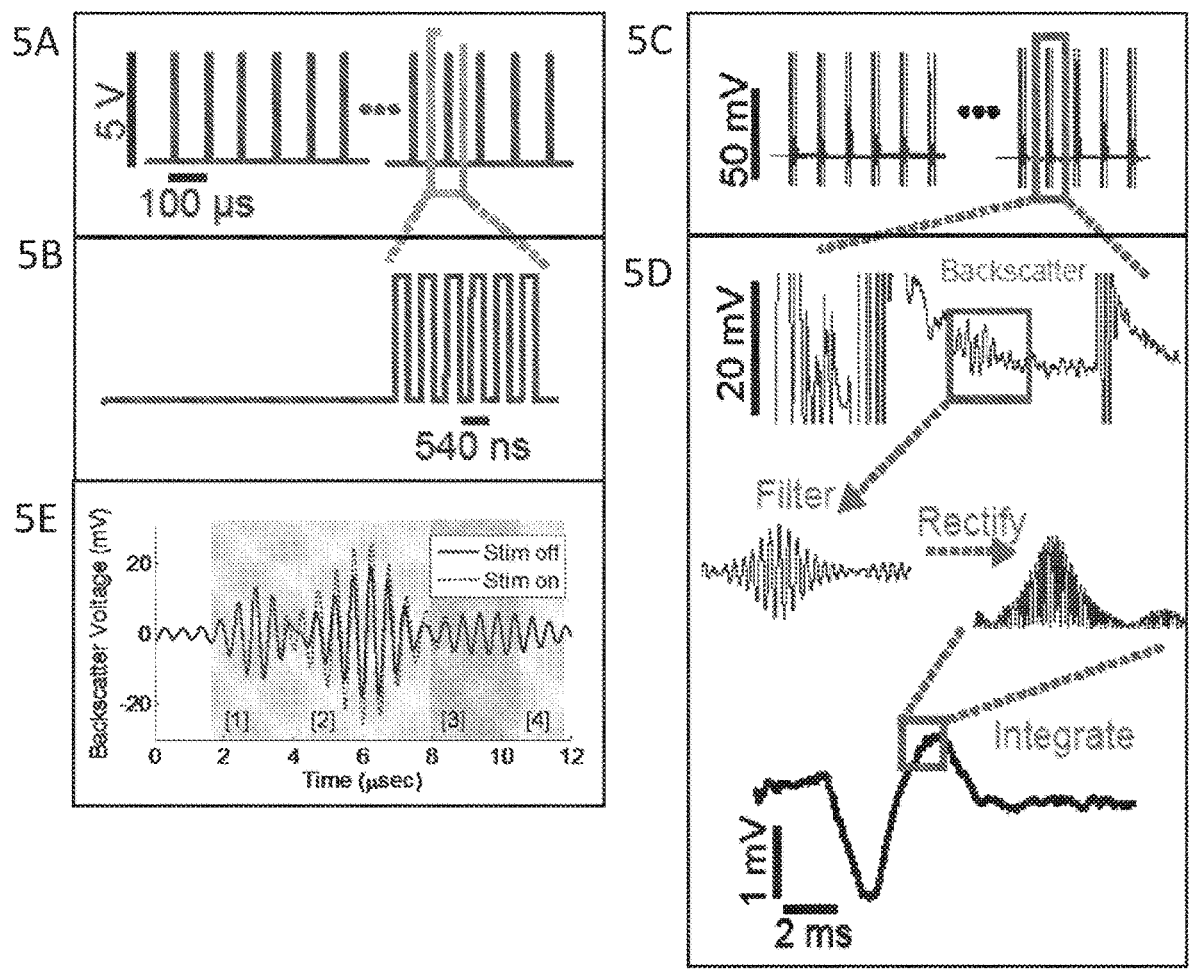
FIG. 5A shows a series of cycles of ultrasonic wave pulses emitted by an interrogator. Upon receiving a trigger from the interrogator (e.g., an FPGA), the transceiver board of the interrogator generates a series of transmit pulses. At the end of the transmit cycle, the switch on the ASIC disconnects the transmit module and connects the receive module. The cycles have a frequency of every 100 microseconds.
FIG. 5B shows a zoomed-in view of the transmit pulse sequence (i.e., one cycle) shown in FIG. 5A, with the cycle having six pulses of ultrasonic waves at 1.85 MHz, the pulses recurring every 540 nanoseconds.
FIG. 5C shows ultrasonic backscatter emitted by an implantable device. The ultrasonic backscatter reaches the transducer of the interrogator approximately 2tRayleigh.
FIG. 5D shows a zoomed-in view of the ultrasonic backscatter, which can be analyzed. Analysis of the ultrasonic backscatter can include filtering, rectifying and integrating the ultrasonic backscatter waves.
FIG. 5E shows a zoomed in view of the filtered ultrasonic backscatter waves. The backscatter wave includes responsive regions, which are responsive to changes in impedance to the miniaturized ultrasonic transducer, and non-responsive regions that are not responsive to changes in impedance to the miniaturized ultrasonic transducer.

FIG. 5 illustrates cycled pulse-echo ultrasonic communication between the interrogator and the implantable device. FIG. 5A shows a series of pulse cycles with a frequency of every 100 microseconds. During the transmission of the pulses, the transducers in the array are configured to transmit the ultrasonic waves. After the pulses are transmitted, the transducers are configured to receive backscattered ultrasonic waves. FIG. 5B shows a zoom-in view of a cycle, which shows six pulses of ultrasonic waves, with a frequency of every 540 nanoseconds. Backscattered ultrasonic waves detected by the interrogator are shown in FIG. 5C, with a zoom-in view of a single pulse shown in FIG. 5D. As shown in FIG. 5D, the ultrasonic backscatter received from the implantable device can be analyzed, which may include filtering (for example, to remove the wave decay) the backscattered waves, rectifying the backscattered waves, and integrating the waves to determine the data encoded by the waves. In some embodiments, the backscatter waves are analyzed using a machine learning algorithm. FIG. 5E shows a zoomed in version of the filtered backscattered waves. The backscatter wave shown in FIG. 5E includes four distinct regions corresponding to reflections arising from mechanical boundaries: (1) reflection from the biocompatible material that encapsulates the implantable device; (2) reflection from the top surface of the miniaturized ultrasonic transducer; (3) reflection from the boundary between the printed circuit board and the miniaturized ultrasonic transducer; and (4) reflection from the back of the printed circuit board. The amplitude of the backscatter waves reflected from the surface of the miniaturized transducer changed as a function of changes in impedance of the current returning to the miniaturized ultrasonic transducer, and can be referred to as the "responsive backscatter" since this region of the backscatter encodes information relating to the detected radiation. The other regions of the ultrasonic backscatter can be referred to as "non-responsive backscatter," and are useful in determining the position of the implantable device, movement of the implantable device, and/or temperature changes proximal to the implantable device, as explained below. In some embodiments, the device further comprises a non-responsive reflector. In some embodiments, the non-responsive reflector is a cube. In some embodiments, the non-responsive reflector comprises silicon. In some embodiments, the non-responsive reflector is a surface of rigid material. The non-responsive reflector is attached to the implantable device but electrically isolated, and can reflect ultrasonic waves that are not responsive to changes in current impedance, for example due to detected radiation.

The frequency of the ultrasonic waves transmitted by the transducer can be set depending on the drive frequency or resonant frequency of the miniaturized ultrasonic transducer on the implantable device. In some embodiments, the miniaturized ultrasonic transducers are broad-band devices. In some embodiments, the miniaturized ultrasonic transducers are narrow-band. For example, in some embodiments the frequency of the pulses is within about 20% or less, within about 15% or less, within about 10% or less, within about 5% or less of the resonant frequency of the miniaturized ultrasonic transducer. In some embodiments, the pulses are set to a frequency about the resonant frequency of the miniaturized ultrasonic transducer. In some embodiments, the frequency of the ultrasonic waves is between about 100 kHz and about 100 MHz (such as between about 100 kHz and about 200 kHz, between about 200 kHz and about 500 kHz, between about 500 kHz and about 1 MHz, between about 1 MHz and about 5 MHz, between about 5 MHz and about 10 MHz, between about 10 MHz and about 25 MHz, between about 25 MHz and about 50 MHz, or between about 50 MHz and about 100 MHz). In some embodiments, the frequency of the ultrasonic waves is about 100 kHz or higher, about 200 kHz or higher, about 500 kHz or higher, about 1 MHz or higher, about 5 MHz or higher, about 10 MHz or higher, about 25 MHz or higher, or about 50 MHz or higher. In some embodiments, the frequency of the ultrasonic waves is about 100 MHz or lower, about 50 MHz or lower, about 25 MHz or lower, about 10 MHz or lower, about 5 MHz or lower, about 1 MHz or lower, about 500 kHz or lower, or about 200 kHz or lower. Higher frequency allows for a smaller miniaturized ultrasonic transducer on the implantable device. However, higher frequency also limits the depth of communication between the ultrasonic transducer and the implantable device. In some embodiments, the implantable device and the ultrasonic transducer are separated by about 0.1 cm to about 15 cm (such as about 0.5 cm to about 10 cm, or about 1 cm to about 5 cm). In some embodiments, the implantable device and the ultrasonic transducer are separated by about 0.1 cm or more, about 0.2 cm or more, about 0.5 cm or more, about 1 cm or more, about 2.5 cm or more, about 5 cm or more, about 10 cm or more, or about 15 cm or more. In some embodiments, the implantable device and the ultrasonic transducer are separated by about 20 cm or less, about 15 cm or less, about 10 cm or less, about 5 cm or less, about 2.5 cm or less, about 1 cm or less, or about 0.5 cm or less.

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which reflect data sensed by the sensor, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. In some embodiments, two or more (such as 3, 4, 5, 6, 7, 8, 9, 10 or more, 12 or more, about 15 or more, about 20 or more, about 25 or more, about 50 or more, or about 100 or more) implantable devices communicate with the interrogator. In some embodiments, about 200 or fewer implantable devices (such as about 150 or fewer, about 100 or fewer, about 50 or fewer, about 25 or fewer, about 20 or fewer, about 15 or fewer, about 12 or fewer, or about 10 or fewer implantable devices) are in communication with the interrogator. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

In some embodiments, the interrogator is used to determine the location or velocity of the implantable device. Velocity can be determined, for example, by determining the position or movement of a device over a period of time. The location of the implantable device can be a relative location, such as the location relative to the transducers on the interrogator. A plurality of transducers, which may be disposed on the same transducer array or two or more different transducer arrays, can collect backscatter ultrasonic waves from an implantable device. Based on the differences between the backscatter waveform arising from the same implantable device and the known location of each transducer, the position of the implantable device can be determined. This can be done, for example by triangulation, or by clustering and maximum likelihood. The differences in the backscatter may be based on responsive backscatter waves, non-responsive backscatter waves, or a combination thereof.

In some embodiments, the interrogator is used to track movement of the implantable device. Movement of the implantable device that can be tracked by the interrogator includes lateral and angular movement. Such movement may arise, for example, due to shifting of one or more organs such as the liver, stomach, small or large intestine, kidney, pancreas, gallbladder, bladder, ovaries, uterus, or spleen (which may be the result, for example, of respiration or movement of the subject), or variations in blood flow (such as due to a pulse). Thus, in some embodiments, the implantable device is useful for tracking movement of an organ or a pulse rate. Movement of the implantable device can be tracked, for example, by monitoring changes in the non-responsive backscatter waves. In some embodiments, movement of the implantable device is determined my comparing the relative location of the implantable device at a first time point to the relative location of the implantable device at a second time point. For example, as described above, the location of an implantable device can be determined using a plurality of transducers on the interrogated (which may be on a single array or on two or more arrays). A first location of the implantable device can be determined at a first time point, and a second location of the implantable device can be determined at a second time point, and a movement vector can be determined based on the first location at the first time point and the second location at the second time point.

In some embodiments, the implantable device includes a clock, which can be calibrated or synced by the interrogator. For example, the interrogator can transmit a signal using the transmitted ultrasonic waves that sets or syncs the clock. The signal can be simultaneously transmitted to a plurality of implantable devices, thereby syncing the clocks of the plurality of implantable devices. In some embodiments, backscatter from the implantable devices encodes a time-stamp based on the clock, which can indicate the time (or relative time) of an event (such as encountered radiation). This can be useful, for example to compare two or more implantable devices and the relative time of encountering radiation.

Implantable Device

Figure 6A:
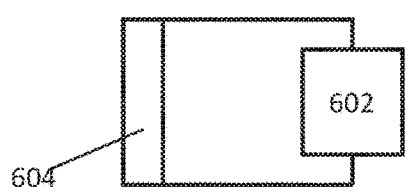
FIG. 6A illustrates a schematic of an implantable device with a miniaturized ultrasonic transducer and a radiation detector (such as a radiation-sensitive transistor, a pixel comprising a radiation-sensitive diode, or an array comprising a plurality of pixels comprising a radiation-sensitive diode).
Figure 6B:
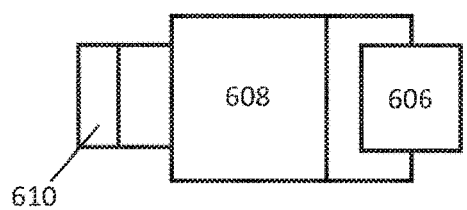
FIG. 6B illustrates a schematic of an implantable device with a miniaturized ultrasonic transducer, an integrated circuit, and a radiation detector.

The implantable device includes a miniaturized ultrasonic transducer (such as a miniaturized piezoelectric transducer, a capacitive micro-machined ultrasonic transducer (CMUT), or a piezoelectric micro-machined ultrasonic transducer (PMUT)) and a radiation detector (such as a radiation-sensitive transistor, a pixel comprising a radiation-sensitive element (e.g., a diode, a transistor, or a flash-memory cell), or an array comprising a plurality of pixels comprising a radiation-sensitive elements). In some embodiments the radiation detector is configured to detect radiation exposure during the lifetime of the implantable device. In some embodiments, the radiation detector is configured to detect the presence of radiation. In some embodiments, the radiation detector is configured to detect the trajectory of a radiation particle. In some embodiments, an application specific integrated circuit (ASIC) is included in the implantable device, which can communicate between the radiation detector and the miniaturized ultrasonic transducer. The interrogator transmits ultrasonic waves, which can power and communicate with the implantable device through the miniaturized ultrasonic transducer on the implantable device. The changed impedance impacts the current flowing within the miniaturized ultrasonic transducer, which impacts the ultrasonic backscatter. Thus, a change in the detected radiation impacts the ultrasonic backscatter, which can be detected by the interrogator. FIG. 6A illustrates a schematic of the implantable device with a miniaturized ultrasonic transducer 602 and a radiation detector 604. FIG. 6B illustrates a schematic of the implantable device with a miniaturized ultrasonic transducer 606, an ASIC 608, and a radiation detector 610.

The implantable devices are miniaturized, which allows for comfortable and long-term implantation while limiting tissue inflammation that is often associated with implantable devices. In some embodiments, the longest dimension of the device is about 5 mm or less, about 4 mm or less, about 3 mm or less, about 2 mm or less, about 1 mm or less, about 0.5 mm or less, about 0.3 mm or less, about 0.1 mm or less in length. In some embodiments, the longest dimension of the device is about 0.05 mm or longer, about 0.1 mm or longer, about 0.3 mm or longer, about 0.5 mm or longer, about 1 mm or longer, about 2 mm or longer, or about 3 mm or longer in the longest dimension of the device. In some embodiments, the longest dimension of the device is about 0.04 mm to about 5 mm in length, about 0.05 mm to about 4 mm in length, about 0.07 mm to about 3 mm in length, about 0.08 mm to about 3 mm in length, or about 1 mm to about 2 mm in length.

In some embodiments, the implantable device has a volume of about 5 mm$^3$ or less (such as about 4 mm$^3$ or less, 3 mm$^3$ or less, 2 mm$^3$ or less, or 1 mm$^3$ or less). In certain embodiments, the implantable device has a volume of about 0.5 mm$^3$ to about 5 mm$^3$, about 1 mm$^3$ to about 5 mm$^3$, about 2 mm$^3$ to about 5 mm$^3$, about 3 mm$^3$ to about 5 mm$^3$, or about 4 mm$^3$ to about 5 mm$^3$. The small size of the implantable device allows for implantation of the device using a biopsy needle.

In some embodiments, the implantable device is implanted in a subject. The subject can be for example, a vertebrate animal, such as a mammal. In some embodiments, the subject is a human, dog, cat, horse, cow, pig, sheep, goat, chicken, monkey, rat, or mouse.

In some embodiments, the implantable device or a portion of the implantable device (such as the miniaturized ultrasonic transducer, the integrated circuit, or all or a portion of the radiation detector) is encapsulated by a biocompatible material (such as a biocompatible polymer), for example a copolymer of N-vinyl-2-pyrrolidinone (NVP) and n-butyl-methacrylate (BMass.), polydimethylsiloxane (PDMS), parylene, polyimide, silicon nitride, silicon dioxide, silicon carbide, alumina, niobium, or hydroxyapatite. The silicon carbide can be amorphous silicon carbide or crystalline silicon carbide. The biocompatible material is preferably impermeable to water to avoid damage or interference to electronic circuitry within the device. In some embodiments, the implantable device or portion of the implantable device is encapsulated by a ceramic (for example, alumina or titania) or a metal (for example, steel or titanium).

Figure 7A:
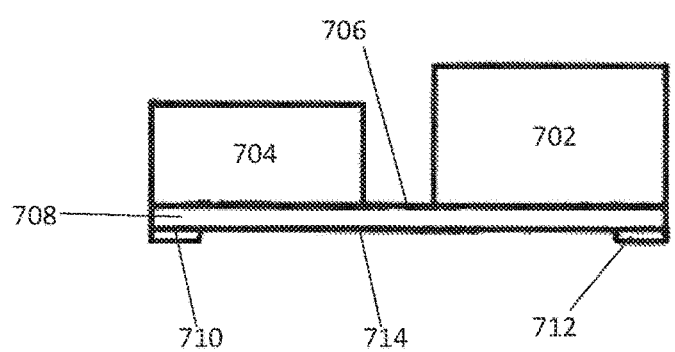
FIG. 7A illustrates a schematic of an exemplary implantable device including a miniaturized ultrasonic transducer and an integrated circuit on a printed circuit board (PCB).
Figure 7B:
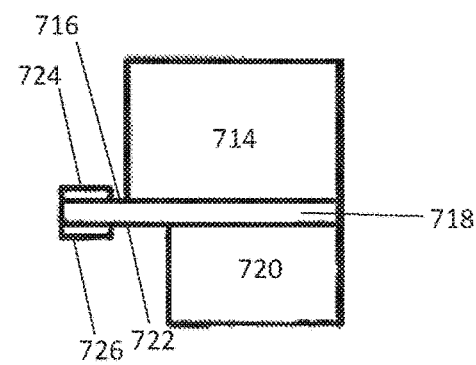
FIG. 7B illustrates a schematic of another exemplary implantable device including a miniaturized ultrasonic transducer and an integrated circuit on a printed circuit board (PCB).

In some embodiments, the miniaturized ultrasonic transducer and, if present, the ASIC, are disposed on a printed circuit board (PCB). The radiation detector can optionally be disposed on the PCB, or can otherwise be connected to the ASIC. FIGS. 7A and 7B illustrate exemplary configurations of the implantable device including a PCB. FIG. 7A shows the piezoelectric transducer 702 and an ASIC 704 disposed on a first side 706 of the PCB 708. A first electrode 710 and a second electrode 712 are disposed on a second side 714 of the PCB 708. The first electrode 710 and the second electrode 712 can be, for example, connected to the radiation detector. FIG. 7B sows the piezoelectric transducer 714 on a first side 716 of the PCB 718, and the ASIC 720 on the second side 722 of the PCB 718. A first electrode 724 is disposed on the first side 716 of the PCB, and a second electrode 726 is disposed on the second side 722 of the PCB 718. The first electrode 724 and the second electrode 726 can be, for example, connected to the radiation detector.

The miniaturized ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the miniaturized bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the miniaturized bulk piezoelectric transducer is long and narrow, with an aspect ratio of about 3:1:1 or greater, and where the longest dimension is aligned to the direction of propagation of the carrier ultrasound wave. In some embodiments, one dimension of the bulk piezoelectric transducer is equal to one half of the wavelength (λ) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 µm to about 1000 µm (such as about 40 µm to about 400 µm, about 100 µm to about 250 µm, about 250 µm to about 500 µm, or about 500 µm to about 1000 µm). In some embodiments, the height of the piezoelectric transducer is about 5 mm or less (such as about 4 mm or less, about 3 mm or less, about 2 mm or less, about 1 mm or less, about 500 µm or less, about 400 µm or less, 250 µm or less, about 100 µm or less, or about 40 µm or less). In some embodiments, the height of the piezoelectric transducer is about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in length.

In some embodiments, the ultrasonic transducer has a length of about 5 mm or less such as about 4 mm or less, about 3 mm or less, about 2 mm or less, about 1 mm or less, about 500 µm or less, about 400 µm or less, 250 µm or less, about 100 µm or less, or about 40 µm or less) in the longest dimension. In some embodiments, the ultrasonic transducer has a length of about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in the longest dimension.

The miniaturized ultrasonic transducer is connected two electrodes; the first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene (PEDOT), a conductive polymer (such as conductive PDMS or polyimide), or nickel. In some embodiments, the transducer is operated in shear-mode where the axis between the metallized faces (i.e., electrodes) of the transducer is orthogonal to the motion of the transducer.

The miniaturized ultrasonic transducer is connected to a sensor and, in some embodiments, an integrated circuit. The integrated circuit, if present, can be integrated with the radiation detector or provided separately from the radiation detector.

In some embodiments, the integrated circuit includes a power circuit, which is configured to power components of the implanted device. The power circuit can include, for example, a rectifier, a charge pump, and/or an energy storage capacitor. In some embodiments, the energy storage capacitor is included as a separate component. Ultrasonic waves that induce a voltage differential in the miniaturized ultrasonic transducer provide power for the implantable device, which can be managed by the power circuit.

In some embodiments the ASIC comprises one or more analog circuit which utilizes the electrical power provided by the transducer to power one or more analog amplifiers, increasing the modulation depth of the signal modulated onto the backscatter impedance. In some embodiments the ASIC includes one or more digital circuits, which can include a memory and one or more circuit blocks or systems for operating the implantable device; these systems can include, for example an onboard microcontroller, a finite state machine implementation or digital circuits capable of executing programs stored on the implant or provided via ultrasonic communication between interrogator and implant. In some embodiments, the digital circuit includes an analog-to-digital converter (ADC), which can convert analog signal from the sensor into a digital signal. In some embodiments, the digital circuit includes a digital-to-analog converter (DAC), which converts a digital signal into an analog signal prior to directing the signal to a modulator. In some embodiments, the implantable device comprises a non-transient memory, which can store information related to the detected radiation particle or wave. The information can comprise, for example, a timestamp, energy of the radiation particle, or a directional vector of the radiation. In some embodiments, the implantable device stores the information to be retrieved at a later time.

In some embodiments, the digital circuit can operate a modulation circuit (which can also be referred to as the "backscatter circuit"), which connects to the miniaturized ultrasonic transducer. The modulation circuit includes a switch, such as an on/off switch or a field-effect transistor (FET). An exemplary FET that can be used with some embodiments of the implantable device is a metal-oxide-semiconductor field-effect transistor (MOSFET). The modulation circuit can alter the impedance presented to the miniaturized ultrasonic transducer, and the variation in current passing through the transducer encodes signals transmitted by the digital circuit. The digital circuit can also operate one or more amplifiers, which amplifies the current directed to the switch. In embodiments where the digital circuit is omitted, the impedance in the modulation circuit can be directly controlled by the radiation detector.

The integrated circuit or a portion of the integrated circuit can be covered by a radiation shield. Certain components of the integrated circuit, such as the modulation circuit, may be sensitive to radiation, and protecting the integrated circuit using a radiation shield can be useful to extend the life or enhance reliability of the implantable device. The radiation shield can be, for example, a metal sheet.

In some embodiments, the integrated circuit includes a driver circuit, which provides current to the radiation detector. The driver circuit can be operated by the digital circuit if present. In some embodiments, one or more amplifiers are disposed between the driver circuit and the digital circuit. In some embodiments, the integrated circuit includes a front end circuit (such as a CMOS front end), which can receive a signal from the radiation detector. The signal received by the front end circuit can be relayed to the digital circuit.

Figure 8A:
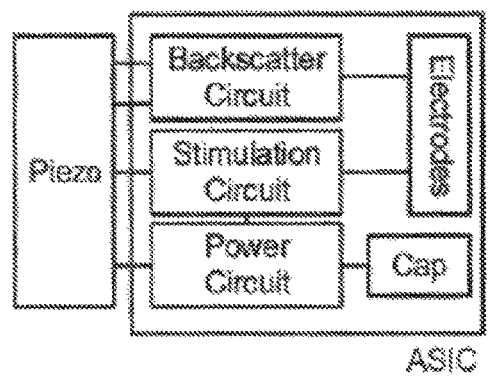
FIG. 8A illustrates one embodiment of an integrated circuit attached to a miniaturized ultrasonic transducer for an implantable device.

FIG. 8A includes one embodiment of a miniaturized ultrasonic transducer (identified as the "piezo") connected to an ASIC. The ASIC includes a power circuit, a modulation circuit (or "backscatter circuit"), and a driver (the "stimulation circuit"). The power circuit includes an energy storage capacitor ("cap"). The electrodes can be connected to the radiation detector.

Figure 8B:
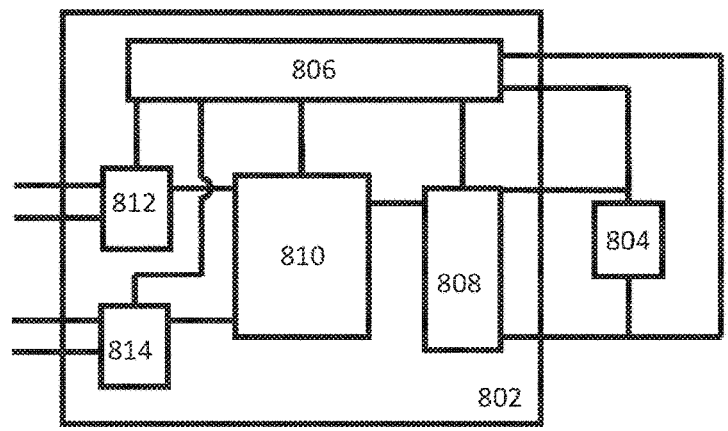
FIG. 8B illustrates another embodiment of an integrated circuit attached to a miniaturized ultrasonic transducer for an implantable device.

FIG. 8B illustrates another example of an ASIC 802 connected to the miniaturized ultrasonic transducer 804. In the illustrated embodiment, the miniaturized ultrasonic transducer 804 is connected to a power circuit 806. The power circuit 806 provides power to the other components of the ASIC, including the modulation circuit 808, the digital circuit 810, the driver 812, and the front end 814. The digital circuit 810 operates the driver 812, which can be connected to a sensor (not shown). The front end circuit 814 receives signal from the sensor and transmits the signal to the digital circuit 810. The digital circuit 810 can then control the modulation circuit 808, which controls impedance of the current returning to the miniaturized ultrasonic transducer 804.

Dosimetry Dust

Figure 9A:
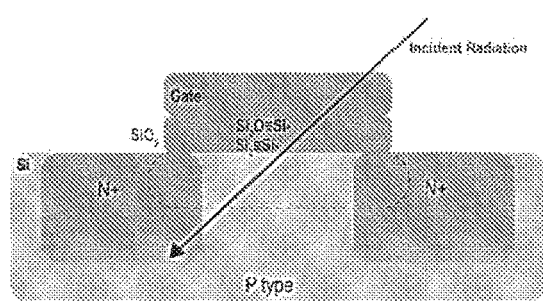
FIG. 9A shows radiation interacting with a radiation-sensitive transistor (a MOSFET) comprising a silicon insulator. Incident radiation results in damage to the MOSFET, resulting in a lower gate threshold as shown in FIG. 9B.
Figure 9B:
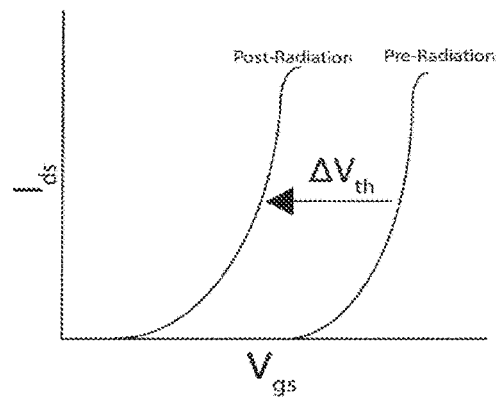
FIG. 9C shows ultrasonic backscatter emitted by the implantable device following exposure of the radiation-sensitive transistor to radiation.
Figure 9C:
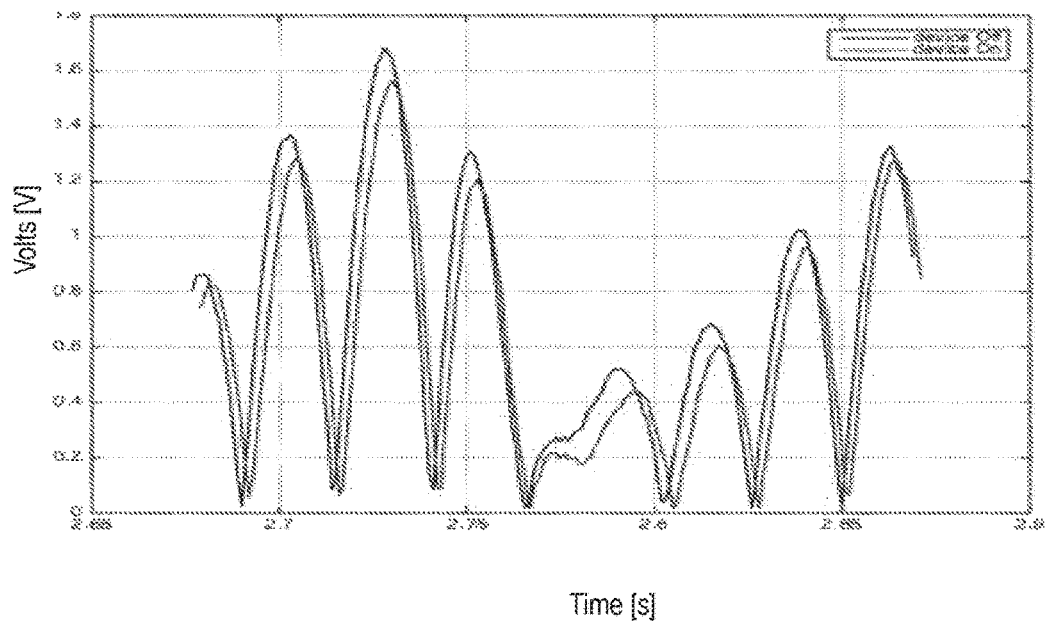

In some embodiments, the implantable device functions as a dosimeter. The implantable device comprises a miniaturized ultrasonic transducer (bulk piezoelectric transducer, a PMUT, or a CMUT) and a radiation-sensitive element (such as a transistor, a diode, or a flash memory cell) or an array comprising a plurality of pixels comprising a radiation-sensitive element. In some embodiments, the array is coated with a scintillator material. Exemplary scintillator materials include $LaBr_3(Ce)$, $Cs_2LiLaBr_6(Ce)$, NaI(Tl), CsI(Na), $Lu_{1.8}Y_{0.2}SiO_5$, $CdWO_4$, $CaF_2$, CsI(Tl), bismuth germinate (BGO), $Y_3Al_5O_{12}(Ce)$, CsI, $BaF_2$, and ZnS(Ag). The radiation-sensitive transistor can be, for example a metal-oxide-semiconductor field effect transistor (MOSFET), which may be either a n-channel MOSFET (nMOS) or a p-channel MOSFET (pMOS). In some embodiments, the radiation-sensitive transistor comprises a silicon-oxide interface. When ionizing radiation (such as a protons, alpha-particles, beta-particles, or gamma-rays) interacts with the silicon-oxide interface, the gate oxide ($SiO_2$) of the interface is damaged, generating interface traps and/or oxide charges. FIG. 9A shows radiation interacting with a MOSFET comprising a silicon-oxide interface, resulting in damage to the MOSFET. The radiation-induced damage to the radiation-sensitive transistor results in a lower gate threshold, $V_T$, for the transistor, as shown in FIG. 9B. The lower gate threshold will alter the drain-source current drawn for the MOSFET, which thereby alters the impedance for the radiation-sensitive transistor. This change in impedance for the radiation-sensitive transistor modulates the current returning to the miniaturized ultrasonic transducer, and thus the resulting backscatter. This is seen in FIG. 9C, which shows ultrasonic backscatter waves from an implantable device before and after exposure to radiation. The change in gate threshold $\Delta V_T$ (and thus, impedance) is quasi-permanent for the lifetime of the transistor (although there may be some reversion to the baseline over time). Therefore, the gate threshold is indicative of the amount of exposure to radiation, and the current flowing through the transistor is modulated as a function of the radiation exposure.

The radiation-sensitive transistor includes a source, a drain, a body, and a gate. In some embodiments, the drain is directly connected to the gate. In some embodiments, a resistor bridge comprising one or more transistors connects the source and the drain. In some embodiments, the gate is directly connected to the resistor bridge, for example between a first resistor and a second resistor. The resistor bridge can act as a "ground" terminal for in vivo measurements, and can be connected to the body, the drain or the source. In some embodiments, the body is connected to the source or the drain. In some embodiments, the source and the drain are connected to miniaturized ultrasonic transducer. In some embodiment, the source and the drain are connected to an integrated circuit, such as the digital circuit in the integrated circuit.

Figure 10A:
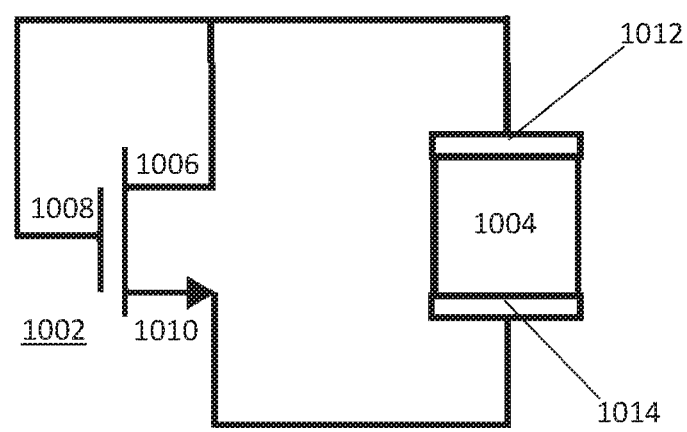
FIG. 10A shows one example of an implantable device with a radiation sensitive transistor and a miniaturized ultrasonic transducer.

FIG. 10A illustrates one embodiment of an implantable device with a radiation-sensitive transistor 1002 and a miniaturized ultrasonic transducer 1004. In the illustrated embodiment, the gate 1006 and drain 1008 of the transistor 1002 are directly connected. The transistor 1002 further includes a source 1010. The drain 1008 and the source 1010 are connected to the transducer 1004 through a first electrode 1012 and a second electrode 1014. In this configuration, the changes can be observed when the transducer voltage is positive if the transistor is an nFET or negative if the transistor is a pFET.

Figure 10B:
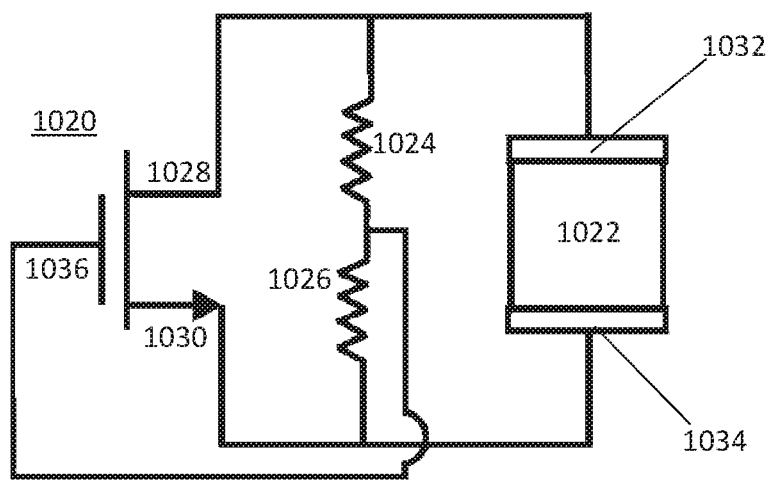
FIG. 10B shows an example of an implantable device with a radiation-sensitive transistor, a miniaturized ultrasonic transducer, and a resistor bridge that joins the drain and the source of the transistor.

FIG. 10B illustrates another embodiment of an implantable device with a radiation-sensitive transistor 1020 and a miniaturized ultrasonic transducer 1022. The implantable device further includes a resistor bridge comprising a first resistor 1024 and a second resistor 1026, which connects the drain 1028 and the source 1030 of the transistor 1020. The drain 1028 and the source 1030 are also connected to the transducer 1022 through a first electrode 1032 and a second electrode 1034. The gate 1036 of the transistor 1020 is directly connected to the resistor bridge between the first resistor 1024 and the second resistor 1026. In this configuration, changes in the transistor can be observed every cycle, but the maximum voltage in the transistor, $V_{gs}$, will be half the maximum $V_{gs}$ of the embodiment shown in FIG. 10A.

In some embodiments, the implantable device comprises a radiation-sensitive transistor configured to modulate a current as a function of radiation exposure to the transistor; and an ultrasonic device comprising a miniaturized ultrasonic transducer configured to emit an ultrasonic backscatter that encodes the exposure of the transistor to radiation. In some embodiments, the radiation-sensitive transistor is a metal-oxide-semiconductor field effect transistor (MOSFET), for example a p-channel MOSFET (pMOS) or an n-channel MOSFET (nMOS). In some embodiments, the gate and the drain of the radiation-sensitive transistor are directly connected. In some embodiments, the implantable device comprises a resistor bridge comprising two or more resistors bridging the drain and the source of the transistor, and the gate is directly connected to the resistor bridge between two of the resistors. Preferably, the implantable device is miniaturized, and has a length of about 5 mm or less (such as about 4 mm or less, about 3 mm or less, about 2 mm or less, or about 1 mm or less) in the longest dimension.

In some embodiments, the implantable device comprises a radiation-sensitive transistor configured to modulate a current as a function of radiation exposure to the transistor; an ultrasonic transducer configured to emit an ultrasonic backscatter that encodes the exposure of the transistor to radiation based on the modulated current, and an integrated circuit through which the current modulated by the radiation-sensitive transistor flows and transmit a signal encoding the exposure of the transistor to radiation to the ultrasonic transducer. The signal can be an analog or digitized signal, and the digital circuit can transmit the signal to the ultrasonic transducer by modulating a current to the ultrasonic transducer via a modulation circuit comprising a switch. In some embodiments, the radiation-sensitive transistor is a metal-oxide-semiconductor field effect transistor (MOSFET), for example a p-channel MOSFET (pMOS) or an n-channel MOSFET (nMOS). In some embodiments, the gate and the drain of the radiation-sensitive transistor are directly connected. In some embodiments, the implantable device comprises a resistor bridge comprising two or more resistors bridging the drain and the source of the transistor, and the gate is directly connected to the resistor bridge between two of the resistors. Preferably, the implantable device is miniaturized, and has a length of about 5 mm or less (such as about 4 mm or less, about 3 mm or less, about 2 mm or less, or about 1 mm or less) in the longest dimension.

Figure 11:
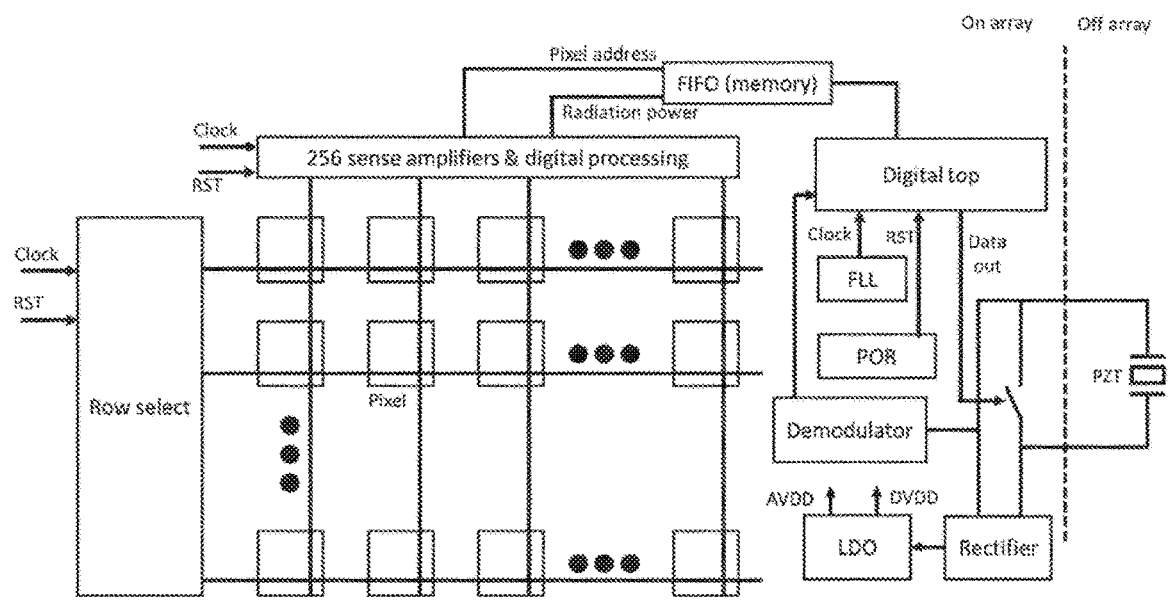
FIG. 11 shows an exemplary array comprising a plurality of pixels. The pixels include a radiation-sensitive diode, and signal from the pixels is transmitted to a CMOS front end.
Figure 12A:
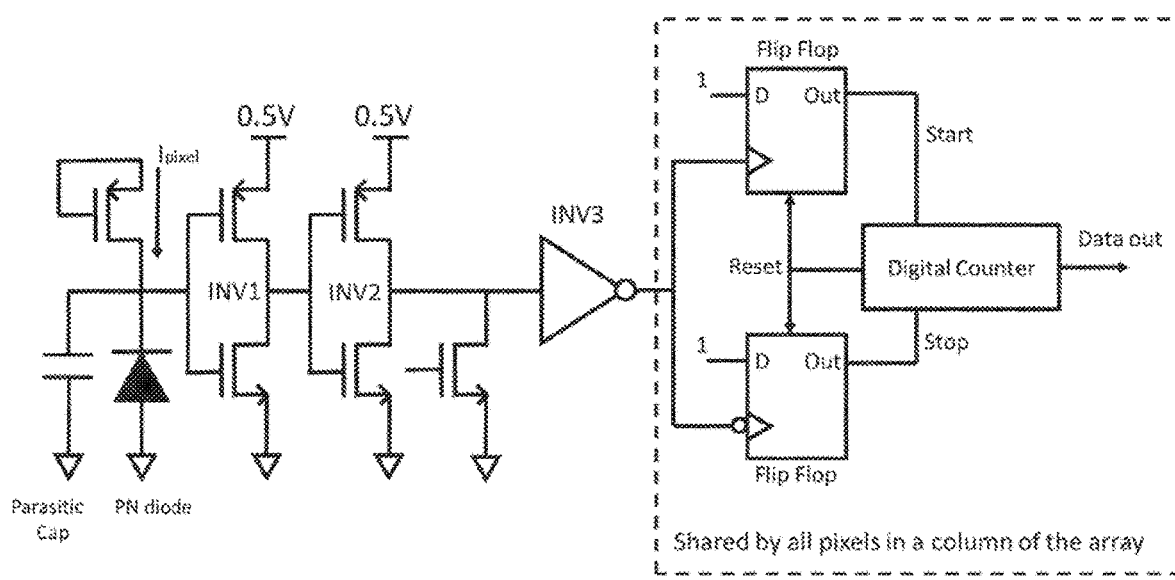
FIG. 12A shows a pixel comprising a radiation-sensitive diode connected to a signal processing unit.
Figure 12B:
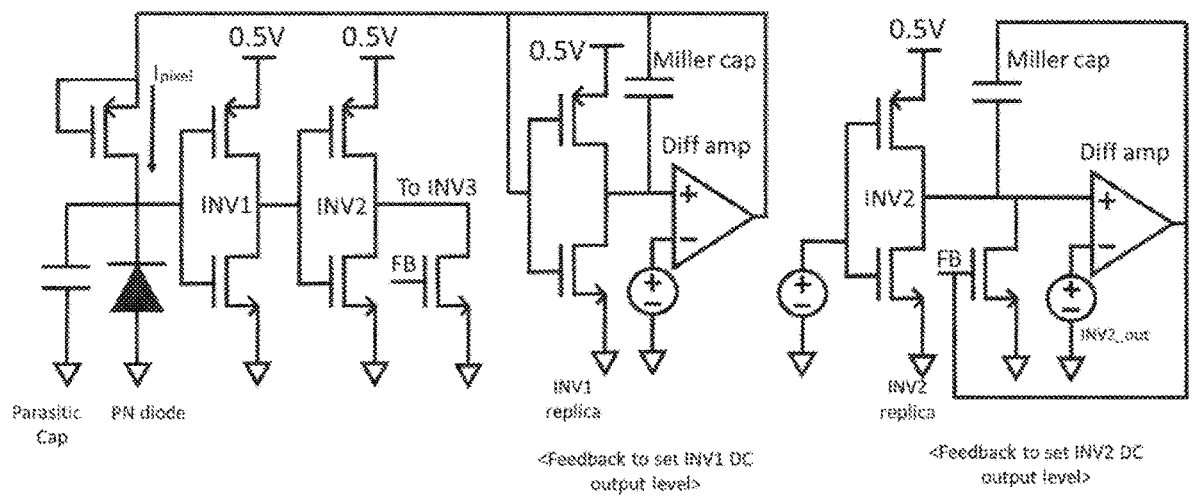
FIG. 12B shows a pixel comprising a radiation-sensitive diode connected to an analog front end.
Figure 12C:
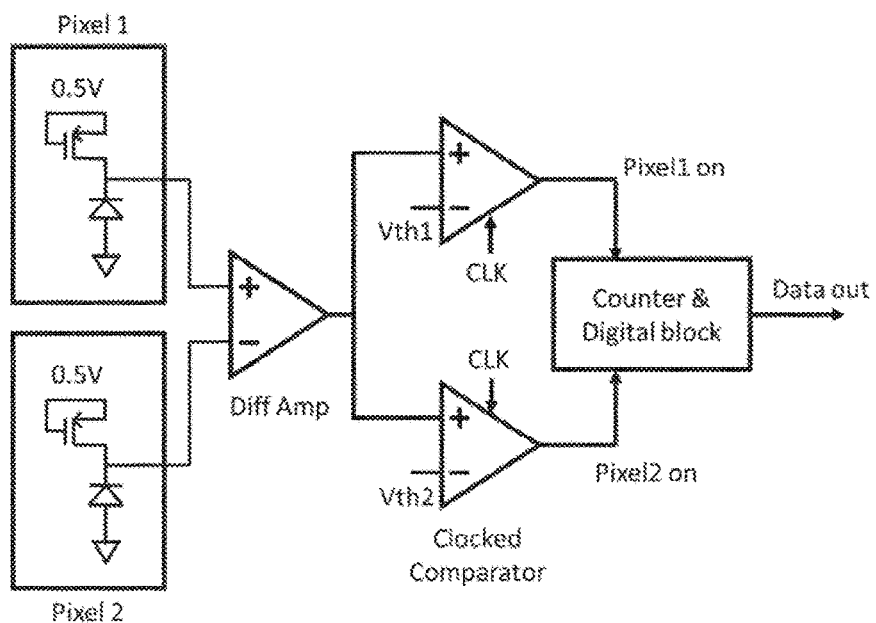
FIG. 12C illustrates two pixels, each with a radiation-sensitive diode, that is connected to a signal processing unit.

In some embodiments, the implantable device comprises a miniaturized ultrasonic transducer (bulk piezoelectric transducer, a PMUT, or a CMUT) and one or more radiation-sensitive elements (such as a diode, a transistor, or flash memory cell). In some embodiments, the implantable device comprises a miniaturized ultrasonic transducer (bulk piezoelectric transducer, a PMUT, or a CMUT) and one or more arrays comprising a plurality of pixels comprising a radiation-sensitive element (such as a diode, a transistor, or flash memory cell). When radiation encounters the radiation-sensitive diode, one or more electron-hole pairs can be generated, thereby generating a transient current. The number of electron-hole pairs is a function of the energy of the incident radiation as well as other factors, including the properties of the interface materials. A transient electrical current can therefore be generated, with the amplitude of the current reflecting the energy of the radiation. The array can include a CMOS front end, which can transmit an electrical signal to the ultrasonic transducer encoding the location of the pixel within the array (i.e., the "pixel address") that was excited by the radiation. Cycling can be fast enough such that only a single radiation particle or wave is detected by the array at a time. In some embodiments, the signal encodes the energy of the radiation. This signal is then converted into ultrasonic backscatter waves emitted by the implantable device and received by the interrogator. Therefore, the radiation-sensitive diode allows for determination radiation (or counts of radiation), and optionally the energy of the radiation. In some embodiments, the array comprises 2 or more pixels (such as 8 or more, 16 or more, 32 or more, 64 or more, 125 or more 250 or more, 500 or more, 1000 or more, 2000 or more, 4000 or more, 8000 or more, 16,000 or more, 30,000 or more, or 60,000 or more pixels). An exemplary array with a CMOS front end and 256×256 pixels is illustrated in FIG. 11. Exemplary pixels comprising radiation-sensitive diodes are shown in FIGS. 12A-C.

Figure 13A:
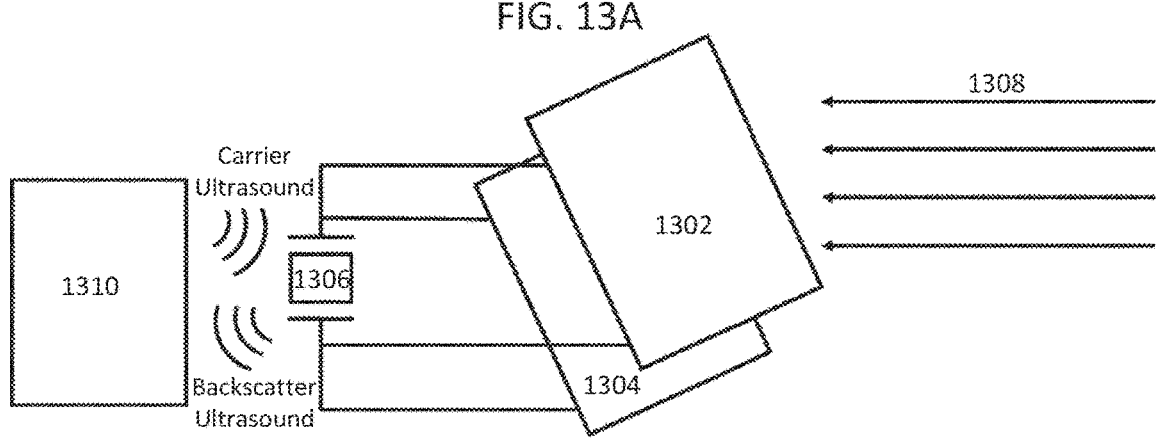
FIG. 13A illustrates an embodiment of an implantable device having a miniaturized ultrasonic transducer and two arrays. The arrays include a plurality of pixels, each pixel having a radiation-sensitive diode. The implantable device is in communication with an interrogator, which can communicate with and power the implantable device using ultrasonic waves. Radiation encounters one or more pixels within the array, and the incident radiation is encoded on ultrasonic backscatter emitted from the implantable device.
Figure 13B:
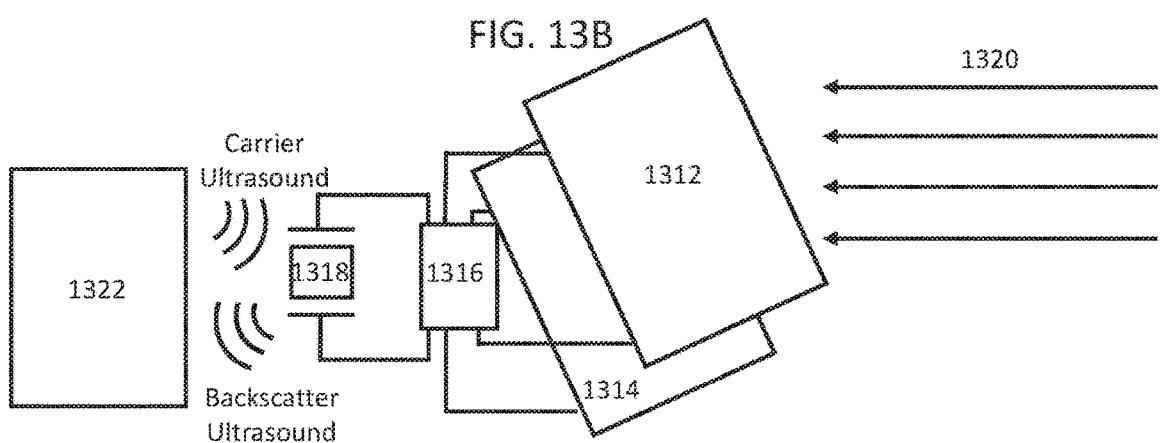
FIG. 13B illustrates another embodiment of the implantable device, wherein the two arrays are connected to a separate integrated circuit, which is connected to the miniaturized ultrasonic transducer.
Figure 13C:
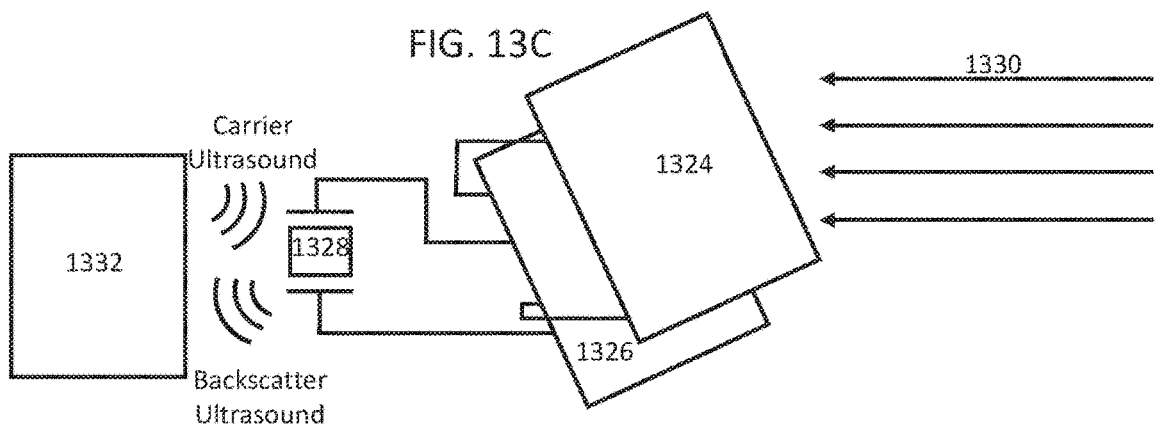
FIG. 13C illustrates another embodiment of the implantable device, with a first array connected to the second array (such as in a master-slave configuration), wherein the second array is connected to the miniaturized ultrasonic transducer (which may or may not be through a separate integrated circuit).

In some embodiments, the implantable device comprises two or more arrays comprising a plurality of radiation-sensitive pixels (the pixels each having a radiation-sensitive element (such as a diode, a transistor, or flash memory cell). In some embodiments, the arrays are disposed in parallel planes. By stacking the arrays, a directional vector of the radiation can be determined based on the pixel address of a first pixel on a first array and a second pixel on a second array, wherein both the first pixel and the second pixel encounter the radiation. Determining the directional vector of the incident radiation, for example radiation applied to a cancer during radiation treatment, can allow the radiation to be retargeted toward the cancer and away from the implantable device. An exemplary embodiment of an implantable device comprising two arrays is shown in FIG. 13A. The implantable device includes a first array 1302 and a second array 1304. Each of the arrays includes a plurality of radiation-sensitive pixels and an ASIC. The first array 1302 and the second array 1304 are connected to a miniaturized ultrasonic transducer 1306. Radiation 1308 (such as a proton beam) can be targeted to a location near the implantable device, but off-target radiation may encounter one or more pixels in the array. When radiation encounters a pixel in one or both arrays, a signal is transmitted to the ultrasonic transducer 1306. The ultrasonic transducer 1306 converts the electrical signal to ultrasonic backscatter, and the ultrasonic waves are transmitted to an interrogator 1308. The interrogator 1310 also transmits ultrasonic waves (carrier waves) to the implantable device, which can be used, for example, to power the ASICS on the arrays. FIG. 13B illustrates a configuration of the implantable device comprising the first array 1312 and the second array 1314. The first array 1312 and the second array 1314 are connected to an integrated circuit 1316, which can include the modulation circuit. The integrated circuit 1316 is connected to the miniaturized ultrasonic transducer 1318. Radiation 1320 (such as a proton beam) can be targeted to a location near the implantable device, but off-target radiation may encounter one or more pixels in the array. When radiation encounters a pixel in one or both of the arrays, a signal is transmitted to the integrated circuit 1316, which modulates the current flowing through the miniaturized ultrasonic transducer 1318. The ultrasonic transducer 1318 converts the electrical signal into ultrasonic backscatter, and the ultrasonic backscatter waves are transmitted to the interrogator 1322. FIG. 13C illustrates another embodiment of the implantable device with two arrays. The first array 1324 can be connected to the second array 1326 via a dedicated line or a bus. The second array 1326 is connected to the miniaturized ultrasonic transducer 1328. Radiation 1330 (such as a proton beam) can be targeted to a location near the implantable device, and off-target radiation can encounter one or more pixels in the first array 1324 or the second array 1326. When radiation encounters a pixel in the first array 1324, a signal is transmitted to the second array 1326. The second array 1326 can relay the radiation encounter in the first array 1324, or a radiation encounter in the second array 1326, to the miniaturized ultrasonic transducer 1328. The ultrasonic transducer 1328 converts the received signal into ultrasonic backscatter, which is transmitted to the interrogator 1332.

In some embodiments the implantable device with a radiation-sensitive element (such as a diode, a transistor, or flash memory cell), or an array comprising a plurality of radiation-sensitive pixels (each pixel comprising a radiation-sensitive element) is used to detect localized radiation exposure. The irradiated radiation-sensitive transistor modulates the ultrasonic backscatter (including amplitude of the ultrasonic waves), and the changes in the ultrasonic backscatter can be correlated to a received radiation dose. For implantable devices comprising one or more radiation-sensitive elements, the implantable device can emit ultrasonic backscatter encoding the radiation particle or wave encountering the element.

In some embodiment, encountered radiation from a radiation source (e.g., a radiation beam or radiolabeled cell or cluster of cells) is filtered from noise or background radiation. Radiation from the source is generally higher energy radiation than noise or background radiation. In some embodiments, the radiation is filtered based on the magnitude of signal from a radiation sensitive diode. For example the radiation sensitive diode can encounter a radiation particle or wave to generate a transient electrical signal. If that signal is below a predetermined threshold, it can be filtered, and if at or above the predetermined threshold it can be encoded into the ultrasonic backscatter. Filtering can occur within the diode, within the array, within the digital circuit, within the modulation circuit, or any other appropriate component of the implantable device.

In some embodiments, radiation is filtered based on scattering angles. High energy particles forward scatter, whereas lower energy particles have a larger distribution of scattering angles. For example, in some embodiments, the implantable device comprises three or more stacked arrays. Radiation particles or waves can travel between the first and second array at a first directional vector, and between the second and third arrays at a second directional vector. Energy of the particle can be determined based on the angle differences of the directional vectors, and lower energy particles can be filtered. In some embodiments a material may be placed between the arrays (which may be the same material or different material between the first and second arrays and the second and third arrays). An exemplary material is silica. In some embodiments, the distance between the arrays is the same or different.

In one aspect, there is provided a method of detecting radiation. In an exemplary embodiment, ultrasonic waves are received by one or more implantable devices receiving ultrasonic waves that power the one or more implantable devices. The implantable device or devices include an ultrasonic transducer and a radiation-sensitive transistor. Energy from the ultrasonic waves is converted into an electrical current and/or voltage. The radiation-sensitive transistor is exposed to radiation (e.g., radiation particles or radiation waves, which can originate from a radiation source, such as a proton beam). The electrical current flowing through the transducer is then modulated based on an amount of radiation exposed to the radiation-sensitive transistor. The modulated electrical current is then transduced into an ultrasonic backscatter that encodes the amount of radiation exposed to the radiation-sensitive transistor. That is, a higher dose of radiation exposure will result in a different backscatter waveform. The amount of radiation exposed to the radiation-sensitive transistor encoded by the ultrasonic backscatter can be a lifetime amount of radiation exposed to the radiation sensitive transistor (that is, the amount of radiation exposed to the implantable device after an initial calibration) or the amount of radiation exposed to the radiation-sensitive transistor between any two later time points (i.e., a first time point and a second time point). Determining the amount of radiation exposed to the radiation-sensitive transistor at a first time point and a second time point, further allows for determining the rate of radiation exposure. The ultrasonic backscatter is emitted to an interrogator comprising one or more transducers configured to receive the ultrasonic backscatter. In some embodiments, the method comprises determining the location of the one or more implantable devices, which allows for accurate determination of the location of the radiation exposure.

In another exemplary embodiment of a method for determining radiation exposure, ultrasonic waves are received by one or more implantable devices receiving ultrasonic waves that power the one or more implantable devices. The implantable device or devices include an ultrasonic transducer and a radiation-sensitive transistor. Energy from the ultrasonic waves is converted into a first electrical current and/or voltage, which is transmitted to an integrated circuit. The integrated circuit can transmit a second electrical current to the radiation-sensitive transistor. The radiation-sensitive transistor is exposed to radiation (e.g., radiation particles or radiation waves, which can originate from a radiation source, such as a proton beam). The second electrical current is then modulated based on an amount of radiation exposed to the radiation-sensitive transistor, which is then transmitted to the integrated circuit. The integrated circuit can then modulate the first electrical current, which is then transduced into an ultrasonic backscatter that encodes the amount of radiation exposed to the radiation-sensitive transistor. That is, a higher dose of radiation exposure will result in a different backscatter waveform. The amount of radiation exposed to the radiation-sensitive transistor encoded by the ultrasonic backscatter can be a lifetime amount of radiation exposed to the radiation sensitive transistor (that is, the amount of radiation exposed to the implantable device after an initial calibration) or the amount of radiation exposed to the radiation-sensitive transistor between any two later time points (i.e., a first time point and a second time point). Determining the amount of radiation exposed to the radiation-sensitive transistor at a first time point and a second time point, further allows for determining the rate of radiation exposure. The ultrasonic backscatter is emitted to an interrogator comprising one or more transducers configured to receive the ultrasonic backscatter. In some embodiments, the method comprises determining the location of the one or more implantable devices, which allows for accurate determination of the location of the radiation exposure.

In another embodiment of a method of detecting radiation, ultrasonic waves are received by one or more implantable devices comprising an ultrasonic transducer, an integrated circuit, and a radiation-sensitive diode configured to generate a signal upon encountering radiation. The ultrasonic waves can power the one or more implantable devices. Energy from the ultrasonic waves is converted into an electrical current. The electrical current is then transmitted to the integrated circuit. Optionally, the integrated circuit stores the energy from the electrical current, for example in an energy storage capacitor. The diode is exposed to a radiation particle or radiation wave from a radiation source (such as a proton beam or a radiolabeled cluster of cells, such as a cluster of cancer cells). A signal is transmitted to the integrated circuit that indicates exposure of the diode to the radiation particle or wave. The integrated circuit then modulates the electrical current based the signal transmitted to the integrated circuit, which is transduced to an ultrasonic backscatter that encodes the radiation exposure. The ultrasonic backscatter is then emitted to an interrogator comprising one or more transducer configured to receive the ultrasonic backscatter. In some embodiments, the method comprises determining the location of the one or more implantable devices, which allows for accurate determination of the location of the radiation exposure.

In some embodiments, one or more implantable devices are implanted near a tumor. The cancer is generally a solid cancer, such as bone cancer, breast cancer, bladder cancer, colorectal cancer, eye cancer, gastric cancer, head and neck cancer, renal cancer, liver cancer, lung cancer, a glioma, ovarian cancer, pancreatic cancer, prostate cancer, thyroid cancer, or uterine cancer, Brain cancer, spinal cancer (such as spinal cord cancer or spinal canal cancer), colon cancer, cecal cancer, gall bladder cancer, testicular cancer, sarcoma, rectal cancer, anal cancer, skin cancer, or a metastatic cancer. In some embodiments, the implantable device is implanted on or near an organ. The organ may be a sensitive organ located next to a cancer treated with a radiation therapy. Limiting radiation exposure to nearby organs can help limit unwanted side effects resulting from radiation therapy. In some embodiments, the organ is a stomach, bladder, kidney, liver, lung, heart, brain, ovaries, pancreas, uterus, thyroid, small intestine, or large intestine.

Real-time radiation exposure can be monitored by analyzing ultrasonic backscatter waves using the interrogator during radiation exposure, such as a radiation based cancer treatment (such as X-ray therapy or proton beam therapy). In some embodiments, radiation exposure is determined after radiation exposure.

Figure 14:
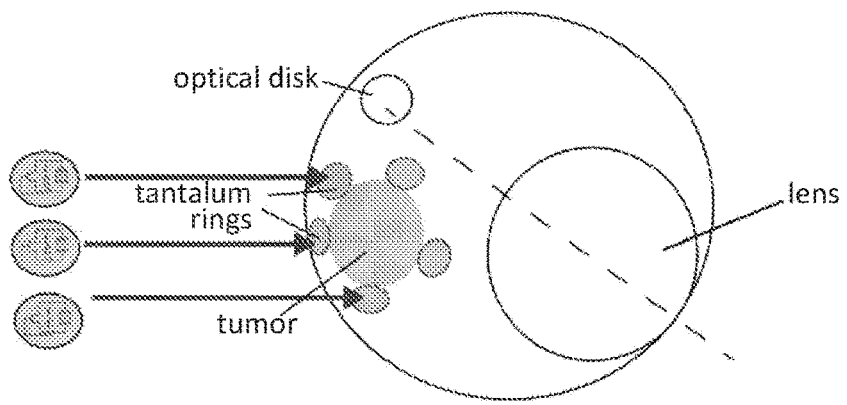
FIG. 14 illustrates a method of monitoring off-target radiation upon treatment of a solid cancer. The solid cancer in the illustrated example is in the eye of a subject. Tantalum rings surround the cancer to mark the location of the cancer Implantable devices comprising radiation-sensitive transistors are implanted proximal to the cancer (i.e., along the perimeter of the cancer). The cancer can be treated with radiation, such as a proton beam. Off-target radiation will expose the implantable device to the radiation, which can be reported using ultrasonic backscatter.

The tumor is treated with a dose of radiation, and the radiation exposure of the implantable devices can be monitored in real time. High radiation exposure to the implantable device indicates off-target radiation exposure (if the implantable device is located adjacent to the target) or on-target radiation exposure (if the implantable device is located on or at the target), and the radiation treatment can be suspended or re-targeted accordingly. Further, in some embodiments, the location of the implantable device is determined, as described above, which can allow the implantable device to be used as a marker to re-target the radiation therapy. One example is shown in FIG. 14. The implantable device can be implemented in 67.5 MeV proton beam therapies for ocular melanomas, such as at the Crocker Nuclear Laboratory. Patient treatment at the Crocker Nuclear Laboratory includes four 14Gy doses, with a total overall dose of 56Gy. Treatment can begin with a minor surgery approximately two weeks prior to irradiation. In this procedure, metal rights (such as tantalum rings) sutured to the sclera of an eye serve as a reference to mark the tumor's location once proton beam therapy treatment begins. The implantable device can be strategically placed during the surgery to monitor received tumor dose.

In some embodiments, a method of monitoring localized radiation exposure comprises monitoring changes in ultrasonic backscatter received from one or more implantable devices implanted in a subject being exposed to radiation. The radiation exposure and monitoring change in the ultrasonic backscatter can occur simultaneously. In some embodiments, the subject is a mammal, such as a human. In some embodiments, the location of the one or more implantable devices is determined. In some embodiments, the radiation exposure is suspended or re-targeted in response to changes in ultrasonic backscatter received form the one or more implantable devices. In some embodiments, the radiation is X-ray radiation, beta (electron) radiation, neutron beam radiation, carbon beam radiation, or proton beam radiation.

In some embodiments, there is a method of treating a solid cancer in a subject, comprising administering a radiation-based cancer therapy to a cancer and monitoring changes in ultrasonic backscatter received from one or more implantable devices implanted in the subject. The one or more implanted devices can be implanted adjacent to the cancer or on or within the cancer. The radiation exposure and monitoring change in the ultrasonic backscatter can occur simultaneously. In some embodiments, the subject is a mammal, such as a human. In some embodiments, administering the radiation-based cancer therapy includes targeting the radiation-based cancer therapy to the cancer. In some embodiments, the location of the one or more implantable devices is determined. In some embodiments, the radiation exposure is suspended or re-targeted in response to changes in ultrasonic backscatter received form the one more implantable devices. In some embodiments, the radiation is X-ray radiation, beta (electron) radiation, neutron beam radiation, carbon beam radiation, or proton beam radiation.

In some embodiments, there is a method of treating a solid cancer in a subject, comprising targeting the cancer with radiation (such as a X-ray radiation, beta (electron) radiation, neutron beam radiation, carbon beam radiation, or proton beam radiation); and monitoring off-target radiation exposure by transmitting ultrasonic waves from an interrogator comprising one or more ultrasonic transducers to one or more implantable devices comprising an ultrasonic transducer and a radiation-sensitive transistor implanted proximal to the cancer, and receiving from the one or more implantable devices ultrasonic backscatter encoding an amount of radiation exposed to the one or more implantable devices. In some embodiments, the method further comprises re-targeting the cancer with the radiation based on the amount of radiation exposed to the one or more implantable devices. The subject may be a mammal, such as a human. In some embodiments, the solid cancer is malignant. Exemplary cancers include a bone cancer, a breast cancer, a bladder cancer, a colorectal cancer, an eye cancer, a gastric cancer, a head and neck cancer, a renal cancer, a liver cancer, a lung cancer, a glioma, an ovarian cancer, a pancreatic cancer, a prostate cancer, a thyroid cancer, or a uterine cancer. In some embodiments, the method comprises determining the location of the one or more implantable devices or the movement of the one or more implantable devices.

Oncology Dust

Another application for the implantable device platform lies in the detection of cells, cellular localization, or the localization of a compound (such as a tumor marker). This includes, but is not limited to cancer cell recurrence or immune cell infiltrates that seek to attach cancer cells. Despite significant progress in cancer therapeutics, patients are largely incurable if cancer spreads. One scenario which is this common is when the cancer returns after initial treatment because aggressive surviving cells rapidly multiply and spread, or metastasize, to multiple areas of the body before they can be detected by imaging. A new system employing the implantable device platform addresses this problem head on, significantly improving patient care and clinical outcomes by leveraging recent advances in both the integrated circuit (IC) industry and targeted molecular agents to develop implantable, ultrasound-powered, sub-millimeter sensors placed within the patient at time of initial surgery. These sensors detect microscopic recurrent disease at its earliest stage (~1000-100,000 cells), prior to the development of distant metastases, guiding focal, definitive treatment, transforming an incurable cancer diagnosis into a potentially curable one.

In some embodiments, the integrated circuit of the implantable device includes a memory. The memory is configured to store information related to the encountered radiation, such as the time the radiation particle encountered the radiation, the energy of the radiation, or a directional vector of the radiation particle or wave. The implantable device can store the information in the memory for later transmittal to the interrogator.

Cancer recurrence is an important, and largely unaddressed, clinical problem because few effective treatment options exist: cells surviving initial therapy have high malignant potential, disseminating rapidly before they divide enough to be detected by existing imaging. In addition, they are resistant to common treatments while therapeutic intensity must be reduced due to cumulative dose-limiting toxicity from previous treatments. While tools to systemically detect microscopic tumor recurrence exist (e.g. circulating tumor cells), they lack the spatial localization necessary to guide curative focal treatment with precision surgical and radiation tools, such as radiosurgery, available in the clinic today. By detecting and spatially localizing the first ($10^4$-$10^5$) tumor cells to recur, recurrent disease can be identified and focally treated prior to the development of distant metastases, curing the patient. In patients with initially localized (non-metastatic) disease, tumor cells are most likely to recur in the area of the primary site of disease, but current imaging solutions are woefully inadequate for visualizing microscopic disease in vivo, missing the window of curative opportunity before cells metastasize, because imaging resolution is fundamentally limited to ~5 mm ($10^8$-$10^9$ cells) by 3 key factors: (1) Lack of molecular identification necessitates reliance on non-specific characteristics such as size, shape, or physiology requiring large numbers of tumor cells to produce a definitive signal. (2) Imaging is done from outside the body, far from the tumor cells, inherently limiting sensitivity and resolution. (3) Non-specific background masks the already weak tumor signal. In contrast, well established ex vivo laboratory-based microscopy techniques readily identify small foci of tumor cells using highly specific molecular labels and individual examination of small areas of tissue to achieve a high contrast ratio.

The implantable device platform described herein bridges the gap between ex vivo microscopic imaging and in vivo imaging by (1) using systemically injected targeted molecular agents to label tumor cells in vivo, (2) exponentially increasing sensitivity by placing sensors or a plurality of sensors just millimeters from the labeled tumor cells while, (3) reducing background from surrounding tissue by having individual sensors image only a small, localized area. As described herein, tumor cells can be labeled in vivo, and a sensor architecture enabling in vivo tumor detection can be obtained using an IC-based implantable sensor placed within the tumor bed or neighboring lymph node basins (areas at high risk for recurrence) at time of initial surgery or biopsy. In parallel with standard-of-care imaging, a radiolabeled molecule targeting cancer cells will be injected, labeling the tumor in vivo, signaling the presence of tumor to the implanted sensors, which then communicate via ultrasound when queried. In some embodiments, the system includes a network of sensors, covering the entire at-risk area.

Despite significant progress in cancer treatment, spanning imaging, targeted therapeutics and advanced surgical and radiation techniques, a significant number of patients have their cancer recur. With the caveat that there is significant variation between each cancer and the stage at which it was diagnosed, a gross estimate of recurrent cancer that is not cured is the ratio of the annual incidence to the death rate. Treatment of recurrent cancer is particularly challenging because cancer often metastasizes prior to detection, rendering the patient incurable. This results from 3 key factors: (1) Surviving cancer cells metastasize quickly. Having already completed several steps in the pathway to gaining metastatic potential, recurrent cancer cells require fewer cell divisions and consequently a shorter amount of time, to develop metastasis than de novo cancers. Recurrent cancer cells must be detected before they multiply and metastasize. (2) Current clinical imaging modalities are inadequate for imaging microscopic disease. Modern imagers, such as CT, PET, or MRI image externally, far the tumor cells, through the body, and do not leverage targeted molecular agents, reducing sensitivity. Consequently, identifying cancer is dependent on visualizing an anatomically abnormal mass, often with nonspecific physiologic changes (such as PET avidity). This limits resolution to ~1 cm, or 1 billion cells. Due to recurrent cancer cells starting from an advanced stage of progression to metastases, $10^9$ subsequent divisions to reach the imaging threshold often results in distant metastases. Recurrent cancer cells must be detected orders of magnitude below current imagers, and preferably about $10^5$ cells, 3-4 orders of magnitude below what is currently detectable. There is no known threshold for seeding distant metastases, and the threshold criteria for identifying tumor before spread will likely vary with each cancer and its biology. (3) Cells surviving initial therapy have high malignant potential, disseminating rapidly and require even more intensified therapy, yet patients are intolerant to significant retreatment due to cumulative toxicity from radiation, chemotherapy and surgery. To bridge the gap between detection limitations of external imagers and the need to detect cancer at the earliest possible sign of recurrence, blood tests have been used. Some tumors have protein markers that are used for tracking tumor growth or remission. For example, even a small (0.2 ng/ml) but persistently increasing PSA (prostate specific antigen) after surgery (radical prostatectomy) is considered evidence of tumor recurrence. Similarly, CA 19-9, CA 125 and CEA can be used for pancreatic, ovarian and colon cancer, respectively. Despite the advent of these tests, including newer techniques such as cell-free nucleic acids, or circulating tumor cells, that identify early cancer recurrence and prompt the initiation of systemic therapy, cure often necessitates intensive focal treatment directed to all tumor sites. It is this very lack of spatial localization of recurrent tumor cells that prevents focal curative therapy using available techniques such as radiosurgery. An example of this can be seen in the treatment of "oligometastatic disease" in select cancer types, whereby patients diagnosed with few (often <4) sites of confined metastatic disease (i.e. where all disease sites are known) are treated with curative intent using surgical resection or ablation of all sites of disease. Unfortunately, because the initial cancer recurrence is often below the resolution of current imaging, wide areas of tissue must be empirically re-treated, limiting treatment intensity, both contributing significant side effects and under-dosing the tumor. Of note, the area of recurrence may be missed entirely, contributing additional toxicity for no clinical benefit. Therefore, recurrent cancer cells must be precisely spatially localized so that targeted focal therapy can be administered. The possibility of microscopic distant metastatic disease at diagnosis, or dissemination of metastases prior to a local recurrence of $10^5$ cells, is a recognized limitation of this strategy.

Tumor recurrence in prostate cancer can be cured with in vivo monitoring and focal radiotherapy, ablation or resection. While this paradigm of localized tumor recurrence is prevalent across cancer types, it is particularly notable in prostate cancer with 50-70% of the 34,000 to 68,000 men diagnosed annually with high risk disease, having prostate cancer recur within 7 years of surgery. Fifty percent of these high-risk patients that recur within 3 years of surgery will develop, and die from, metastatic prostate cancer within 5 years. While prostate cancer has the advantage of having a highly specific marker (PSA) that identifies cancer recurrence after surgery, no method of spatial localization exists for microscopic disease. Due to the likelihood of a local (prostate bed) recurrence (25% of high risk patients) the standard treatment for a patient with rising PSA and no sign of distant metastases is 6-8 weeks of radiation therapy empirically administered a large area encompassing the prostate bed (and possibly pelvic lymph nodes), now occupied by healthy bladder and rectum, requiring a low (and potentially sub therapeutic) dose to avoid significant toxicity. While this has been shown to reduce cancer recurrence, and increase survival from prostate cancer, the area of recurrence can be missed entirely. Not unsurprisingly, the outcomes remain poor, with only 40% of patients cancer free 4 years later, largely due to the inability to localize and definitively treated the area of tumor recurrence. In addition, a significant amount of clinical data shows that prostate cancer can be effectively treated with high dose focal radiation with stereotactic body radiotherapy (SBRT) or high dose rate brachytherapy (HDR). Therefore, recurrent cancer can be cured with high dose, focal radiation therapy (or salvage surgery or ablation), but must be identified, localized and definitively treated in the short window of time before it disseminates, necessitating a new approach to cancer monitoring.

Figure 15A:
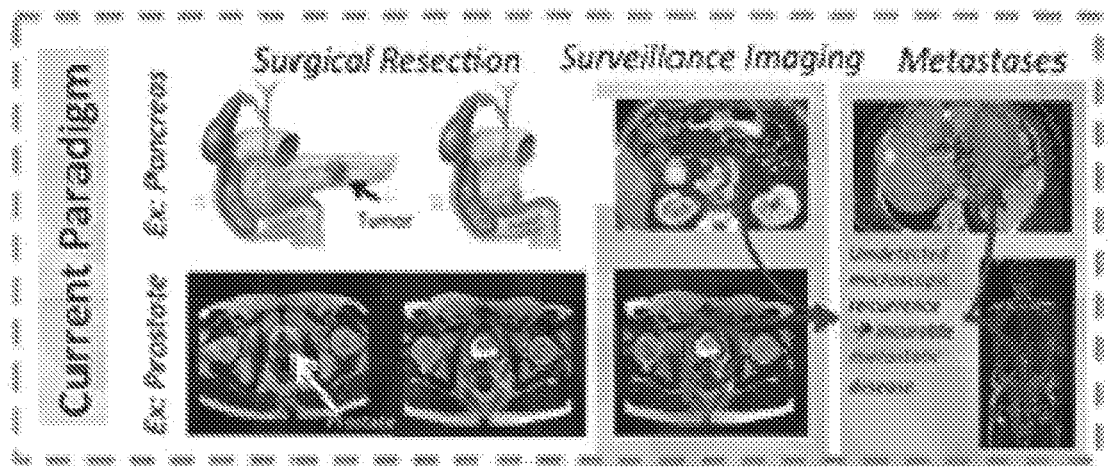
FIGS. 15A and 15C illustrate previous methods of monitoring a subject for cancer recurrence by periodically imaging the subject. Relying on imaging techniques to monitor a subject often results in smaller cancers going unnoticed, which can lead to a high rate of cancer metastasis.
Figure 15B:
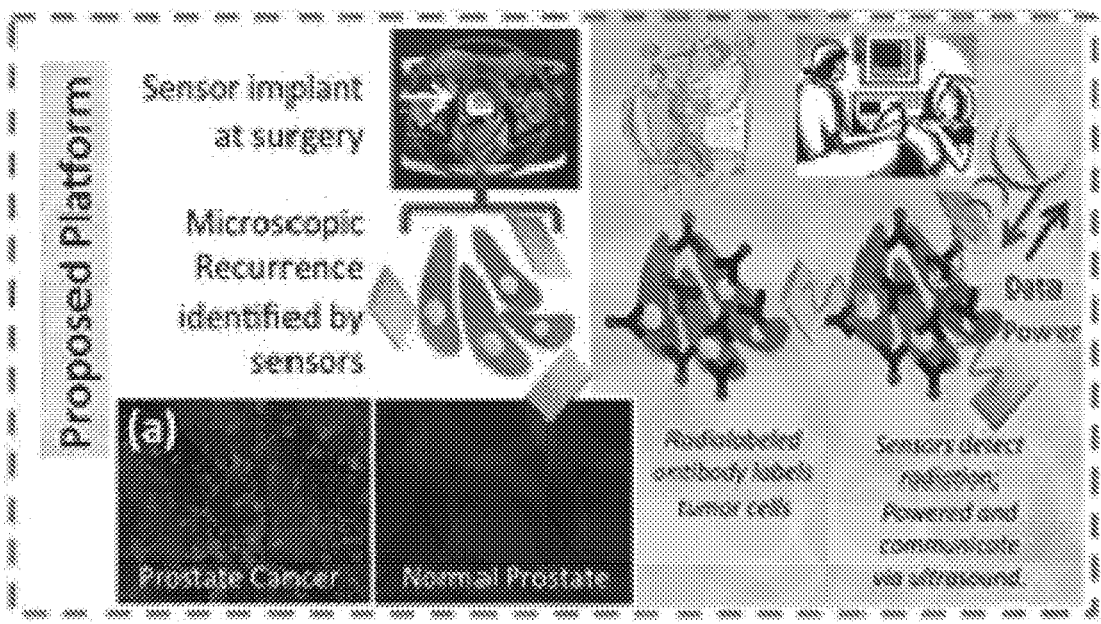
FIGS. 15B and 15D illustrate a method of monitoring a subject for cancer recurrence. One or more implantable devices are implanted in the subject at or proximal to the location of an excised cancer. The implantable devices include one or more pixels comprising a radiation-sensitive diode, or two or more arrays comprising a plurality of pixels. A radioactive molecular marker can be administered to the subject, which specifically binds a recurrence of the cancer. The molecular marker emits radiation, such as beta, or gamma particles, which are detected by the one or more implantable devices and reported using ultrasonic backscatter. The location of the cancer can be determined by analyzing the directional vectors of the emitted radiation. The detected cancer recurrence can be detected at a smaller size than relying on imaging to monitor cancer recurrence. A detected cancer recurrence can therefore be excised or ablated, preferably prior to metastasis.

Strategy for an Implantable Ultrasound-Powered Cancer Surveillance Network. The implantable platform is designed to work synergistically with established cancer surveillance guidelines, as shown in FIG. 15B. At the time of initial surgery or biopsy, sensors are implanted in areas at highest risk for cancer recurrence during, including the tumor bed and adjacent lymph node basins. At each regularly scheduled clinic follow up, the patient will be injected with a targeted ligand to their specific cancer, conjugated to a radiolabel, which communicates the presence of tumor to the sensor. The sensor gathers the signal, determining the location of the tumor cell, and communicates wirelessly to the clinician via ultrasound, achieving detection and spatial localization of the earliest signs of cancer recurrence, and facilitating targeted focal therapy.

To achieve spatial localization of microscopic cancer recurrence, (1) a targeted biologic that identifies recurrent cancer cells in vivo was developed; and (2) the platform of sub-millimeter sized, implantable sensors was implanted to detect labeled tumor cells. Leveraging the millimeter-proximity of sensors to tumor cells, a high sensitivity can be achieved and small numbers of recurrent cells can be detected.

In one aspect, the system enables spatial localization of early, curable, microscopic tumor recurrence via a platform that synergistically combines an implantable sensor network (which increases sensitivity via proximity to the tumor) with a locally signaling antibody (which adds high molecular specificity while mitigating background). The sensor can be a completely passive, biocompatible device: it is powered by ultrasound and uses the same for transmitting the location of the recurrent cancer. In this way, an implanted network can function for years within the patient. To translate the proven techniques of molecular identification of tumor cells into an in vivo imaging platform, the existing, and growing, armamentarium of targeted molecular agents can be leveraged, and a wholly new method of imaging is introduced: implantable networks of sensors within the patient. Placing the sensors inside the patient in close proximity to the tumor exponentially increases sensitivity and virtually eliminates the effects of scatter, increasing resolution. To mitigate the problem of background binding to the far more numerous surrounding normal tissue cells, each sensor only "sees" (or senses) a small area of surrounding tissue.

In one aspect, the technique involves the integration of antibodies radiolabeled with beta-particles which only travel a specified distance (<1 cm), dramatically reducing the background. The radiolabel is small, preserving the functionality of the antibody, requires no external power, and mitigates the issue of bio-fouling. The small additional dose of radiation is negligible to the radiation dose often received during initial treatment, adding minimal incremental risk from exposure.

To ensure clinical integration, the platform seamlessly integrates with standard state of the art clinical surveillance imaging, which generally includes imaging roughly every 3-6 months over the course of 5 years for the majority of cancers. In prostate cancer, an ultra-sensitive PSA test is performed, that can identify cancer recurrence. The system can include an implantable sensor network synergistically coupled with systemically injected targeted molecules that binding to tumor cells. In terms of size, the sensors may be very small, and completely passive to eliminate the need for a battery, limiting both size and longevity of the implant. The need for a battery is eliminated under this approach, relying on a completely passive sensor approach. Even if scar tissue forms on the sensor, the high energy beta particles will travel straight through the scar tissue. In terms of communication with the implanted devices, a method of wireless power transfer and communication via ultrasound enables a clinically acceptable mode of interrogation.

Integrated Circuits with sub-Micron Features Provide Sensitive Detection Arrays, Signal Processing, and Communication. While a variety of radiation sensing technologies exist, a modern computer chip, or integrated circuit (IC or CMOS complementary metal oxide semiconductor) technology which allows complex sensors, signal processing and communication circuitry to be fabricated with feature sizes less than a micron, can be leveraged. This enables sensing of the radioactivity from the neighboring labeled tumor cells, on-chip processing to determine the location of recurrent cancer, and communication to the clinician within a sub-millimeter form-factor. An on-chip integrated diode (e.g., with a 1 µm depletion region) converts each incident beta particle to ~150 electrons, which are integrated onto the photodiode parasitic capacitance producing a voltage change following the expression, $V=q/C$, where V, q, and C are the voltage, generated charge, and capacitance, respectively. Since the charge generated is fixed for each beta-particle, a small capacitance is desirable, further necessitating an integrated circuit, where the parasitic capacitances on minimum sized diodes (sub-micron) are on the order of $10^{-15}$ farads (F), several magnitudes of order less than can be achieved with discrete components ($10^{-12}$-$10^{-9}$ F).

A Wireless, Ultrasound-Based Interface Enables a Small Form Factor and Long Implantable Lifetime: To enable the small size necessary for implanting multiple sensors within the body, the need for a battery is preferably eliminated. Instead, a clinically available ultrasound for both power transmission to the sensor, and reading data from it, can be used. The elimination of a battery also enables the sensor to have a functional lifetime far exceeding the 5 years needed for surveillance in most cancers. Further, the small size of the implantable device allows implantation through a biopsy needle.

Design and Fabrication of an IC Radiation Detector Array: In some embodiments, the implantable device includes the following properties to spatially identify and localize a tumor focus of 100,000 cells for a period of 5 years: (1) Minimizing device size: The size of the physical device must be smaller than the volume of tissue it senses. For a goal of a device 10× smaller than the sensed volume, a 8 mm range from the sensor (approximate distance that P32 travels) translates to a <800 um device. In smaller implementations, e.g., <100 um, the device itself may have virtually no physical burden on the patient. (2) Passive power and data transfer using ultrasound: Cancer surveillance often spans at least 5 years, and therefore the device preferably functions for 5 years or more. Since a battery limits the functional lifetime of the device, it can be eliminated entirely. Using a proven ultrasound-based platform, power can be transferred to the device, and data can be gathered from it. Furthermore, the elimination of a battery allows a significant reduction in device size. (3) Angle selective sensing: A tumor focus of $10^5$ cells at the edge of the detection region (8 mm from the sensor), with a tumor-to-normal tissue antibody binding ratio of 35,000:2,000, or 17, results in a signal to background ratio (SBR) of radiation of $8\times10^{-6}$, making a tumor focus challenging to detect. By selectively imaging only the solid angle of tissue subtended by the tumor, the SBR is increased to $10^{-2}$. Further features of the system can include: (4) Detection of single beta-particle emission events. To achieve angle sensing of incoming beta particles, a single, near simultaneous discrete event can be recorded on two back-to-back arrays allowing the incident angle to be calculated. (5) Minimizing diode size: A beta particle will generate approximately 150 electron/hole pairs in a photodiode with a 1 µm depletion region. This charge is converted to a voltage signal for processing and readout by integrating it on a capacitor. Following the relationship, $Q=CV$, the largest voltage change requires the smallest capacitance, and thus the smallest photodiode. An integrated circuit approach can be used, whereby submicron features sizes are readily available. For example, a 0.18 μm process with a minimum photodiode size of 0.86 μm×0.86 μm can be used, resulting in a parasitic capacitance of 1.2 fF and a dark current of 73 aA. Pixel-level circuitry will be kept at minimum size, adding only ~0.8 fF of gate capacitance. With this minimum-sized photodiode, the change in voltage signal with a single beta-particle, generating 150 electron-hole pairs is ~20 mV. With an integration time of <20 uS, there is less than a 1% chance of any dark current; thus with megahertz clock frequencies, easily achieved in modern CMOS processes, there is no background from the sensor itself. Therefore, it is preferable to detect a 20 mV change on a photodiode with a sampling frequency of approximately 1 MHz. To increase robustness, and leveraging detection of a single event, each beta particle incident on a diode can be converted to a digital signal for processing. (6) Increasing detector speed: The integration time also needs to be less than the time between incident beta particles such that each simultaneous event detected by both back-to-back arrays can be assumed to be from the same beta particle. With an activity of P32 of 9,131 Ci/mmol, and 35,000 antibodies/per cancer cell, and 2,000 antibodies/cell background, the flux on a minimum sized (0.86 um×0.86 um) photodiode is 100×100 um sensor is 170 beta-particles/second from the background. When angle-selective imaging is used, the background from is one event every 30 seconds. The signal from the tumor, located at the edge of the detection range (8 mm), and therefore representing the worst-case scenario, is 1 event every 40 seconds. During a 30 minutes interrogation, 45 beta particles from the tumor would be measured, and the background from the same solid angle would be 190, with a noise floor of 15 events.

Angle selectivity with back-to-back approach: MATLAB can be used to simulate and verify the improved sensitivity obtained by determining the angle of incidence of each beta particle, to unmask the tumor from the background. Furthermore, an algorithm (which may be coded in VERILOG, for example), which can be implemented in digital circuitry, can be used to derive the angle from the location of simultaneous events on each array. The arrays may be designed such that they can be affixed to a PCB back to back, and run from the same power supply and clock, so that the location of simultaneous events on each array can be sampled. On-chip digital circuitry will determine the angle of incidence of each event, and store it in a counter, creating a histogram of incident angles.

In some embodiments, the implantable device is useful for monitoring or identifying growing or recurrent cancer. The implantable device can include a miniaturized ultrasonic transducer (bulk piezoelectric transducer, a PMUT, or a CMUT) and one or more arrays comprising a plurality of radiation-sensitive pixels. In some embodiments, the array is coated with a scintillator material. Exemplary scintillator materials include $LaBr_3(Ce)$, $Cs_2LiLaBr_6(Ce)$, NaI(TI), CsI (Na), $Lu_{1.8}Y_{0.2}SiO_5$, $CdWO_4$, $CaF_2$, CsI(TI), bismuth germinate (BGO), $Y_3Al_5O_{12}(Ce)$, CsI, $BaF_2$, and ZnS(Ag). One or more implantable devices can be implanted near a tumor or the location of a previously excised tumor in a subject. A radiolabeled molecular probe (such as an antibody) that specifically binds to a marker on the cancer can be administered to the subject. If the cancer is present, the molecular probe will bind to the cancer and the radiolabel will emit radiation. The radiation is then detected by the implantable device, which can report the detected radiation to an interrogator using ultrasonic backscatter waves.

Figure 15C:
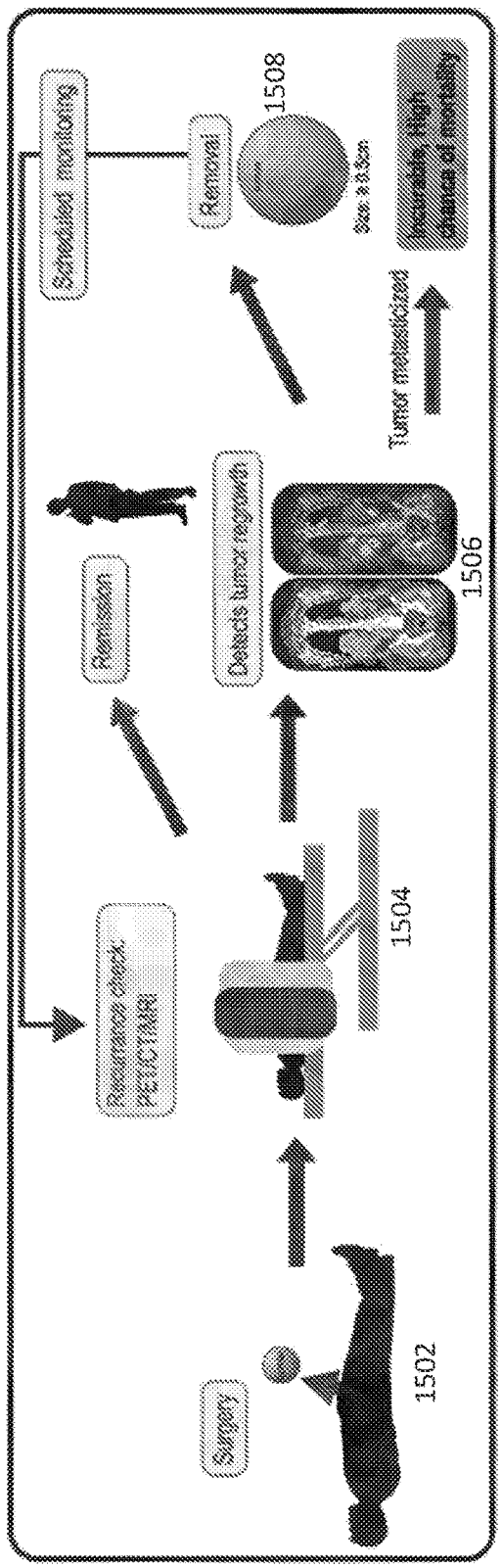
Figure 15D:
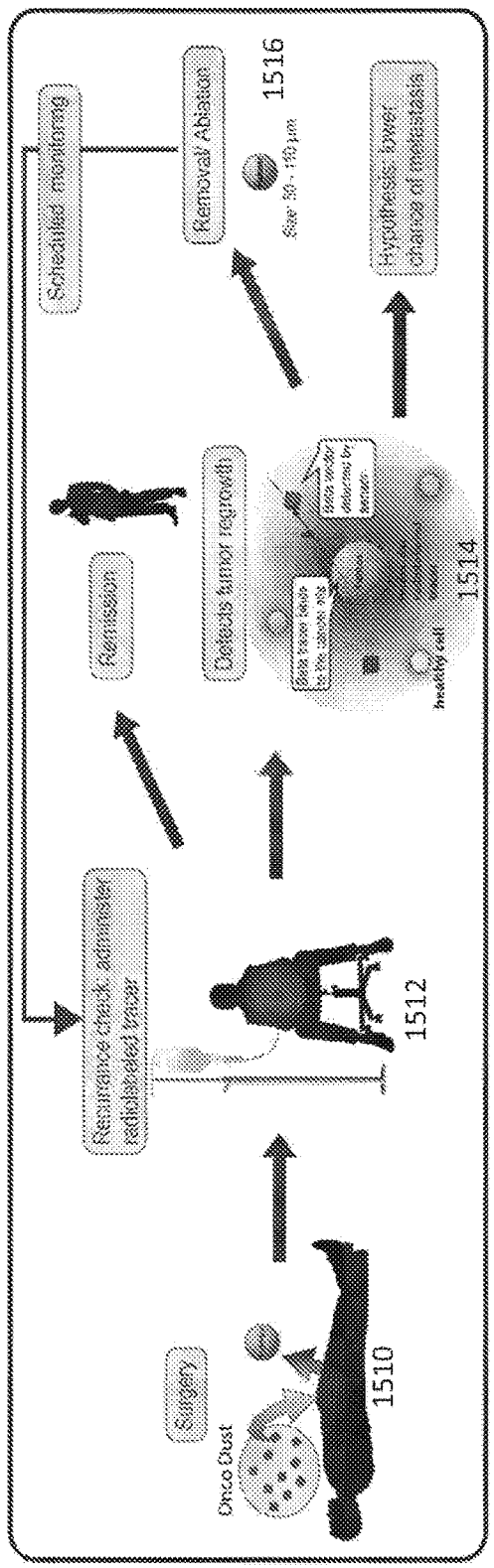

FIGS. 15C and 15D compare previously known methods of monitoring tumor recurrence (FIG. 15C) with an exemplary method using an implantable device described herein (FIG. 15D). As shown in FIG. 15C, at step 1502, surgery can be performed on a subject to excise a tumor. After a period of time, recurrence of the tumor is checked at step 1504 using an imaging technique (such as PET, CT, or MRI scanning). The images taken in step 1504 can be analyzed at step 1506 to detect tumor regrowth. Analysis of images to locate tumor recurrence is challenging, and small tumors are frequently unobserved. If tumor regrowth is observed, the tumor can be excised (step 1508), although the observed tumor is generally large (such as over 0.5 cm, or about $10^9$ cancer cells. Metastasis of the tumor is more likely with a larger tumor, which results in a higher risk of patient mortality. The patient can continue to be monitored by periodic imaging methods to locate tumor regrowth. As shown in FIG. 15D, at step 1510, the tumor is excised and implantable devices as described herein are implanted in the subject near the site of the excised tumor. After a period of time, a tracer comprising a radiolabeled molecular probe is administered to the subject, as shown at step 1512. The molecular probe can bind to a cancer regrowth and emit radiation, which is detected by the implantable device and reported to an interrogator, as shown at step 1514. If radiation is detected, it is inferred that tumor regrowth has occurred. Further, if the implantable device includes two or more arrays, the location of origin of the radiation can be determined. Since the origin of the radiation is the location of the cancer regrowth, the location of the cancer regrowth is known and the tumor regrowth can be excised (step 1516). Detection of the tumor regrowth is more sensitive than the imaging techniques previously used (see FIG. 15C), and smaller tumor growths can be detected (for example, as small as 50 μm, or about $10^4$ cells).

In some embodiments, the implantable device is used to detect the recurrence of a cancer. In some embodiments the cancer is a metastatic cancer. Exemplary cancers include solid cancers, such as bone cancer, breast cancer, bladder cancer, colorectal cancer, eye cancer, gastric cancer, head and neck cancer, renal cancer, liver cancer, lung cancer, a glioma, ovarian cancer, pancreatic cancer, prostate cancer, thyroid cancer, or uterine cancer, Brain cancer, spinal cancer (such as spinal cord cancer or spinal canal cancer), colon cancer, cecal cancer, gall bladder cancer, testicular cancer, sarcoma, rectal cancer, anal cancer, skin cancer, or a metastatic cancer. The molecular probe is specific to a tumor marker. Exemplary tumor markers are prostate specific membrane antigen (PSMass.), CA 19-9, CA125, carcinoembryonic antigen (CEA), or circulating tumor DNA. Other tumor markers are known in the art. The molecular probe can comprise an antibody or an antibody mimetic (such as an affibody or an aptamer), which binds to the tumor cell marker. In some embodiment, the molecular probe comprises a nucleic acid that specifically binds to a nucleic acid of interest, such as circulating tumor DNA. The molecular probe can also include a radiolabel, such as phosphorus-32 (P-32) or fluorine-18 (F-18). In some embodiments, the molecular probe is fluorodeoxyglucose. The radiolabel can emit radiation, such as beta-particles or gamma waves, which is detected by the implantable device.

In some embodiments, the implantable device comprises a miniaturized ultrasonic transducer (bulk piezoelectric transducer, a PMUT, or a CMUT) and one or more arrays comprising a plurality of radiation-sensitive pixels (which include one or more radiation sensitive elements (such as a diode, a transistor, or flash memory cell)). The arrays comprising a plurality of radiation-sensitive pixels are similar to the arrays described above. When radiation encounters the radiation-sensitive diode, one or more electron-hole pairs can be generated, thereby generating a transient current. The number of electron-hole pairs is a function of the energy of the incident radiation as well as other factors, including the properties of the interface materials. A transient electrical current can therefore be generated, with the amplitude of the current reflecting the energy of the radiation. The array can include a CMOS front end, which can transmit an electrical signal to the ultrasonic transducer the location of the pixel within the array (i.e., the "pixel address") that was excited by the radiation. In some embodiments, the signal encodes the energy of the radiation. Cycling can be fast enough such that only a single radiation particle or wave is detected by the array at a time. This signal is then converted into ultrasonic backscatter waves emitted by the implantable device and received by the interrogator. Therefore, the radiation-sensitive pixel allows for determination radiation (or counts of radiation), and optionally the energy of the radiation. In some embodiments, the array comprises 2 or more pixels (such as 8 or more, 16 or more, 32 or more, 64 or more, 125 or more 250 or more, 500 or more, 1000 or more, 2000 or more, 4000 or more, 8000 or more, 16,000 or more, 30,000 or more, or 60,000 or more pixels). An exemplary array with a CMOS front end and 256×256 pixels is illustrated in FIG. 11. Exemplary radiation-sensitive pixels are shown in FIGS. 12A-C.

In some embodiments, the implantable device comprises two or more arrays comprising radiation sensitive pixels. In some embodiments, the arrays are disposed in parallel planes in a stacked configuration (that is, the parallel arrays overlap in a transverse direction). In some embodiments, the arrays are parallel are offset. In some embodiments, the arrays are not parallel. By stacking the arrays, a directional vector of the radiation can be determined based on the pixel address of a first pixel on a first array and a second pixel on a second array, wherein both the first pixel and the second pixel encounter the radiation. Determining the directional vector of the incident radiation, for example radiation applied to a cancer during radiation treatment, can allow the radiation to be retargeted toward the cancer and away from the implantable device. In some embodiments, the arrays are separated by about 0.02 mm or more (such as about 0.05 mm or more, about 0.1 mm or more, about 0.2 mm or more, about 0.5 mm or more, or about 1 mm or more). In some embodiments, the arrays are separated by about 2 mm or less (such as about 1 mm or less, about 0.5 mm or less, about 0.1 mm or less, or about 0.05 mm or less). In some embodiments, the arrays are separated by about 0.02 mm to about 1 mm (such as about 0.05 mm to about 0.5 mm, about 0.1 mm to about 0.2 mm, or about 0.1 mm). An exemplary embodiment of an implantable device comprising two arrays is shown in FIG. 13. The implantable device includes a first array 1302 and a second array 1304. Each of the arrays includes a plurality of radiation-sensitive pixels and an ASIC. The first array 1302 and the second array 1304 are connected to a miniaturized ultrasonic transducer 1306. Radiation 1308 (such as a proton beam) can be targeted to a location near the implantable device, but off-target radiation may encounter one or more pixels in the array. When radiation encounters a pixel in one or both arrays, a signal is transmitted to the ultrasonic transducer 1306. The ultrasonic transducer 1306 converts the electrical signal to ultrasonic backscatter, and the ultrasonic waves are transmitted to an interrogator 1308. The interrogator 1308 also transmits ultrasonic waves (carrier waves) to the implantable device, which can be used, for example, to power the ASICS on the arrays.

Figure 16A:
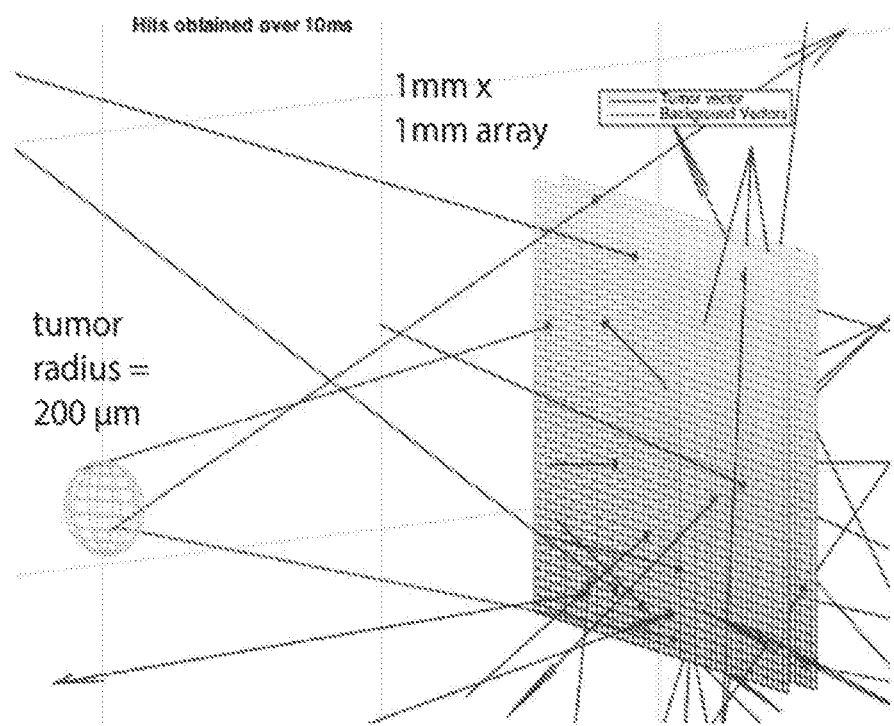
FIG. 16A shows a Monte Carlo simulation of two stacked arrays exposed to radiation from a radiolabeled tumor (200 μm radius) and background radiation. The stacked arrays are separated by 1.1 mm
Figure 16B:
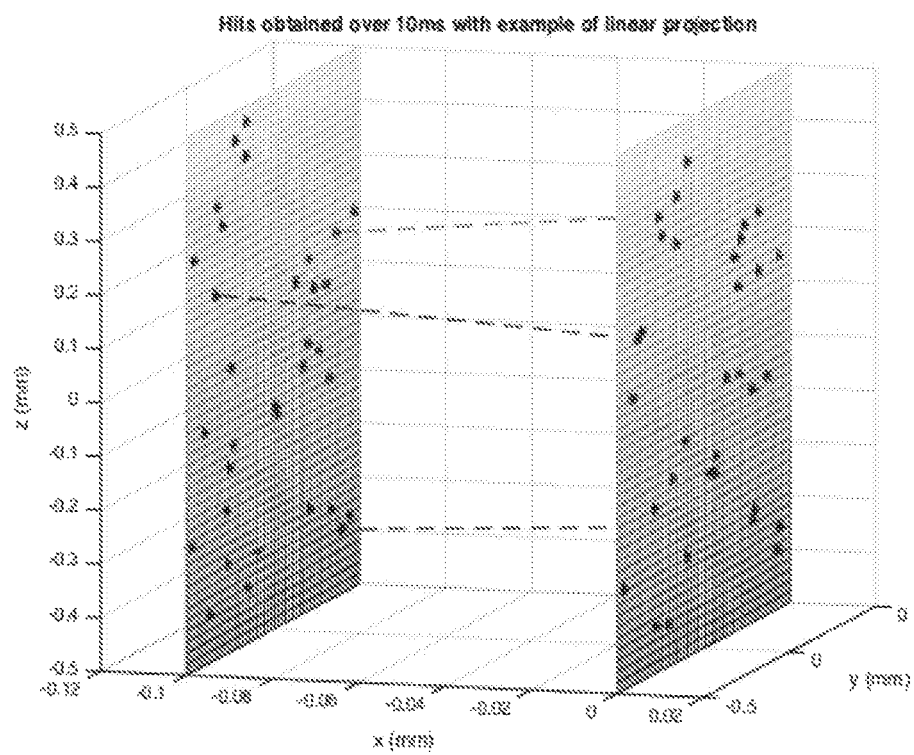
FIG. 16B shows two stacked arrays with directional vectors illustrated for radiation detected by both arrays originating from the radiation source (the radiolabeled tumor). When an event is detected at both sensors (arrays) at the same time, it is possible to determine pairs of hits and extrapolate a vector from the data.

FIG. 16A shows a Monte Carlo simulation of two stacked arrays separated by 0.1 mm, the arrays comprising a plurality of radiation-sensitive pixels. The simulation was written using a P-32 as the model radioisotope and takes into account the energy emission spectrum of P-32, radiation energy losses in tissue, stopping power of beta particles in silicon, and electron hole pairs generated in a silicon depletion region. The simulation indicates that it is possible to detect hotspots of directional vector information by integrating signal over a matter of seconds or sub-seconds. Radiation originating from a 200 µm (radius) radiolabeled tumor is emitted, encountering a first pixel on the proximal array (that is, closer to the tumor) and then a second pixel on the distal array. When an event (i.e., a radiation encounter) is detected at both sensors at approximately the same time, the pair of triggered pixels can be extrapolated to determine the directional vector of the radiation. Background radiation can also encounter one or more arrays, as shown. The background radiation can be filtered out, either due to low energy of the radiation encountering a pixel or by the directional vector of the radiation, as discussed below. The radiation shown in FIG. 16A occurs during a 10 ms simulation period. FIG. 16B shows a zoomed-in view of the two arrays shown in FIG. 16A, with radiation direction vectors between the two arrays illustrated. The directional vector is determined based on the pixel address of the pixels that encounter the radiation in the two arrays.

Figure 17A:
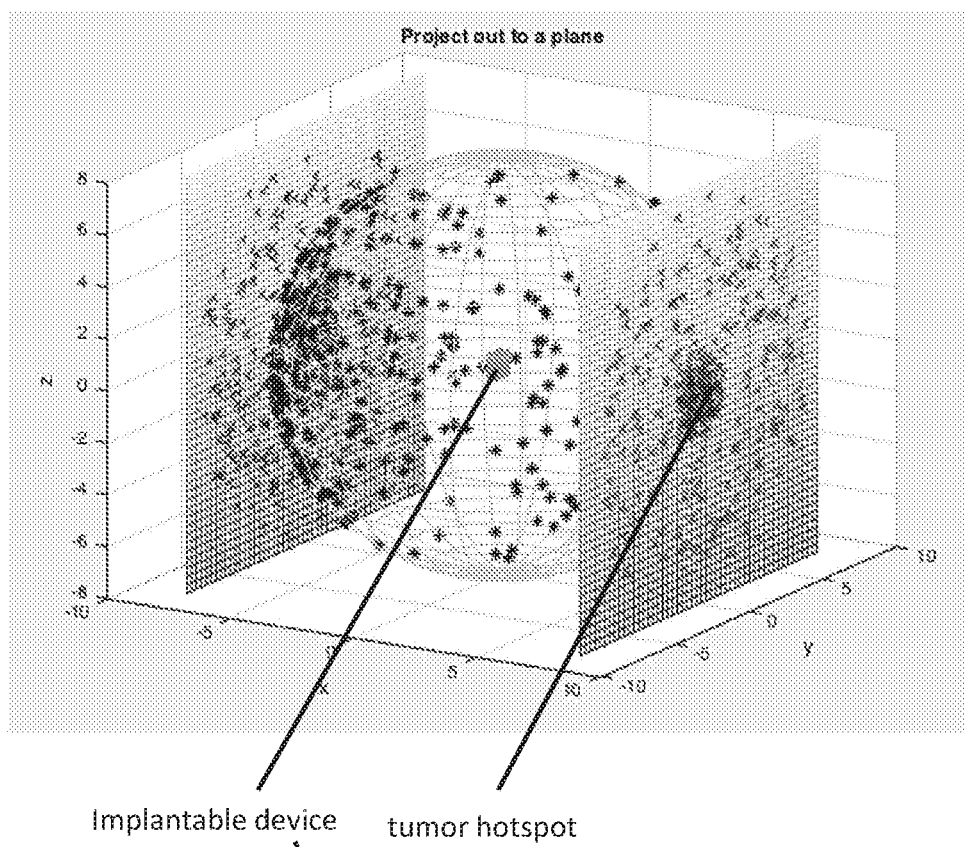
FIG. 17A shows directional vectors determined from radiation emitted from a radiation source extrapolated into a y-z plane in both the +x and −x dimension. The radiation source emits radiation, which is detected by the pair of stacked arrays (comprising pixels comprising a radiation-sensitive diode) on the implantable device. A hotspot is located in the +x direction, indicating the location of the radiation source (i.e., the radiolabeled cancer).
Figure 17B:
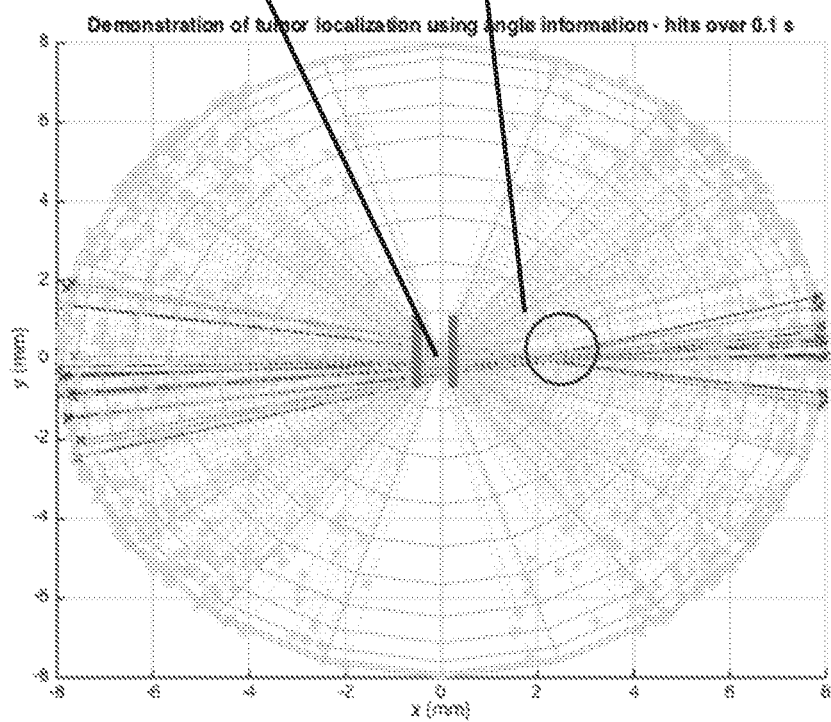
FIG. 17B shows a two-dimensional view of the extrapolated directional vectors shown in FIG. 17A. Hotspots create a double conic shape with highest concentration of intersections at tumor location (indicated in the circle). Modern clustering algorithms can be used to estimate the tumor's location.

The extrapolated direction vectors of the radiation can be extrapolated, as shown in FIGS. 17A and 17B. FIG. 17A presents a three-dimensional view, and FIG. 17B presents a two dimensional view. The arrays of the implantable device in FIG. 17B are exaggerated for clarity. The data is simulated for a 200 µm (radius) radiolabeled tumor using stacked arrays separated by 0.1 mm. The data was collected for 100 ms, with tumor hits multiplied by a 10-fold for clarity. The sensor is located in the center of the extrapolation sphere. A hotspot creates a double conic shape with highest concentration of intersections at the tumor location (indicated in the circle in FIG. 17B.). Clustering algorithms can be used to estimate the tumor's location and filter out the background radiation.

Figure 18A:
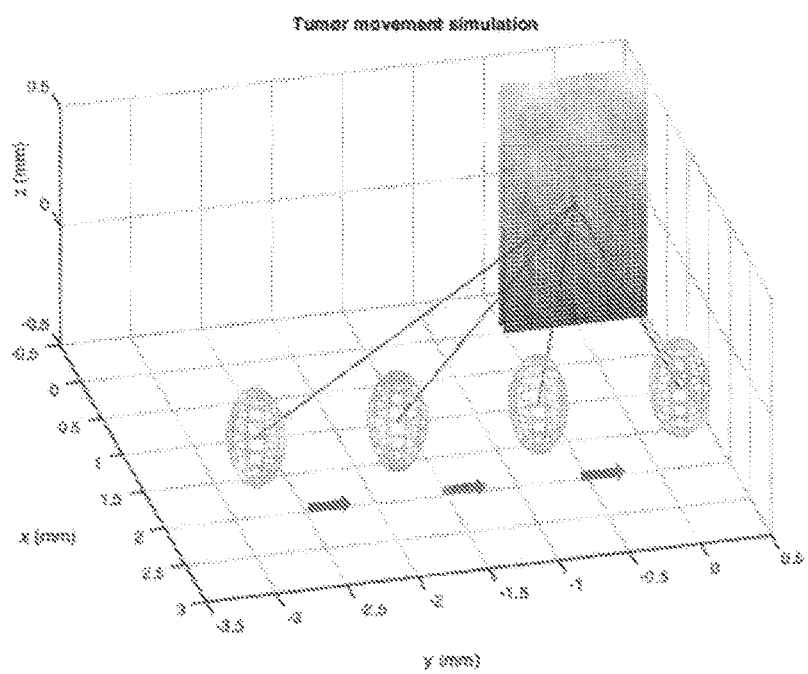
FIG. 18A illustrates simulated tracking of a moving radiation source (e.g., a radiolabeled cancer) over a period of time. The location of the radiation source can be determined at a plurality of time points, and movement can be extrapolated.
Figure 18B:
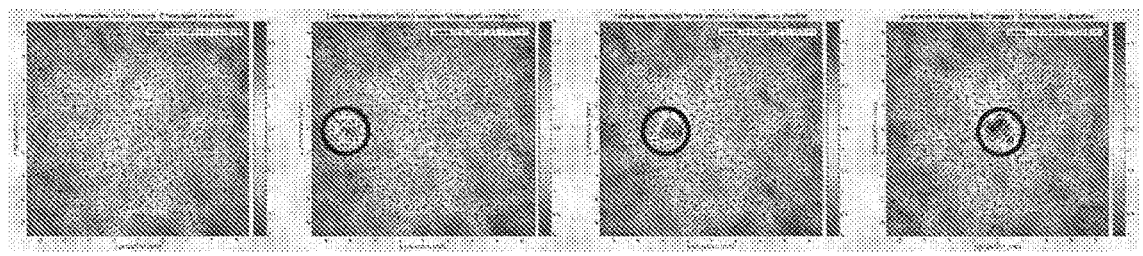
FIG. 18B shows the hotspot (within circle) of intersecting directional vectors in the +x direction of the radiation source moving in the +y direction.
Figure 18C:
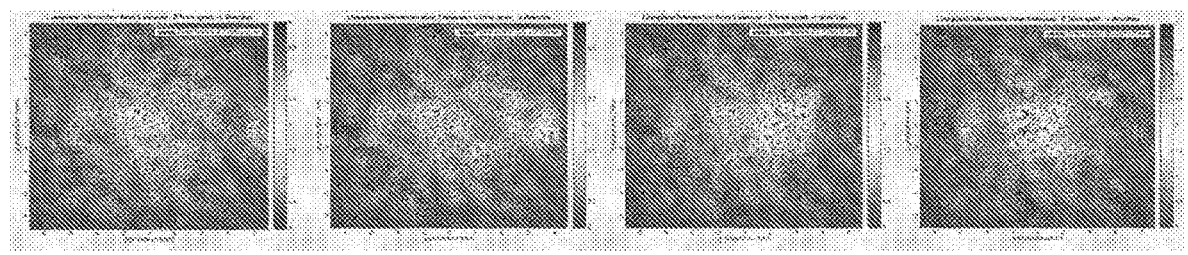
FIG. 18C shows that no hotspots are generated in the −x direction. The location of the radiation source is therefore confirmed in the +x direction by the absence of a hotspot in the −x direction.

As described, the location of a radiolabeled tumor can be detected. In some embodiments, movement of a tumor is tracked over a period of time, such as about 30 seconds or more, about 60 seconds or more, about 5 minutes or more, about 15 minutes or more, about 30 minutes or more, about 60 hours or more, about 2 hours or more, about 4 hours or more, about 6 hours or more, about 12 hours or more, or about 24 hours or more. In some embodiments, the movement of the tumor is tracked over about 48 hours or less (such as about 24 hours or less, about 12 hour or less, about 6 hours or less, about 3 hours or less, about 1 hour or less, about 30 minutes or less, about 15 minutes or less, about 5 minutes or less, about 1 minute or less, about 30 seconds or less, or about 5 seconds or less). In some embodiments, the movement of the tumor is tracked for about 0.1 mm or more, about 0.2 mm or more, about 0.5 mm or more, about 1 mm or more, about 2 mm or more, about 5 mm or more, or about 10 mm or more. In some embodiments, movement of the tumor is tracked over about 20 mm or less, about 10 mm or less, about 5 mm or less, about 2 mm or less, or about 1 mm or less. In some embodiments, the cancer is a metastatic cancer. Tracking the cancer over a period of time can allow for re-targeting a cancer therapy (such as proton beam therapy). FIG. 18A illustrates simulated tracking a radiolabeled cancer over one second along the y-axis for about 3 mm using an implantable device comprising two or more arrays comprising a plurality of radiation-sensitive pixels. FIG. 18B shows hotspots (highlighted by a circle) indicating the location of the cancer in a y-z plane projected in the +x directions (that is in the direction towards the moving tumor). FIG. 18C shows an absence of hotspots in a y-z plane projected in the −x direction, indicating that the moving tumor is located in the +x direction relative to the implantable device.

In some embodiments, the implantable device comprises two or more arrays, each array comprising a plurality of pixels, each pixel comprising a radiation-sensitive diode configured to generate a transient electrical current upon encountering radiation; an integrated circuit configured to receive the electrical signal and modulate a current based on the received electrical signal; and an ultrasonic transducer configured to receive the modulated current and emit an ultrasonic backscatter based on the received modulated current. In some embodiments, the implantable device includes no more than two arrays. In some embodiments, the arrays are stacked. The two or more arrays are preferably separated by about 1 mm or less (such as about 0.5 mm or less, or about 0.2 mm or less). Preferably, the implantable device is miniaturized, and has a length of about 5 mm or less (such as about 4 mm or less, about 3 mm or less, about 2 mm or less, or about 1 mm or less) in the longest dimension.

The implantable device can be configured to emit ultrasonic backscatter that encodes the pixel address of one or more pixels that encounter a radiation particle or wave. In some embodiments, the implantable device is configured to analyze the pixel addresses of two or more pixels that encounter a radiation particle or wave to determine a directional vector for the encountered radiation. In some embodiments, the implantable device is configured to emit ultrasonic backscatter that encodes the directional vector (for example by the integrated circuit transmitting a digitized signal to the transducer encoding the directional vector). In some embodiments, the implantable device is configured to determine a location of the radiation source (relative to the implantable device) based on a hotspot of a plurality of intersecting directional vectors. In some embodiments, the location of the radiation source is encoded by ultrasonic backscatter emitted by the implantable device.

The radiation particles or waves that encounter the radiation-sensitive pixels in the array of the implantable device can originate from a radiation source. In some embodiments, the radiation source is a radiolabeled cluster of cells, such as a radiolabeled cancer. In some embodiments, the radiolabeled cluster of cells (such as the cancer) has a radius of about 5 mm or less, about 2 mm or less, about 1 mm or less, about 0.5 mm or less, about 0.3 mm or less, about 0.2 mm or less, or about 0.1 mm or less. In some embodiments, the cluster of cells is radiolabeled by binding a radiolabeled molecular probe (such as a P-32 or F-18 labeled molecular probe) to the cluster of cells. For example, the molecular probe can comprise an antibody or antibody mimetic that specifically binds to a molecule expressed on the surface of the cells within the cluster of cells, such as an overexpressed tumor marker.

In one aspect, there is provided a method of detecting radiation or determining the location of a radiation source. Ultrasonic waves are received by one or more implantable devices comprising an ultrasonic transducer, an integrated circuit, and two or more stacked arrays comprising a plurality of pixels. Each of the pixels includes a radiation-sensitive diode configured to generate a signal upon encountering radiation. The ultrasonic waves power the one or more implantable devices. Energy from the ultrasonic waves is converted into an electrical current, which is transmitted to the integrated circuit. One or more of the pixels is exposed to a radiation particle or radiation source. The radiation source may be, for example, a radiolabeled cluster of cells, such as a cancer. In some embodiments a first pixel on a first array and a second pixel on a second array are exposed to the same radiation particle or wave. The pair of pixels that encounter the same radiation particle or wave can be used to determine a directional vector. It can be determined that the two pixels encountered the same radiation particle or wave based on the temporal proximity of the encounter. A signal indicating that a diode has been exposed to a radiation particle or radiation wave is transmitted to the integrated circuit, which modulates the electrical current based on the received signal. The signal can include a pixel address of the diode that encountered the radiation particle or wave. The modulated electrical current is transduced into an ultrasonic backscatter that encodes the radiation exposure. The ultrasonic backscatter can encode, for example, the pixel address of the one or more pixels that encountered the radiation particle or wave. In some embodiments, the integrated circuit comprises a processor that can determine a directional vector of the radiation particle or wave based on the pixel addresses of a pair of pixels that encountered the same radiation particle or wave. In some embodiments, the ultrasonic backscatter encodes the directional vector of the radiation particle or wave. In some embodiments, the integrated circuit is configured to determine the location relative to the implantable device of the radiation source based on a plurality of directional vectors from a plurality of radiation particles or waves emitted by the radiation source. In some embodiments, the ultrasonic backscatter encodes the relative location of the radiation source. The ultrasonic backscatter is emitted to an interrogator comprising one or more transducers configured to receive the ultrasonic backscatter.

In one aspect, there is a method of monitoring a subject for recurrence of a solid cancer. In some embodiments, the subject is a mammal, such as a human. The solid cancer can be, for example a bone cancer, a breast cancer, a bladder cancer, a colorectal cancer, an eye cancer, a gastric cancer, a head and neck cancer, a renal cancer, a liver cancer, a lung cancer, a glioma, an ovarian cancer, a pancreatic cancer, a prostate cancer, a thyroid cancer, or a uterine cancer. The cancer may have been previously excised, and one or more implantable devices can be implanted at or near the location of the previously excised cancer. The method includes administering to the subject a radiolabeled molecular probe that emits a radiation particle or wave and that specifically binds to the solid cancer. The radiolabeled molecular probe can include an antibody or an antibody mimetic, which can bind to a cancer marker on the surface of a cancer cell in the cancer. In some embodiments, the radiolabeled molecular probe includes a radiolabeled nucleic acid, which can hybridize to a targeted nucleic acid. The molecular probe can also include a radiolabel that emits the radiation particle or wave. P-32 is an exemplary radiolabel, which emits beta particles. F-18 is another exemplary radiolabel, which emits positrons (which produce gamma waves). Ultrasonic waves are transmitted from an interrogator comprising one or more ultrasonic transducers to an implantable device. The implantable device includes an ultrasonic transducer and two or more stacked arrays. Each array comprises a plurality of pixels, and each pixel comprises a radiation-sensitive diode configured to generate an electrical signal upon encountering the radiation particle or wave. In some embodiments, the ultrasonic waves power the one or more implantable devices. The method further includes receiving from the one or more implantable devices ultrasonic backscatter that encodes information related to the encountered radiation particle or wave. The ultrasonic backscatter can encode, for example, the pixel address of the one or more pixels that encountered the radiation particle or wave. In some embodiments, the integrated circuit comprises a processor configured to determine a directional vector of the radiation particle or wave based on the pixel addresses of a pair of pixels that encountered the same radiation particle or wave. In some embodiments, the ultrasonic backscatter encodes the directional vector of the radiation particle or wave. In some embodiments, the integrated circuit is configured to determine the location relative to the implantable device of the radiation source based on a plurality of directional vectors from a plurality of radiation particles or waves emitted by the radiation source. In some embodiments, the ultrasonic backscatter encodes the relative location of the radiation source.

In some embodiments, the implantable devices are used for positron emission tomography (PET). A plurality of implantable devices can be disposed on, in, or near a radiolabeled cell or cluster of cells. The implantable devices each include two or more arrays comprising a plurality of radiation-sensitive diodes configured to generate an electrical signal upon encountering radiation (e.g., gamma waves). The implantable device also includes an integrated circuit with a digital circuit, and a miniaturized ultrasonic transducer. The radiolabel emits photons or positrons (for example, an F-18 radiolabel). The positrons encounter an electron to produce two or more photons (i.e., gamma waves). In some embodiments, the radiolabel is attached to a molecular probe that can specifically bind a cell (e.g., a cancer cell). For example, the positron-emitting radiolabel can be attached to an antibody or antibody mimetic that specifically binds a tumor marker. In some embodiments, one or more of the arrays is coated with a blocking material on one side of the arrays. Exemplary blocking materials can include lead, gold, or platinum. The blocking material is a dense material that limits passage of gamma waves, thus limiting noise in other implantable devices. The gamma waves are directed in different directions, and two or more different implantable devices can encounter the gamma waves simultaneously in different locations. The information related to the encountered radiation can be encoded on ultrasonic backscatter received by an interrogator. The information can include a timestamp, which indicates the time or the relative time the implantable device encountered the radiation. Because two or more photons are emitted from the same positron (and thus, same location) at the same time, simultaneous encounter of the gamma waves by two different implantable devices verifies the signal and distinguishes it from back ground noise. The timestamp can be relative to a received ultrasonic wave that was transmitted to the two or more implantable devices. For example, the interrogator transmits ultrasonic waves to the implantable devices to sync an internal clock. The backscatter encoding information related to the encountered radiation can include a timestamp relative to the internal clock sync. This verifies the gamma waves that encountered from two or more different implantable devices originated from the same positron event, and thus originated form the same location. The location of origin of the gamma waves can be determined as previously described.

Systems

A system useful for detecting radiation includes an interrogator and one or more implantable devices, as described herein. In some embodiments, the system further comprises an additional device, which can operate or power the interrogator, for example if the interrogator is implanted within a subject. The system can also include a computer system configured to operate the interrogator or analyze ultrasonic backscatter.

In some embodiments, the system comprises one or more implantable devices as described herein; and an interrogator (which is optionally configured to be wearable by a subject) comprising one or more ultrasonic transducers configured to transmit ultrasonic waves to the one or more implantable devices or receive ultrasonic backscatter from the one or more implantable devices. The one or more ultrasonic transducers of the interrogator are optionally disposed in one or more transducer arrays. In some embodiments, the system includes a plurality of implantable devices, and the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator comprises a first ultrasonic transducer configured to transmit ultrasonic waves and a second ultrasonic transducer configured to receive ultrasonic backscatter from the one or more implantable devices. In some embodiments, at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator. In some embodiments, the interrogator comprises two or more separate interrogator devices, with a first interrogator device configured to transmit ultrasonic waves to the one or more implantable devices and a second interrogator configured to receive ultrasonic backscatter from the one or more implantable devices.

In some embodiments, the system comprises one or more implantable devices comprising a radiation-sensitive transistor (such as a MOSFET, e.g., a pMOS or an nMOS) configured to modulate a current based on exposure of the transistor to radiation, and an ultrasonic device configured to receive the modulated current and emit an ultrasonic backscatter that encodes the exposure of the transistor to radiation, the ultrasonic device comprising an ultrasonic transducer; and an interrogator (which is optionally configured to be wearable by a subject) comprising one or more ultrasonic transducers configured to transmit ultrasonic waves to the one or more implantable devices or receive ultrasonic backscatter from the one or more implantable devices. In some embodiments, the gate and the drain of the radiation-sensitive transistor are directly connected. In some embodiments, the implantable device comprises a resistor bridge comprising two or more resistors bridging the drain and the source of the transistor, and the gate is directly connected to the resistor bridge between two of the resistors. Preferably, the implantable device is miniaturized, and has a length of about 5 mm or less (such as about 4 mm or less, about 3 mm or less, about 2 mm or less, or about 1 mm or less) in the longest dimension. The one or more ultrasonic transducers of the interrogator are optionally disposed in one or more transducer arrays. In some embodiments, the system includes a plurality of implantable devices, and the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator comprises a first ultrasonic transducer configured to transmit ultrasonic waves and a second ultrasonic transducer configured to receive ultrasonic backscatter from the one or more implantable devices. In some embodiments, at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator. In some embodiments, the interrogator comprises two or more separate interrogator devices, with a first interrogator device configured to transmit ultrasonic waves to the one or more implantable devices and a second interrogator configured to receive ultrasonic backscatter from the one or more implantable devices.

In some embodiments, the system comprises one or more implantable devices comprising a radiation-sensitive transistor (such as a MOSFET, e.g., a pMOS or an nMOS) configured to modulate a current based on exposure of the transistor to radiation, an ultrasonic transducer configured to receive the modulated current and emit an ultrasonic backscatter that encodes the exposure of the transistor to radiation, and an integrated circuit configured to receive the current modulated by the radiation-sensitive transistor and transmit a signal encoding the exposure of the transistor to radiation to the ultrasonic transducer; and an interrogator (which is optionally configured to be wearable by a subject) comprising one or more ultrasonic transducers configured to transmit ultrasonic waves to the one or more implantable devices or receive ultrasonic backscatter from the one or more implantable devices. The signal encoding the exposure of the transistor to radiation transmitted to the ultrasonic transducer on the implantable device can be an analog or digitized signal, and the digital circuit can transmit the signal to the ultrasonic transducer by modulating a current to the ultrasonic transducer via a modulation circuit comprising a switch. In some embodiments, the gate and the drain of the radiation-sensitive transistor are directly connected. In some embodiments, the implantable device comprises a resistor bridge comprising two or more resistors bridging the drain and the source of the transistor, and the gate is directly connected to the resistor bridge between two of the resistors. Preferably, the implantable device is miniaturized, and has a length of about 5 mm or less (such as about 4 mm or less, about 3 mm or less, about 2 mm or less, or about 1 mm or less) in the longest dimension. The one or more ultrasonic transducers of the interrogator are optionally disposed in one or more transducer arrays. In some embodiments, the system includes a plurality of implantable devices, and the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator comprises a first ultrasonic transducer configured to transmit ultrasonic waves and a second ultrasonic transducer configured to receive ultrasonic backscatter from the one or more implantable devices. In some embodiments, at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator. In some embodiments, the interrogator comprises two or more separate interrogator devices, with a first interrogator device configured to transmit ultrasonic waves to the one or more implantable devices and a second interrogator configured to receive ultrasonic backscatter from the one or more implantable devices.

In some embodiments, the system comprises one or more implantable devices comprising one or more radiation-sensitive elements (such as a diode, a transistor, or flash memory cell) configured to generate an electrical signal upon encountering radiation, an integrated circuit configured to receive the electrical signal and modulate a current based on the received electrical signal, and an ultrasonic transducer configured to receive the modulated current and emit an ultrasonic backscatter based on the received modulated current; and an interrogator (which is optionally configured to be wearable by a subject) comprising one or more ultrasonic transducers configured to transmit ultrasonic waves to the one or more implantable devices or receive ultrasonic backscatter from the one or more implantable devices. In some embodiments, the implantable device comprises a plurality of radiation-sensitive diodes disposed in a pixel array. Preferably, the implantable device has a length of about 5 mm or less (such as about 4 mm or less, about 3 mm or less, about 2 mm or less, or about 1 mm or less) in the longest dimension. The one or more ultrasonic transducers of the interrogator are optionally disposed in one or more transducer arrays. In some embodiments, the system includes a plurality of implantable devices, and the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator comprises a first ultrasonic transducer configured to transmit ultrasonic waves and a second ultrasonic transducer configured to receive ultrasonic backscatter from the one or more implantable devices. In some embodiments, at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator. In some embodiments, the interrogator comprises two or more separate interrogator devices, with a first interrogator device configured to transmit ultrasonic waves to the one or more implantable devices and a second interrogator configured to receive ultrasonic backscatter from the one or more implantable devices.

In some embodiments, the system comprises one or more implantable devices comprising two or more stacked arrays, each array comprising a plurality of pixels (each pixel comprising a radiation-sensitive diode configured to generate an electrical signal upon encountering radiation), an integrated circuit configured to receive the electrical signal and modulate a current based on the received electrical signal, and an ultrasonic transducer configured to receive the modulated current and emit an ultrasonic backscatter based on the received modulated current; and an interrogator (which is optionally configured to be wearable by a subject) comprising one or more ultrasonic transducers configured to transmit ultrasonic waves to the one or more implantable devices or receive ultrasonic backscatter from the one or more implantable devices. The two or more arrays are preferably separated by about 1 mm or less (such as about 0.5 mm or less, or about 0.2 mm or less). Preferably, the implantable device is miniaturized, and has a length of about 5 mm or less (such as about 4 mm or less, about 3 mm or less, about 2 mm or less, or about 1 mm or less) in the longest dimension. The implantable device can be configured to emit ultrasonic backscatter that encodes the pixel address of one or more pixels that encounter a radiation particle or wave. In some embodiments, the implantable device is configured to analyze the pixel addresses of two or more pixels that encounter a radiation particle or wave to determine a directional vector for the encountered radiation. In some embodiments, the implantable device is configured to emit ultrasonic backscatter that encodes the directional vector (for example by the integrated circuit transmitting a digitized signal to the transducer encoding the directional vector). In some embodiments, the implantable device is configured to determine a location of the radiation source (relative to the implantable device) based on a hotspot of a plurality of intersecting directional vectors. In some embodiments, the location of the radiation source is encoded by ultrasonic backscatter emitted by the implantable device. The one or more ultrasonic transducers of the interrogator are optionally disposed in one or more transducer arrays. In some embodiments, the system includes a plurality of implantable devices, and the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator comprises a first ultrasonic transducer configured to transmit ultrasonic waves and a second ultrasonic transducer configured to receive ultrasonic backscatter from the one or more implantable devices. In some embodiments, at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator. In some embodiments, the interrogator comprises two or more separate interrogator devices, with a first interrogator device configured to transmit ultrasonic waves to the one or more implantable devices and a second interrogator configured to receive ultrasonic backscatter from the one or more implantable devices.

In some embodiments, the system includes an additional device configured to communicate with and/or power the interrogator. In some embodiments, the additional device communicates with or powers the interrogator wirelessly, such as through WiFi, BLUETOOTH® wireless technology radio, or other RF communication. The interrogator may receive ultrasonic backscatter from the implantable device and relay the information encoded by the backscatter to the additional device. This may be useful, for example, if the interrogator is implanted in a subject and the additional device is external to the subject.

The system can include a computer system, which may be integrated with the interrogator or may be separate from the interrogator. The computer system includes one or more processors and a non-transitory computer-readable storage medium storing one or more programs configured to be executed by the one or more processors. The computer system may also include one or more input/output devices (e.g., a monitor, keyboard, disk drive, Internet connection, USB port, etc.). At least some values based on the results of the above-described processes can be saved for subsequent use. The computer program may be written, for example, in a general-purpose programming language (e.g., Pascal, C, C++, Java, Python, JSON, etc.) or some specialized application-specific language.

In some embodiments, the computer system comprises one or more processors; and a non-transitory computer-readable storage medium storing one or more programs configured to be executed by the one or more processors, the one or more programs comprising instructions for determining an amount of radiation exposed to one or more implantable devices between a first time point and a second time point based on ultrasonic backscatter emitted by the one or more implantable devices at the first time point and the second time point. In some embodiments, the one or more programs include instructions for determining a location for the one or more implantable devices relative to the one or more ultrasonic transducers based on the ultrasonic backscatter emitted by the one or more implantable devices. In some embodiments, the one or more programs include instructions for determining movement (such as angular or lateral movement) of the one or more implantable devices relative to the one or more ultrasonic transducers based on the ultrasonic backscatter emitted by the one or more implantable devices. In some embodiments, the computer system is integrated with the interrogator, and in some embodiments the interrogator is a separate device. The one or more programs can include instructions for operating the one or more transducers, which may include instructions for alternatively transmitting ultrasonic waves or receiving ultrasonic backscatter.

In some embodiments, the computer system comprises one or more processors; and a non-transitory computer-readable storage medium storing one or more programs configured to be executed by the one or more processors, the one or more programs comprising instructions for determining a location of a radiation source (such as a radiolabeled cancer) relative to one or more implantable devices based on ultrasonic backscatter emitted by the one or more implantable devices. In some embodiments, the one or more programs includes instructions for determining a plurality of directional vectors for a plurality of radiation particles or waves based on the ultrasonic backscatter emitted by the one or more implantable devices; and determining the location of the radiation source based on the plurality of directional vectors. In some embodiments, the one or more programs include instructions for determining a location for the one or more implantable devices relative to the one or more ultrasonic transducers based on the ultrasonic backscatter emitted by the one or more implantable devices. In some embodiments, the one or more programs include instructions for determining movement (such as angular or lateral movement) of the one or more implantable devices relative to the one or more ultrasonic transducers based on the ultrasonic backscatter emitted by the one or more implantable devices. In some embodiments, the computer system is integrated with the interrogator, and in some embodiments the interrogator is a separate device. The one or more programs can include instructions for operating the one or more transducers, which may include instructions for alternatively transmitting ultrasonic waves or receiving ultrasonic backscatter.

Manufacture of an Implantable Device

The implantable devices can be manufactured by attaching a miniaturized ultrasonic transducer (e.g., a PMUT, CMUT, or bulk piezoelectric transducer) to a first electrode on a first face of the piezoelectric transducer, and a second electrode to a second face of the piezoelectric transducer, wherein the first face and the second face are on opposite sides of the piezoelectric transducer. The first electrode and the second electrode can be attached to an application-specific integrated circuit (ASIC), which may be disposed on a printed circuit board (PCB). Attachment of the components to the PCB can include wirebonding, soldering, flip-chip bonding, or gold bump bonding. The ASIC can include one or more radiation-sensitive pixels, arrays comprising a plurality of radiation-sensitive pixels, or a radiation-sensitive transistor.

Certain piezoelectric materials can be commercially obtained, such as metalized PZT sheets of varying thickness (for example, PSI-5A4E, Piezo Systems, Woburn, Mass., or PZT 841, APC Internationals, Mackeyville, Pa.). In some embodiments, a piezoelectric material sheet is diced into a desired size, and the diced piezoelectric material is attached to the electrodes. In some embodiments, the electrodes are attached to the piezoelectric material sheet, and the piezoelectric material sheet is diced to the desired size with the electrodes attached to the piezoelectric material. The piezoelectric material can be diced using a dicing saw with a ceramic blade to cut sheets of the piezoelectric material into individualized piezoelectric transducer. In some embodiments, a laser cutter is used to dice the piezoelectric material. In some embodiments, patterned etching is used to dice or singulate the piezoelectric material.

Electrodes can be attached to the top and bottom of the faces of the piezoelectric transducers, with the distance between the electrodes being defined as the height of the piezoelectric transducer. Exemplary electrodes can comprise one or more of silver, gold, platinum, platinum-black, poly (3,4-ethylenedioxythiophene (PEDOT), a conductive polymer (such as conductive PDMS or polyimide), or nickel. In some embodiments, the electrode is attached to the piezoelectric transducer by electroplating or vacuum depositing the electrode material onto the face of the piezoelectric transducer. In some embodiments, the electrodes are soldered onto the piezoelectric transducer using an appropriate solder and flux. In some embodiments, the electrodes are attached to the piezoelectric transducer using an epoxy (such as a silver epoxy) or low-temperature soldering (such as by use of a solder paste).

In an exemplary embodiment, solder paste is applied to a pad on a printed circuit board (PCB), either before or after the ASIC is attached to the PCB. The size of the pad on the circuit board can depend on the desired size of the piezoelectric transducer. Solely by way of example, if the desired size of piezoelectric transducer is about 100 μm×100 μm×100 μm, the pad can be about 100 μm×100 μm. The pad functions as the first electrode for the implantable device. A piezoelectric material (which may be larger than the pad) is placed on the pad, and is held to the pad by the applied solder paste, resulting in a piezoelectric-PCB assembly. The piezoelectric-PCB assembly is heated to cure the solder paste, thereby bonding the piezoelectric transducer to the PCB. If the piezoelectric material is larger than the pad, the piezoelectric material is cut to the desired size, for example using a wafer dicing saw or a laser cutter. Non-bonded portions of the piezoelectric material (for example, the portions of the piezoelectric material that did not overlay the pad) are removed. A second electrode is attached to the piezoelectric transducer and the PCB, for example by forming a wirebond between the top of the piezoelectric transducer and the PCB, which completes the circuit. The wirebond is made using a wire made from any conductive material, such as aluminum, copper, silver, or gold.

The integrated circuit and the miniaturized ultrasonic transducer can be attached on the same side of the PCB or on opposite sides of the PCB. In some embodiments, the PCB is a flexible PCB, the integrated circuit and the miniaturized ultrasonic transducer are attached to the same side of the PCB, and the PCB is folded, resulting in an implantable device in which the integrated circuit and the miniaturized ultrasonic transducer are on opposite sides of the PCB.

Optionally, the device or a portion of the device is encapsulated in or a portion of the device is encapsulated in a biocompatible material (such as a biocompatible polymer), for example a copolymer of N-vinyl-2-pyrrolidinone (NVP) and n-butylmethacrylate (BMass.), polydimethylsiloxane (PDMS, e.g., Sylgard 184, Dow Corning, Midland, Mich.), parylene, polyimide, silicon nitride, silicon dioxide, alumina, niobium, hydroxyapatite, or silicon carbide. The silicon carbide can be amorphous silicon carbide or crystalline silicon carbide. In some embodiments, the biocompatible material (such as amorphous silicon carbide) is applied to the device by plasma enhanced chemical vapor deposition (PECVD) or sputtering. PECVD may use precursors such as $SiH_4$ and $CH_4$ to generate the silicon carbide. In some embodiments, the implantable device or portion of the implantable device is encased in a ceramic (for example, alumina or titania) or a metal (for example, steel or titanium) suitable for medical implantation.

Figure 19:
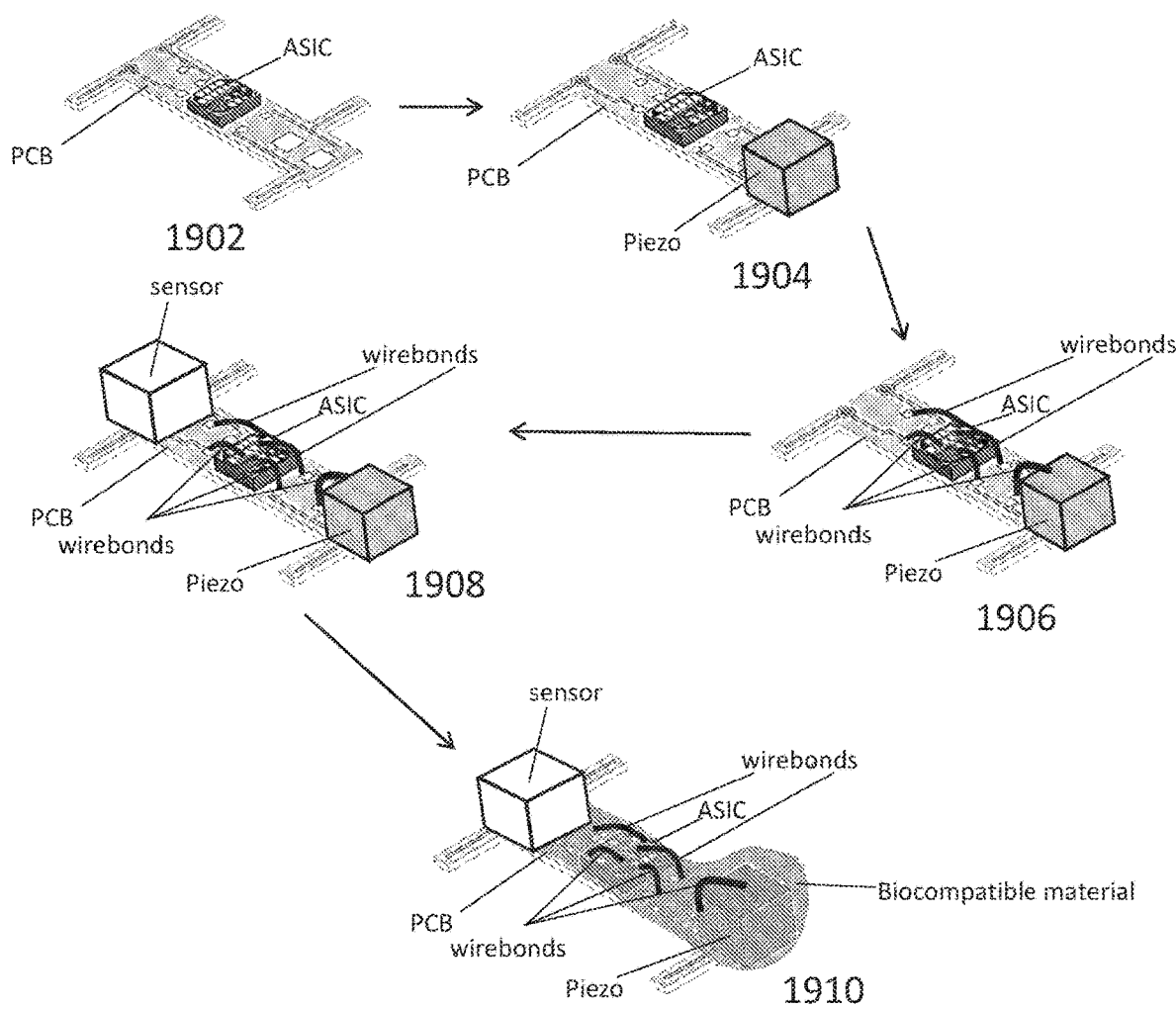
FIG. 19 illustrates a method of manufacturing an implantable device described herein.

FIG. 19 illustrates an exemplary method of producing the implantable device described herein. At step 1902, an ASIC is attached to a PCB. A solder (such as a silver epoxy) can be applied to the PCB (for example, at a first pad disposed on the PCB), and the ASIC can be placed on the solder. The solder can be cured, for example by heating the PCB with the ASIC. In some embodiments, the PCB with the ASIC is heated to about 50° C. to about 200° C., such as about 80° C. to about 170° C., or about 150° C. In some embodiments, the PCB with the ASIC is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. Optionally, the ASIC is coated with additional solder. At step 1904, a piezoelectric transducer (the "piezo" in FIG. 19) is attached to the PCB. A solder (such as a silver epoxy) can be applied to the PCB (for example, at a second pad disposed on the PCB), and a piezoelectric material can be placed on the solder. The piezoelectric material can be a fully formed (i.e., "diced") piezoelectric transducer, or can be a piezoelectric material sheet that is cut to form the piezoelectric transducer once attached to the PCB. The solder can be cured, for example by heating the PCB with the piezoelectric material. In some embodiments, the PCB with the piezoelectric material is heated to about 50° C. to about 200° C., such as about 80° C. to about 170° C., or about 150° C. In some embodiments, the PCB with the piezoelectric material is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. The piezoelectric material can be cut using a saw or laser cutter to the desired dimensions. In some embodiments, the piezoelectric material is a solgel (such as a PZT solgel) and the transducer material can be shaped with deep reactive ion etching (DRIE). Although FIG. 19 illustrates attachment of the ASIC to the PCB at step 1902 prior to attachment of the piezoelectric material to the PCB at step 1904, a person of skill in the art will appreciate that the ASIC and the piezoelectric material can be attached in any order. At step 1906, the ASIC and the piezoelectric transducer are wirebonded to the PCB. Although the method illustrated in FIG. 19 shows the ASIC and the piezoelectric transducer to the PCB after the ASIC and the piezoelectric transducer are attached to the PCB, a person of skill in the art will appreciate that the ASIC can be wirebonded to the PCB after the ASIC is attached to the PCB, and can be wirebonded either before or after attachment of the piezoelectric transducer. Similarly, the piezoelectric transducer may be wirebonded to the PCB either before or after attachment or wirebonding of the ASIC to the PCB. At step 1908, a radiation sensor (e.g., a radiation-sensitive transistor, a radiation-sensitive pixel, or an array comprising a plurality of radiation-sensitive pixels) is attached to the PCB. The sensor can be any sensor described herein. A solder (such as a silver epoxy) can be applied to the PCB (for example, at a third pad disposed on the PCB), and the sensor can be placed on the solder. The solder can be cured, for example by heating the PCB with the sensor. In some embodiments, the PCB with the sensor is heated to about 50° C. to about 200° C., such as about 80° C. to about 170° C., or about 150° C. In some embodiments, the PCB with the sensor is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. Although FIG. 19 illustrates the sensor being attached the PCB after the piezoelectric transducer and the ASIC are attached to the PCB, a person of skill in the art would understand that the sensor can be attached to the PCB either before or after the ASIC and the piezoelectric transducer are attached to the PCB. Depending on the sensor type, the sensor may be wirebonded to the PCB, which may occur after the sensor is attached to the PCB, and either before or after wirebonding of the piezoelectric transducer and/or ASIC to the PCB. At step 1910, at least a portion of the device is coated with a biocompatible material. Preferably, at least the piezoelectric transducer and the ASIC are coated with the biocompatible material. In some embodiments, the sensor is not or at least a portion of the sensor is not coated with the biocompatible material. In some embodiments, the biocompatible material is cured, for example by exposure to UV light or by heating.

Figure 20:
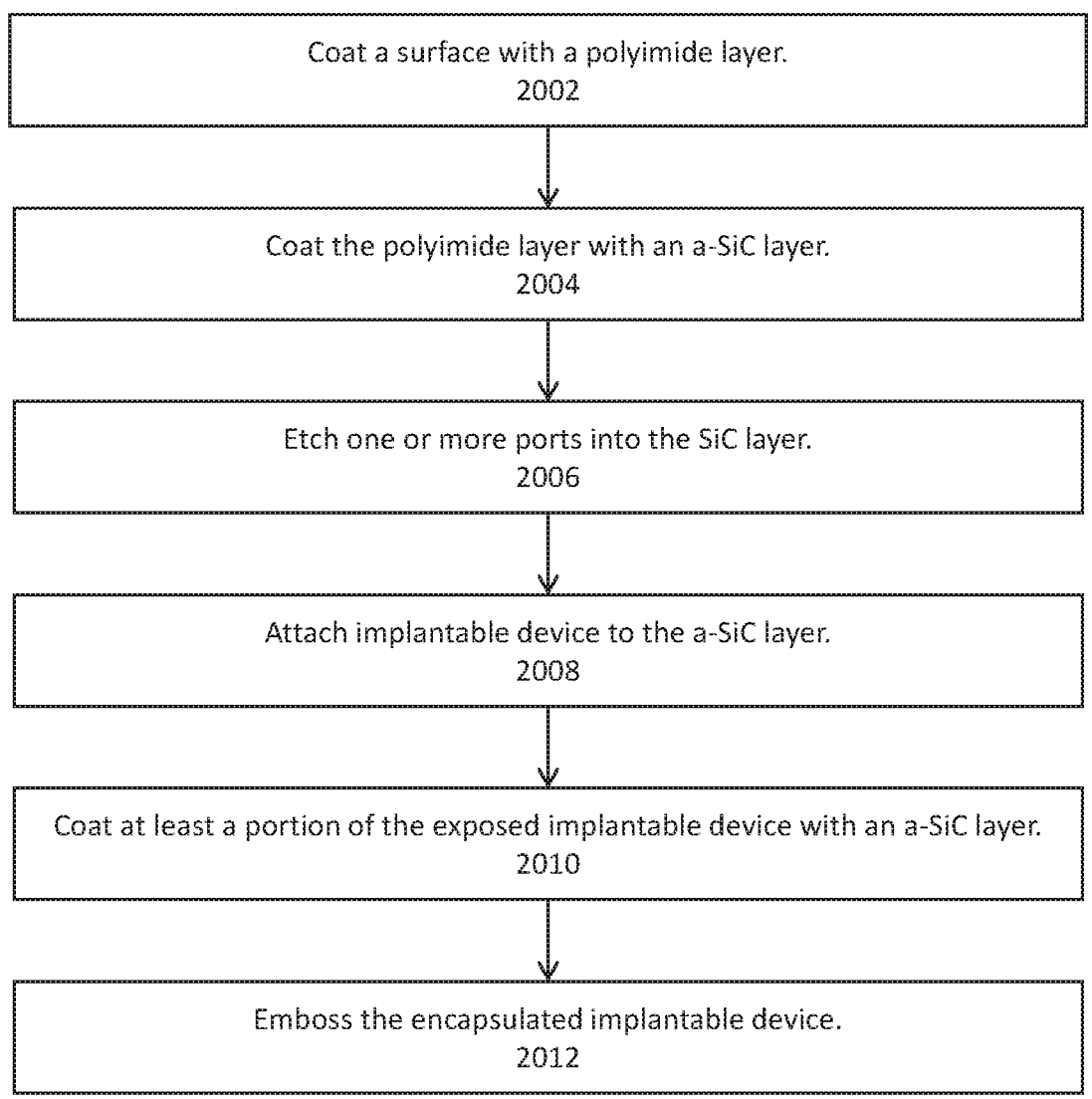
FIG. 20 is a flowchart for a method of encapsulating an implantable device with amorphous silicon carbide.

In some embodiments, the implantable device or a portion of the implantable device is encapsulated in an amorphous silicon carbide (a-SiC) film. FIG. 20 illustrates a method of manufacturing an implantable device encapsulated in an a-SiC film. At step 2002, a polyimide layer is applied to a smooth surface. At step 2004, an a-SiC layer is applied to the polyimide layer. This can be done, for example, using plasma enhanced chemical vapor deposition (PECVD), using $SiH_4$ and $CH_4$ as precursors. At step 2006, one or more ports are etched into the a-SiC layer. In some embodiments, ports are also etched into the polyimide layer. The ports provide access for portions of the implantable device that are not encapsulated by the a-SiC, such as portions of a sensor or an electrode that will contact the tissue, blood, or interstitial fluid after implant. In some embodiments, etching comprises reactive-ion etching. At step 2008, the implantable device is attached to the a-SiC layer. The implantable device may be pre-assembled before being attached to the a-SiC layer, or may be built on the a-SiC. In some embodiments, a printed circuit board (PCB), miniaturized ultrasonic transducer, and sensor are attached to the a-SiC layer. The miniaturized ultrasonic transducer and the sensor need not come in direct contact with the a-SiC layer, as they may be attached to the PCB. Attachment of miniaturized ultrasonic transducer or sensor to the PCB may occur before or after attachment of the PCB to the a-SiC layer. In some embodiments, attachment of miniaturized ultrasonic transducer or sensor to the PCB comprises wirebonding the miniaturized ultrasonic transducer or sensor to the PCB. In some embodiments, the sensor includes a portion that interfaces with the ports etched into the a-SiC layer. In some embodiments, an ASIC is attached to the PCB, which may occur before or after attachment of the PCB to the a-SiC layer. At step 2010, an exposed portion of the implantable device is coated with an a-SiC layer. In some embodiments, the exposed portion of the implantable device is coated with an a-SiC layer using PECVD. At step 2012, the encapsulated implantable device is embossed, thereby releasing the implantable device from the SiC layer.

EXEMPLARY EMBODIMENTS

Embodiment 1. An implantable device, comprising:
a radiation-sensitive transistor configured to modulate a current as a function of radiation exposure to the transistor; and
an ultrasonic device comprising an ultrasonic transducer configured to emit an ultrasonic backscatter that encodes the radiation exposure to the transistor.

Embodiment 2. The implantable device of embodiment 1, wherein the modulated current flows through the ultrasonic transducer.

Embodiment 3. The implantable device of embodiment 1, wherein the ultrasonic device comprises an integrated circuit configured to detect the current modulated by the radiation-sensitive transistor and transmit a signal encoding the exposure of the transistor to radiation to the ultrasonic transducer.

Embodiment 4. The implantable device of any one of embodiments 1-3, wherein the radiation-sensitive transistor is a metal-oxide-semiconductor field effect transistor (MOSFET).

Embodiment 5. The implantable device of any one of embodiments 1-4, wherein the radiation-sensitive transistor is an n-channel MOSFET (nMOS).

Embodiment 6. The implantable device of any one of embodiments 1-4, wherein the radiation-sensitive transistor is a p-channel MOSFET (pMOS).

Embodiment 7. The implantable device of any one of embodiments 1-6, wherein the radiation-sensitive transistor comprises silicon.

Embodiment 8. The implantable device of any one of embodiments 1-7, wherein the radiation-sensitive transistor comprises a gate and a drain, and wherein the gate and the drain are directly connected.

Embodiment 9. The implantable device of any one of embodiments 1-8, wherein the radiation-sensitive transistor comprises a gate, a drain, a source, and a body; wherein the implantable device comprises a resistor bridge comprising two or more resistors bridging the drain and the source; and wherein the gate is directly connected to the resistor bridge between two of the resistors.

Embodiment 10. The implantable device of any one of embodiments 1-9, wherein the radiation is proton radiation, alpha particles, beta particles, or gamma-rays.

Embodiment 11. An implantable device, comprising:
a radiation-sensitive diode configured to generate an electrical signal upon encountering radiation;
an integrated circuit configured to receive the electrical signal and modulate a current based on the received electrical signal; and
an ultrasonic transducer configured to emit an ultrasonic backscatter based on the modulated current encoding information relating to the encountered radiation.

Embodiment 12. The implantable device of embodiment 11, wherein the magnitude of the electrical signal is based on the energy of the encountered radiation.

Embodiment 13. The implantable device of embodiment 11 or 12, wherein the radiation-sensitive diode is part of an array comprising a plurality of pixels, each pixel comprising a radiation-sensitive diode configured to generate an electrical signal upon encountering radiation.

Embodiment 14. The implantable device of embodiment 13, wherein the implantable device comprises two or more arrays comprising a plurality of pixels, each pixel comprising a radiation-sensitive diode configured to generate an electrical signal upon encountering radiation.

Embodiment 15. The implantable device of embodiment 14, wherein the plurality of arrays consists of two arrays.

Embodiment 16. The implantable device of embodiment 14 or 15, wherein the arrays in the plurality of arrays are stacked.

Embodiment 17. The implantable device of any one of embodiments 14-16, wherein each array in the plurality of arrays comprises an equal number of pixels.

Embodiment 18. The implantable device of any one of embodiments 14-17, wherein the arrays in the plurality of arrays are separated by about 1 mm or less.

Embodiment 19. The implantable device of any one of embodiments 14-18, wherein the implantable device is configured to determine a directional vector for the encountered radiation.

Embodiment 20. The implantable device of embodiment 19, wherein the implantable device is configured to determine a location of origin of the encountered radiation.

Embodiment 21. The implantable device of embodiment 20, wherein the location of origin is a radiolabeled cell, a radiolabeled cluster of cells, or a radiolabeled molecule.

Embodiment 22. The implantable device of embodiment 21, wherein the location of origin is a radiolabeled cancer.

Embodiment 23. The implantable device of embodiment 21 or 22, wherein the cluster of cells is radiolabeled using a radiolabeled molecular probe.

Embodiment 24. The implantable device of embodiment 23, wherein the molecular probe comprises an antibody, an antibody mimetic, or a nucleic acid.

Embodiment 25. The implantable device of embodiment 23 or 24, wherein the molecular probe is radiolabeled using phosphorus-32 (P-32) or fluorine-18 (F-18).

Embodiment 26. The implantable device of embodiment 20, wherein the location of origin is a radiation beam.

Embodiment 27. The implantable device of any one of embodiments 13-26, wherein each pixel within the array is assigned a unique address.

Embodiment 28. The implantable device of any one of embodiments 11-27, wherein the implantable device is configured to filter radiation below a predetermined energy threshold.

Embodiment 29. The implantable device of embodiment 28, wherein radiation is filtered based on the magnitude of the electrical signal generated by the radiation sensitive diode upon encountering the radiation.

Embodiment 30. The implantable device of embodiment 28, wherein the implantable device comprises three or more arrays comprising a plurality of pixels comprising a radiation-sensitive diode, and wherein the radiation is filtered based on a changed directional vector between the three or more arrays.

Embodiment 31. The implantable device of any one of embodiments 11-30, wherein the radiation comprises protons, beta particles, alpha particles, or gamma waves.

Embodiment 32. The implantable device of any one of embodiments 11-31, wherein the radiation comprises beta particles.

Embodiment 33. The implantable device of any one of embodiments 11-32, wherein the implantable device comprises a memory configured to store information related to the encountered radiation.

Embodiment 34. The implantable device of any one of embodiments 11-33, wherein the implantable device comprises a clock, and wherein the information related to the encountered radiation comprises information related to the time the radiation-sensitive diode encountered the radiation.

Embodiment 35. The implantable device of any one of embodiments 11-34, wherein the diode is covered by a scintillator material.

Embodiment 36. The implantable device of any one of embodiments 1-35, wherein the ultrasonic transducer has a length of about 5 mm or less in the longest dimension.

Embodiment 37. The implantable device of any one of embodiments 1-36, wherein the ultrasonic transducer is configured to receive ultrasonic waves that power the implantable device.

Embodiment 38. The implantable device of embodiment 37, wherein the ultrasonic transducer is configured to receive ultrasonic waves from an interrogator comprising one or more ultrasonic transducers.

Embodiment 39. The implantable device of any one of embodiments 1-38, wherein the ultrasonic transducer is a bulk piezoelectric transducer.

Embodiment 40. The implantable device of embodiment 39, wherein the bulk ultrasonic transducer is approximately cubic.

Embodiment 41. The implantable device of any one of embodiments 1-40, wherein the ultrasonic transducer is a piezoelectric micro-machined ultrasonic transducer (PMUT) or a capacitive micro-machined ultrasonic transducer (CMUT).

Embodiment 42. The implantable device of any one of embodiments 1-41, wherein the implantable device is about 5 mm or less in length in the longest dimension.

Embodiment 43. The implantable device of any one of embodiments 1-42, wherein the implantable device is implanted in a subject.

Embodiment 44. The implantable device of embodiment 43, wherein the subject is a human.

Embodiment 45. The implantable device of any one of embodiments 3-44, wherein the integrated circuit comprises a power circuit.

Embodiment 46. The implantable device of any one of embodiments 3-45, wherein the integrated circuit comprises a modulation circuit comprising a switch.

Embodiment 47. The implantable device of embodiment 46, wherein the switch comprises a field effect transistor (FET).

Embodiment 48. The implantable device of any one of embodiments 3-47, wherein the integrated circuit comprises an analog-to-digital converter (ADC).

Embodiment 49. The implantable device of any one of embodiments 3-48, wherein the integrated circuit comprises a digital circuit.

Embodiment 50. The implantable device of embodiment 49, wherein the digital circuit is configured to operate the modulation circuit.

Embodiment 51. The implantable device of embodiment 49 or 50, wherein the digital circuit is configured to transmit a digitized signal to the modulation circuit, wherein the digitized signal is based on detected radiation.

Embodiment 52. The implantable device of any one of embodiments 1-52, wherein the implanted device is at least partially encapsulated by a biocompatible material.

Embodiment 53. The implanted device of embodiment 52, wherein the biocompatible material comprises a copolymer of N-vinyl-2-pyrrolidinone (NVP) and n-butylmethacrylate (BMass.), polydimethylsiloxane (PDMS), parylene, polyimide, silicon nitride, silicon dioxide, alumina, niobium, hydroxyapatite, silicon carbide, titania, steel, or titanium.

Embodiment 54. The implanted device of embodiment 52, wherein the biocompatible material is a ceramic or a metal.

Embodiment 55. The implantable device of any one of embodiments 1-54, wherein the implantable device further comprises a non-responsive reflector.

Embodiment 56. A system comprising one or more implantable devices according to any one of embodiments 1-55 and an interrogator comprising one or more ultrasonic transducers configured to transmit ultrasonic waves to the one or more implantable devices or receive ultrasonic backscatter from the one or more implantable devices.

Embodiment 57. The system of embodiment 56, wherein the interrogator comprises a first ultrasonic transducer configured to transmit ultrasonic waves and a second ultrasonic transducer configured to receive ultrasonic backscatter from the one or more implantable devices.

Embodiment 58. The system of embodiment 56 or 57, wherein the interrogator comprises two or more separate interrogator devices, wherein a first interrogator device is configured to transmit ultrasonic waves to the one or more implantable devices and a second interrogator device is configured to receive ultrasonic backscatter from the one or more implantable devices.

Embodiment 59. The system according to any one of embodiments 56-58, wherein the interrogator comprises two or more ultrasonic transducer arrays, wherein each transducer array comprises two or more ultrasonic transducers.

Embodiment 60. The system according to any one of embodiments 56-59, wherein at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator.

Embodiment 61. The system according to any one of embodiments 56-60, wherein the system comprises a plurality of implantable devices.

Embodiment 62. The system according to embodiment 61, wherein the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices.

Embodiment 63. The system according to embodiment 61, wherein the interrogator is configured to simultaneously receive ultrasonic backscatter from at least two implantable devices.

Embodiment 64. The system of embodiment 61, wherein the interrogator is configured to transit ultrasonic waves to the plurality of implantable devices or receive ultrasonic backscatter from the plurality of implantable devices using time division multiplexing.

Embodiment 65. The system of embodiment 61, wherein the interrogator is configured to transit ultrasonic waves to the plurality of implantable devices or receive ultrasonic backscatter from the plurality of implantable devices using spatial multiplexing.

Embodiment 66. The system of embodiment 61, wherein the interrogator is configured to transit ultrasonic waves to the plurality of implantable devices or receive ultrasonic backscatter from the plurality of implantable devices using frequency multiplexing.

Embodiment 67. The system according to any one of embodiments 56-67, wherein the interrogator is configured to be wearable by a subject.

Embodiment 68. A computer system, comprising:
one or more processors; and
non-transitory computer-readable storage medium storing one or more programs configured to be executed by the one or more processors, the one or more programs comprising instructions for:
  determining an amount of radiation exposed to one or more implantable devices between a first time point and a second time point based on ultrasonic backscatter emitted by the one or more implantable devices at the first time point and the second time point.

Embodiment 69. A computer system, comprising:
one or more processors; and
a non-transitory computer-readable storage medium storing one or more programs configured to be executed by the one or more processors, the one or more programs comprising instructions for:
  determining a location of a radiation source relative to one or more implantable devices based on ultrasonic backscatter emitted by the one or more implantable devices.

Embodiment 70. The computer system of embodiment 69, wherein the one or more programs comprise instructions for:
  determining a plurality of directional vectors for a plurality of radiation particles or waves based on the ultrasonic backscatter emitted by the one or more implantable devices; and
  determining the location of the radiation source based on the plurality of directional vectors.

Embodiment 71. The computer system of embodiment 69 or 70, wherein the radiation source is a radiolabeled cancer.

Embodiment 72. The computer system of any one of embodiments 68-71, comprising one or more ultrasonic transducers.

Embodiment 73. The computer system of embodiment 72, wherein the one or more programs comprises instructions for operating the one or more ultrasonic transducers.

Embodiment 74. The computer system of embodiment 73, wherein the instructions for operating the one or more ultrasonic transducers comprise instructions for alternatively transmitting ultrasonic waves or receiving the ultrasonic backscatter.

Embodiment 75. The computer system of any one of embodiments 68-74, wherein the non-transitory computer readable storage medium is on a first device, and the one or more ultrasonic transducers are on a second device.

Embodiment 76. The computer system of claim 75, wherein the first device and the second device are configured to wirelessly communicate.

Embodiment 77. The computer system of any one of embodiments 68-76, wherein the one or more programs comprise instructions for determining a location for the one or more implantable devices relative to the one or more ultrasonic transducers based on the ultrasonic backscatter emitted by the one or more implantable devices.

Embodiment 78. The computer system of any one of embodiments 68-77, wherein the one or more programs comprise instructions for determining movement of the one or more implantable devices relative to the one or more ultrasonic transducers based on the ultrasonic backscatter emitted by the one or more implantable devices.

Embodiment 79. The computer system of embodiment 78, wherein the movement is angular or lateral movement.

Embodiment 80. A method of detecting radiation, comprising:
receiving ultrasonic waves that power one or more implantable devices comprising an ultrasonic transducer and a radiation-sensitive transistor;
converting energy from the ultrasonic waves into an electrical current;
exposing the radiation-sensitive transistor to an amount of radiation;
modulating the electrical current as a function of radiation exposed to the radiation-sensitive transistor;
transducing the modulated electrical current into an ultrasonic backscatter that encodes the amount of radiation exposed to the radiation-sensitive transistor; and
emitting the ultrasonic backscatter to an interrogator comprising one or more transducers configured to receive the ultrasonic backscatter.

Embodiment 81. The method of embodiment 80, wherein the electrical current flows through an integrated circuit, the method further comprising:
flowing a second electrical current through the integrated circuit and the radiation-sensitive transistor;
modulating the second electrical current as a function of radiation exposed to the radiation-sensitive transistor;
modulating the electrical current transduced into the ultrasonic backscatter based on the modulated second electrical current.

Embodiment 82. A method of treating a solid cancer in a subject, comprising:
targeting the cancer with radiation; and
monitoring targeted radiation exposure, comprising:
transmitting ultrasonic waves from an interrogator comprising one or more ultrasonic transducers to one or more implantable devices comprising an ultrasonic transducer and a radiation-sensitive transistor implanted proximal to the cancer, and
receiving from the one or more implantable devices ultrasonic backscatter encoding an amount of radiation exposed to the one or more implantable devices.

Embodiment 83. The method of embodiment 82, comprising determining the location or direction of origin of the radiation.

Embodiment 84. The method of embodiment 82 or 83, wherein the one or more implantable devices are located adjacent to, on, or within the cancer.

Embodiment 85. The method of any one of embodiments 82-84, further comprising re-targeting the cancer with the radiation based on the amount of radiation exposed to the one or more implantable devices.

Embodiment 86. The method of any one of embodiments 82-85, wherein the subject is a human.

Embodiment 87. The method of any one of embodiments 80-86, comprising determining an amount of radiation exposed to the radiation-sensitive transistor between a first time point and a second time point.

Embodiment 88. The method of embodiment 87, further comprising determining an amount of radiation exposed to the radiation-sensitive transistor between the first time point and a third time point.

Embodiment 89. The method of embodiment 87 or 88, further comprising determining a rate of radiation exposed to the radiation-sensitive transistor.

Embodiment 90. The method of any one of embodiments 80-89, wherein the radiation comprises proton particles, beta particles, alpha particles, or gamma waves.

Embodiment 91. The method of any one of embodiments 80-90, wherein the radiation is a proton beam.

Embodiment 92. A method of detecting radiation, comprising:
receiving ultrasonic waves that power one or more implantable devices comprising an ultrasonic transducer, an integrated circuit, and a radiation-sensitive diode configured to generate a signal upon encountering radiation;
converting energy from the ultrasonic waves into an electrical current that flows through the integrated circuit;
exposing the diode to a radiation particle or wave from a radiation source;
transmitting a signal to the integrated circuit indicating exposure of the diode to the radiation particle or wave;
modulating the electrical current based the signal transmitted to the integrated circuit;
transducing the modulated electrical current into an ultrasonic backscatter that encodes the radiation exposure; and
emitting the ultrasonic backscatter to an interrogator comprising one or more transducer configured to receive the ultrasonic backscatter.

Embodiment 93. The method of embodiment 92, wherein the diode is within an array comprising a plurality of pixels, each pixel comprising a radiation-sensitive diode configured to generate a signal upon encountering radiation.

Embodiment 94. The method of embodiment 93, wherein the signal transmitted to the integrated circuit indicating exposure of the pixel to radiation comprises a pixel address.

Embodiment 95. A method of detecting radiation, comprising:
receiving ultrasonic waves that power one or more implantable devices comprising an ultrasonic transducer, an integrated circuit, and two or more arrays comprising a plurality of pixels, each pixel comprising a radiation-sensitive diode configured to generate a signal upon encountering radiation;
converting energy from the ultrasonic waves into an electrical current that flows through the integrated circuit;
exposing one or more of the pixels to a radiation particle or wave from a radiation source;
transmitting a signal to the integrated circuit indicating exposure of the one or more of the pixels to the radiation particle or wave;
modulating the electrical current based the signal transmitted to the integrated circuit;
transducing the modulated electrical current into an ultrasonic backscatter that encodes the radiation exposure; and
emitting the ultrasonic backscatter to an interrogator comprising one or more transducer configured to receive the ultrasonic backscatter.

Embodiment 96. The method of embodiment 95, wherein the signal transmitted to the integrated circuit indicating exposure of the one or more pixels to the radiation particle or wave comprises a pixel address.

Embodiment 97. The method of embodiment 95 or 96, wherein a first pixel on a first array and a second pixel on a second array are exposed to the same radiation particle or wave.

Embodiment 98. The method of embodiment 97, further comprising determining a directional vector for the radiation particle or wave.

Embodiment 99. The method of embodiment 98, wherein the ultrasonic backscatter encodes the directional vector of the radiation particle or wave.

Embodiment 100. The method of embodiment 98 or 99, comprising determining a plurality of directional vectors for a plurality of radiation particles or waves.

Embodiment 101. The method of embodiment 100, comprising determining the location of the radiation source relative to the implantable device based on the plurality of directional vectors.

Embodiment 102. The method of any one of embodiments 95-101, wherein the ultrasonic backscatter encodes the pixel address.

Embodiment 103. The method of any one of embodiments 95-102, wherein the ultrasonic backscatter encodes the location of the radiation source relative to the implantable device.

Embodiment 104. The method of any one of embodiments 95-103, wherein the ultrasonic backscatter encodes a directional vector of the radiation particle or wave.

Embodiment 105. The method of any one of embodiments 95-104, wherein the radiation source is a radiolabeled cluster of cells.

Embodiment 106. The method of embodiment 105, wherein the wherein the cluster of cells is specifically bound to a radiolabeled molecular probe.

Embodiment 107. The method of embodiment 106, wherein the radiolabeled molecular probe comprises an antibody or an antibody mimetic.

Embodiment 108. The method of any one of embodiments 105-107, wherein the cluster of cells is a solid cancer.

Embodiment 109. The method of embodiment 108, wherein the solid cancer is in a subject.

Embodiment 110. The method of embodiment 109, wherein the subject is a human.

Embodiment 111. A method of monitoring a subject for recurrence of a solid cancer, comprising:
  administering to the subject a radiolabeled molecular probe that emits a radiation particle or wave and that specifically binds to the solid cancer;
  transmitting ultrasonic waves from an interrogator comprising one or more ultrasonic transducers to one or more implantable devices comprising an ultrasonic transducer and two or more stacked arrays, each array comprising a plurality of pixels comprising a radiation-sensitive diode configured to generate an electrical signal upon encountering the radiation particle or wave; and
  receiving from the one or more implantable devices ultrasonic backscatter that encodes information related to the encountered radiation particle or wave.

Embodiment 112. The method of embodiment 111, wherein the one or more implantable devices is powered by the ultrasonic waves transmitted form the interrogator.

Embodiment 113. The method of embodiment 111 or 112, wherein the information related to the encountered radiation particle or wave comprises a location of the solid cancer relative to the one or more implantable devices.

Embodiment 114. The method of embodiment 113, wherein the information related to the encountered radiation particle or wave comprises a directional vectors of the radiation particle or wave emitted from the solid cancer.

Embodiment 115. The method of embodiment 114, wherein the radiation particle counters a first pixel on a first array and a second pixel on a second array, and wherein the information related to the encountered radiation comprises a first pixel address of a first pixel that encountered the radiation particle or wave, and a second pixel address of a second pixel that encountered the radiation particle or wave.

Embodiment 116. The method of embodiment 114 or 115, further comprising determining the location of the solid cancer.

Embodiment 117. The method of any one of embodiments 111-116, wherein the one or more implantable devices are implanted at or proximal to a location of a previously excised solid cancer.

Embodiment 118. The method of any one of embodiments 111-117, comprising monitoring the movement of the solid cancer over a period of time.

Embodiment 119. The method of any one of embodiments 111-118, wherein the subject is a human.

Embodiment 120. The method of any one of embodiments 111-119, wherein the molecular probe comprises an antibody or an antibody mimetic.

Embodiment 121. The method of any one of embodiments 111-120, wherein the information related to the encountered radiation particle or wave comprises information related to the time the radiation particle or wave encountered the diode.

Embodiment 122. The method of any one of embodiments 111-121, comprising determining a first radiation particle or wave and a second radiation particle or wave originated from the same location based on the information related to the time the first radiation particle or wave encountered a first diode on a first implantable device and information related to the time the second radiation particle or wave encountered a second diode on a second implantable device.

Embodiment 123. The method of embodiment 122, wherein the first radiation particle or wave is a first photon, and the second radiation particle or wave is a second photon, wherein the first photon and the second photon originated from a positron.

Embodiment 124. The method of any one of embodiments 108-123, wherein the solid cancer has a radius of about 500 µm or less.

Embodiment 125. The method of any one of embodiments 80-124, comprising filtering background radiation particles or waves with an energy below a predetermined threshold.

Embodiment 126. The method of any one of embodiments 92-125, wherein the radiation particles or waves comprise protons, alpha particles, beta particles, or gamma waves.

Embodiment 127. The method of any one of embodiments 92-126, wherein the radiation particles or waves comprise beta particles.

Embodiment 128. The method of any one of embodiments 92-127, wherein the radiation source comprises phosphorus-32 (P-32) or fluorine-18 (F-18).

Embodiment 129. The method of any one of embodiments 80-128, further comprising receiving the ultrasonic backscatter using the interrogator.

Embodiment 130. The method of any one of embodiments 80-110 and 124-129, comprising transmitting the ultrasonic waves using the interrogator configured to transmit the ultrasonic waves.

Embodiment 131. The method of any one of embodiments 80-130, comprising implanting the one or more implantable devices.

Embodiment 132. The method of any one of embodiments 80-131, comprising determining a location of the one or more implantable devices.

Embodiment 133. The method of any one of embodiments 80-132, comprising detecting angular or lateral movement of the one or more implantable devices.

Embodiment 134. A radiation dose sensing system, comprising: an ultrasound transceiver configured to generate ultrasound transmissions and receive ultrasound backscatter produced by generated ultrasound transmissions; and a body implantable device configured to sense a radiation dose received at a location where the body implantable device is located, and comprising an ultrasound backscatter communication system to modulate in reflected ultrasound backscatter communications information indicative of the sensed radiation dose received.

Embodiment 135. A radiation sensing system, comprising:

an ultrasound transceiver configured to generate ultrasound transmissions and receive ultrasound backscatter produced by generated ultrasound transmissions; and and an array of radiation sensing elements capable of detecting radiation at fluxes ranging from 1 particles/cm$^2$/sec to 1 particle/$\mu$m$^2$/sec, but also include higher rates of flux.

Embodiment 136. The system of embodiment 135 further comprising radiation detector arrays capable of identifying the angle of origin of the emitted particle.

Embodiment 137. The system of embodiment 136, wherein two radiation detector arrays are arranged "back-to-back" such that the incident angle can be calculated by identifying the position of intersection from the same particle on both arrays.

Embodiment 138. The system of embodiment 135 wherein each radiation detection element is a diode.

Embodiment 139. The system of embodiment 135, wherein another radiation detector is compatible with silicon and/or microfabrication.

Embodiment 140. The system of embodiment 135, wherein the radiation detector array is coated with a scintillating material.

Embodiment 141. The system of embodiment 135, wherein the radiation detector array whereby each element digitizes the pixel-level signal.

Embodiment 142. The system of embodiment 135, wherein the radiation detector array whereby the angle of the incident particle is determined on-chip.

Embodiment 143. The system of embodiment 135, wherein all pixel values are transmitted off-chip.

Embodiment 144. The system of embodiment 135, wherein on-chip computation is performed to identify the origin of the radiation signal. In one instantiation, this is a focus of tumor cells in the body.

Embodiment 145. The system of embodiment 135, wherein emitted radiation consists of beta, gamma, alpha or proton particles.

Embodiment 146. The system of embodiment 135, wherein a network of radiation detector arrays is within the body, wherein each sensor has a unique identifier or operation frequency, and wherein each sensor is interrogated uniquely using a beam-steered ultrasound.

Embodiment 147. The system of embodiment 135, wherein the radiation sensor array or single element capable of detection radiation is emitted from a targeted cell or ligand identifying a disease process.

Embodiment 148. The system of embodiment 147, wherein the cell is a cancer cell.

Embodiment 149. The system of embodiment 147, wherein the ligand is one or more of a radiolabeled peptide, antibody, or small molecule binding to the tumor cells.

Embodiment 150. The system of embodiment 147, wherein the ligand is a radiolabeled peptide, antibody, or small molecule binding to the neighboring tumor stroma or microenvironment.

Embodiment 151. The system of embodiment 147, wherein the ligand is a radiolabeled peptide, antibody, or small molecule binding to a secreted.

Embodiment 152. The system of embodiment 147, wherein the ligand is injected systemically and binds to the diseased cells (such as a cancer cell) in vivo.

Embodiment 153. The system of embodiment 135, wherein the system is used to monitor treatment response.

Embodiment 154. The system of embodiment 135, wherein the system is used to monitor cancer surveillance and recurrence.

Embodiment 155. A radiation therapy system, comprising:

radiation therapy session equipment configured to perform a radiation therapy session on a patient; and the radiation dose sensing system of claim 1, wherein the radiation therapy session equipment is configured to receive information indicative of the sensed radiation dose received.

Embodiment 156. The radiation therapy system of embodiment 155, wherein the radiation therapy session equipment determines a dosage level for radiation energy directed at the patient based on the information of the sensed radiation dose received.

EXAMPLES

Example 1—Manufacture of an Implantable Device

In short form, the assembly steps of the implantable device are as follows:
1. Attach ASIC to PCB.
2. Wirebond ASIC ports to PCB
3. Attach piezoelectric element to PCB.
4. Wirebond piezoelectric element ports to PCB.
5. Encapsulate full device except for recording electrodes.

The ASIC measures 450 µm by 500 µm by 500 pm and is fabricated by Taiwan Semiconductor Manufacturing Company's 65 nm process. Each chip contains two transistors with 5 ports each: source, drain, gate, center, and bulk. Each FET uses the same bulk, so either bulk pad can be bonded to, but the transistors differ in that the transistor padded out to the top row does not contain a resistor bias network whereas the transistor padded out in the bottom row does. The chip additionally contains smaller pads for electroplating. The same process can be applied to ASIC's with more complex circuitry and thus more pads. These pads were not used in this example. Three versions of the FET were taped out:

Die 1: Long channel FET with threshold voltage: 500 mV
Die 2: Short channel FET with threshold voltage at 500 mV
Die 3: Native FET with threshold voltage at 0 mV Confirmation of electrical characteristics of these FETs were measured using a specially designed CMOS characterization board which contained of a set of pads as wirebonding targets and a second set of pads in which wires were soldered to. A sourcemeter (2400 Sourcemeter, Keithley Instruments, Cleveland, Ohio) was used to supply $V_{DS}$ to the FET and measure $I_{DS}$. An adjustable power supply (E3631A, Agilent, Santa Clara, Calif.) was used to modulate $V_{GS}$ and the I-V characteristics of the FETs were obtained. Uncharacteristic IV curves for type 2 dies were consistently measured, and upon impedance measurement, found that the short channel of the die 2s would short out the FET.

The piezoelectric element is lead-zirconium titanate (PZT). It is purchased as a disc from APC International and diced into .750 μm×750 μm×750 μm cubes using a wafer saw (DAD3240, Disco, Santa Clara, Calif.) with a ceramic blade (PN CX-010-'270-080-H). This mote size was chosen as it maximized power transfer efficiency. For more details, see Seo et al., *Neural dust: an ultrasonic, low power solution for chronic brain-machine interfaces*, arXiv: 1307.2196v1 (Jul. 8, 2013).

The implantable device substrate integrates the ASIC with the piezoelectric element and recording electrodes. The first version of the implantable device used custom-designed PCBs purchased from The Boardworks (Oakland, Calif.) as a substrate. The PCBs were made of FR-4 and were 30 mil (approximately 0.762 mm) in thickness. The dimensions of the board were 3 mm×1 mm. This design was the first attempt an integrated communication and sense platform, so pad size and spacing was chosen to facilitate assembly at the cost of larger size. To conserve PCB real-estate, each face of the PCB included pads for either the piezoelectric element or the ASIC and its respective connections to the PCB. Additionally, two recording pads were placed on the ASIC-face of the board. All exposed electrodes were plated with ENIG by The Boardworks. The pad for the ASIC to sit on was 500 μm by 500 μm, chosen to fit the size of the die. The wirebond target pad size was chosen to be 200 μm by 200 μm and spaced roughly 200 μm away from the edge of the die in order to give enough clearance for wirebonding (discussed below). Electrode size and spacing varied and were empirically optimized.

In the second iteration of implantable device, three concerns primary concerns were addressed: 1) size, 2) ease of wirebonding, 3) implantation/communication. First, to decrease board thickness the FR-4 substrate was replaced with a 2 mil (about 50.8 μm) thick polyimide flexible PCB (AltaFlex, Santa Clara, Calif.), as well as thinning the ASIC (Grinding and Dicing Services Inc., San Jose, Calif.) to 100 μm. To facilitate bonding, the ASIC and PZT coupon were moved to the same side, with only the recording electrodes on the backside of the substrate. While putting the ASIC and PZT coupon on the same side of the board does impose a limit on how much the substrate size can be reduced, spacing between the electrodes restricted the board length of at least 2 mm. To push minimization efforts ASIC bonding pads were reduced to 100 μm by 100 μm, but the 200 μm spacing between bonding pads and the ASIC itself had to be maintained to provide space for wirebonding. The attachment pads for the PZT coupon was also shrunk and placed closer to the edge of the board, with the rationale that the PZT coupon did not have to wholly sit on the board, but could hang off it. Additionally, the location of the pads relative to the ASIC was also modified to facilitate bonding. In the original design, the bond pad layout surrounding the ASIC required two wirebonds to cross. This is not impossible, but very difficult to avoid shorting the pads. Thus, the pad layout was shifted so that the bonds are relatively straight paths. Finally, during animal experiments, it was found that alignment of the implantable device was quite difficult. To combat this, four 1 inch test leads that extended off the board were added, two of which connected directly to the source and drain of the device to harvest power could be measured and to use that as an alignment metric. The other two leads connect to the gate and center ports in order to obtain a ground truth signal. In order to prevent confusion over which lead belonged to which port, the vias were given unique geometries. See FIG. 21A.

There was some fear that the test leads may be easily broken or would easily displace the mote if force was applied on them. Thus, a version with serpentine traces was designed. Serpentine traces (FIG. 21B) have often been used to enable deformable interconnects, as their structure allows them to "accordion" out. Conceptually, the serpentine trace design can be through of a series of cantilevers in series via connector beams.

Along with the presented designs, a miniaturized version of the implantable device using both sides of the substrate was also designed and assembled. In this design, the board measures roughly 1.5 mm by 0.6 mm by 1 mm Due to the miniaturization of the board, a 5 mil silver wire "tail" was attached to the device for recording. This version was not tested in vivo.

The ASIC and PZT coupon were attached to the PCB substrate using adhesives. There are three majors concerns to choosing an adhesive: 1) the adhesive needs to fix the ASIC and PZT tightly enough that the ultrasonic power from wirebonding does not shake the components, 2) due to the sub-millimeter scales and pitches of the components/substrate pads, application of the adhesive was done in a relatively precise way, and 3) the adhesive must be electrically conductive.

The ASIC and diced PZT were originally attached to the PCB substrate using a low temperature-curing solder paste. Solder paste consists of powder metal solder suspended as spheres in flux. When heat is applied, the solder balls begin to melt and fuse together. However, it was found that the curing of the solder paste would often result in translating or rotating the PZT coupon or mote during reflow. This presented problems for PZT alignment and power harvesting, as well as problems for wirebonding due to the bondpads no longer being appropriately positioned from the chip. However, it was found that a two-part silver epoxy, which simply consists of silver particles suspended in epoxy was capable of curing without repositioning the chip or PZT coupon. Thus, the ASIC and diced PZT were pasted onto the PCB using a two-part conductive silver epoxy (H20E, Epotek, Billerica, Mass.). The PCBs were then affixed to a glass slide using Kapton tape (Polyimide Film Tape 5413, 3M, St. Paul, Minn.) and put into a convection oven at 150° C. for 15 minutes to cure the epoxy. While higher temperatures could yield faster curing (FIG. 22), care was taken to avoid heating the PZT beyond 160° C., half the Curie temperature of the PZT. Heating the PZT any higher runs the risk of depolarizing the PZT. It was found that the 150° C. cure had no effect on the CMOS performance The connections between the top of the PZT and the PCB as well as the ASIC and the PCB were made by wirebonding 1 mil Al wire using an ultrasonic wedge bonder (740DB, West Bond, Scotts Valley, Calif.); in this method of bonding, the Al wire is threaded through the wedge of the bondhead and ultrasonic energy "scrubs" the Al wire against the substrate, generating heat through friction. This heat results in welding the two materials together.

Wirebonding to the ASIC was challenging to avoid shorts due to the size of the CMOS pads and the size of the foot of the wirebond. This problem was accentuated due to the positioning of the wirebonding targets in the first version of the implantable device board, which forced the feet of two bonds to be placed across the smaller width of the ASIC pad rather than the length. While thinner gold wire was available to use for bonding, the difficulty of bonding gold thermosonically with a wedge bonder made it impractical to use gold wires for bonding with this equipment. Furthermore, in order to effectively wirebond, it is important to have a flat and fixed substrate; hence, our original design of having the ASIC and PZT on different sides of the board often caused trouble during the wirebonding process in our first version of implantable boards. Thus, the substrate design choices made in the second iteration of the implantable device (moving ASIC and PZT to the same side, repositioning the pads to provide straight paths to wirebond targets) greatly improved wirebonding yield.

Finally, because an ultrasonic bonder was used, it was found that bonding to the PZT resulted in a charge build up would damage the chip once the PZT was fully bonded to the substrate. To avoid this, the source and drain test leads of the device were discharged to Earth ground directly prior to wirebonding the PZT.

The final step of the implantable device assembly is encapsulation. This step achieves two goals: 1) insulation of the PZT, bondpads, and ASIC from aqueous environments and 2) protection of the wirebonds between the ASIC/PZT coupon and the PCB. At the same time, there must be some method to either remove or prevent the encapsulant from covering the recording electrodes. Additionally, the encapsulant must not impede device implantation. Finally, while it is not crucial, it is of interest to choose an encapsulant that is optically transparent so that the device can be inspected for physical defects if some damage occurred during the encapsulation.

The first encapsulant used was Crystalbond (509', SPI Supplies, West Chester, Pa.). Crystalbond is an adhesive that is solid at room temperature but begins to soften' at 71° C. and melts into a viscous liquid at 121° C. Upon removing heat from the Crystalbond, it re-solidifies within minutes, allowing for good control. To encapsulate the implantable device, a small flake of Crystalbond was shaved off with a razor and placed directly over the device. The board was then heated using a hotplate, first bringing the temperature to around 70° C. when the flake would begin to deform and then slowly increasing the temperature until the Crystalbond became fully liquid. Once the edge of the liquid Crystalbond drop expanded past the furthest wirebond but not the recording pad, the hotplate was turned off and the board was quickly moved off the plate onto a cooling chuck where the Crystalbond would re-solidify.

While Crystal bond was effective, it was found that UV curable epoxide could give us better selectivity and biocompatibility, as well as rapid curing. First, a light-curable acrylic (3526, Loctite, Dusseldorf; Germany) was tested, which cures with exposure to ultraviolet light. A sewing needle was used as an applicator to obtain high precision and the epoxy was cured with a 405 nm laser point for 2 minutes. This epoxy worked well, but was not medical-grade and thus not appropriate for a biological implant. Thus, a medical-grade UV curable epoxy (OG116-31, EPO-TEK, Billercia, Mass.) was tried. The epoxy was cured in a UV chamber (Flash, Asiga, Anaheim Hills, Calif.) with 92 mW/cm$^2$ at 365 nm for 5 minutes. While this epoxy was slightly less viscous than the Loctite epoxy, using a sewing needle again as an applicator allowed for selective encapsulation. As an insulator and protection mechanism for the wirebonds; the epoxy was very effective, but was found to leak during prolonged submersion in water (~1 hour). A second medical grade epoxy which touted stability for up to a year, was considered (301-2, EPO-TEK, Billerica, Mass.), but was found to be not viscous enough and required oven-baking for curing. Despite the instability of the UV epoxy, the duration of use was suitable for acute in vivo experiments.

To improve encapsulant stability, parylene-C was also considered as an encapsulation material. Parylene-C is an FDA approved biocompatible polymer which is chemically and biologically inert, a good barrier and electrical insulator, and extremely conformal when vapor deposited). Vapor deposition of Parylene-C is achieved by vaporizing powder Parylene-C dimer at temperatures above 150° C. The vapor Parylene-C dimer is then heated at 690° C. in order for pyrolysis to occur, cleaving the Parylene-C dimer into monomers. The monomer then fills the chamber, which is kept at room temperature. The monomer almost instantaneously polymerizes once it comes into contact with any surfaces. For all devices, Paraylene-C was deposited using a parylene deposition system (SCS Labcoter 2 Parylene Deposition System, Specialty Coating Systems, Indianapolis, Ind.) with the parameters shown in Table 1. Note that the table indicates the chamber gauge temperature as 135° C. This is distinct from the actual chamber temperature; rather the chamber gauge is simply the vacuum gauge of the process chamber. It is important to keep the temperature to at least 135° C. to prevent parylene from depositing onto the gauge. For the first batch of FR-4 boards, parylene was addressed by selectivity by using Kapton tape to mask off the electrodes. However, it was found that due to the small pitch between the recording electrodes and the ASIC wirebonding targets, there was not enough surface area for the tape to affix well to the board and it often slipped off, resulting in coated electrode pads. In the second iteration of implantable device, a parylene coat was attempted using a strategy in which the entire board was coated, then remove the parylene off the electrodes with a probe tip. In order to assure that parylene was coated onto the entire device, the implantable devices were suspended in air by damping them between two stacks of glass slides.

TABLE 1

| Parylene-C Deposition Parameters | |
|---|---|
| Furnace Temperature | 690 deg. C. |
| Chamber Gauge Temperature | 135 deg. C. |
| Vaporizer Temperature | 175 deg. C. |
| Base Pressure | 14 mTorr |
| Operating Pressure | 35 mTorr |
| Paralyene-C Mass | 5 g |

The following provides additional details for manufacturing the implantable device.

Before beginning to work with the PCBs, ASICs, or PZT coupons, prepare two sample holders for the dust boards. To do so, simply take two glass slides (3 mm×1 mm×1 mm slides work well) and put a strip of double-sided tape on the slide lengthwise. The tape will be used to fix the dust motes in place so that the rest of the steps can be performed. On one of the slides, also add a piece of Kapton tape (3M) sticky-side up on top of the double-sided tape. This slide will be the slide used for curing as the high temperature of the cure can cause problems with the adhesive on the double-sided tape.

Next, mix a small amount of silver paste by weighing out a 1:1 ratio of part A and part B in a weigh boat. A large amount of silver-epoxy is not needed for the assembly process. Shown below is roughly 10 g of epoxy (5 g of each part) which is more than enough for three boards, Note that the mixed-silver epoxy has a shelf life of two weeks if placed at 4° C. So leftover epoxy can and should be refrigerated when not in use. Additionally, older epoxies (several days to a week) tend to be slightly more viscous than fresh epoxy which can make application easier, The substrates come panelized and will need to be removed. Each board is connected to the panel at several attachment points on the test leads and vias—these attachment points can be cut using a micro-scalpel (Feather Safety Razor Co., Osaka, Japan). Once the PCB has been singulated, using carbon-fiber tipped tweezers or ESD plastic tweezers, place the singulated PCB onto the high-temperature sample holder.

The diced/thinned dies are shipped on dicing tape, which can make it tricky to remove the die. In order to reduce the adhesion between the die and tape, it can be helpful to deform the tape. Using carbon-tipped or ESD plastic tweezers, gently press the tape and work the tweezers in a circular motion around the die. To check if the die has been freed, gently nudge the chip with the tip of the tweezers. If the die does not come off easily, continue to press into tape surrounding the chip. Once the chip has come off, carefully place the chip onto the high-temperature sample holder next to its board. It is advisable to bring the sample holder to the chip rather than the other way around so that the chip is not in transit, Care must be taken in this step to avoid losing or damaging the die. Never force a die off the tape, as excessive force can cause a chip to fly off the tape.

Next, attach the die using silver epoxy. Under a microscope, use a pin or something equally fine to apply a small amount silver epoxy to the CMOS pad on the PCB. In this step, it is better to en on the side of too little epoxy than too much epoxy since more silver paste can always be applied, but removing silver paste is non-trivial. Small amounts of uncured epoxy can be scraped away with the same tool used for application, just ensure the epoxy has been wiped off the tool.

Once the epoxy has been placed on the pad, the ASIC can be placed onto the epoxy. Due to a CAD error, some of the chips have been reflected. It is important to take care that chips which are reflected have been oriented the correct way on the board to ensure no wires need to cross during wirebonding.

Once the ASICs have been situated on the boards correctly, the silver epoxy can be cured by placing it into an oven at 150° C. for 15 minutes. Note that different temperatures can be used if needed—see FIG. 17 for details. After the silver epoxy has been cured, double-check adhesion by gently pushing on each die, If the die moves; a second coat of silver epoxy will be needed.

To prepare for wirebonding, move the devices from the high-temperature sample holder to the regular sample holder. This change is necessary because the adhesion of double-sided tape is stronger than that of the Kapton tape so wirebonding will be made easier. A piece of double-sided tape should be good enough to affix the sample holder to the wirebonder's workholder. It is best to ensure that the workholder has not been previously covered with double-sided tape so that the test leads do not get accidentally stuck to anything. If necessary, clean-room tape can be used to provide additional clamping of the sample holder.

Ensure the wirebonder is in good condition by making bonds on the provided test-substrate using default settings. Ensuring that the wirebonder is in condition is important, as a damaged wedge will not bond well and effectively just damage the ASIC pads. Forward bonds (first bond on the die, second bond on the substrate) should be made in the following order: 1. Gate. 2. Bulk. 3. Center. 4. Drain. 5. Source. While it is not critical that the bonds be made in this order, this order minimizes the number of substrate reorientations and prevents accidental damage to the bonds due to the bondhead. Small angle adjustments of the workholder can be made to facilitate bonding; it is imperative that this bond be as straight as possible. In the case that the foot of the second bond lifts from the substrate, changing the number of bonds to one and bonding the foot again may help. If proper adhesion cannot be made, a potential solution is to connect the foot of the bond and the substrate using silver epoxy. Additionally, shorts caused by two bond-feet touching can be resolved by very carefully cutting away the bridging metal using a microscalpel.

Known working bonding parameters can be found in Table 2, below. These parameters are simply guidelines and should be modified as necessary. Needing excess power (greater than 490) is typically indicative of a problem: substrate fixing (both PCB to glass slide and CMOS to PCB), wedge condition, and pad condition should all be checked. In the case of pad condition, damaged pads due to previous wirebonding attempts will usually require higher power—in some cases, the devices are salvageable, but failed attempts to bond with power higher than 600 usually results in too much damage to the pads for good bonding.

TABLE 2

Westbond 7400B A1 Parameters for ASIC

| Bond # | Power | Time |
| --- | --- | --- |
| 1 (ASIC) | 420 | 40 ms |
| 2 (Substrate) | 420 | 40 ms |

Post-wire bonding, the device should undergo electrical testing to ensure proper bonding. If using a type 1 die, the I-V characteristics should be roughly as shown in Table 3.

TABLE 3

Typical I-V characteristics for Type 1 Die under $V_{ds} = 0.1$ V

| $V_{gs}$ | $I_{ds}$ |
| --- | --- |
| 0 V | 0.5 µA |
| 0.1 V | 0.74 µA |
| 0.2 V | 10.6 µA |
| 0.3 V | 51.4 µA |
| 0.4 V | 0.192 mA |
| 0.5 V | 0.39 mA |
| 0.6 V | 1.14 mA |
| 0.7 V | 1.55 mA |
| 0.8 V | 1.85 mA |

If the I-V characteristics do not seem correct, a valuable troubleshooting method is checking the resistances between the drain and center, source and center, and drain and source. If the die is working properly, one should expect roughly 90 kΩ resistance between the drain and center and source and center, and roughly 180 k Ω between the drain and source.

After confirmation that the FET is connected properly, the PZT coupon should be attached. This is done in a similar fashion to attaching the ASIC: place a dab of silver epoxy using a sewing needle on the appropriate pad. It is best to put the epoxy dab on the back edge of the pad (towards the end of the board) since the PZT coupon will not be centered on the pad, but pushed back so that the coupon hangs off the board. Keep in mind that the polarity of the PZT coupon has a small effect on its efficiency. To determine whether or not the coupon is in the correct position, check if the bottom face is larger than the top face. Due to the path of the dicing saw, the bottom of the coupon, is slightly larger than the top of the coupon. Thus, the edges of the bottom face can be seen from a top down view, then the coupon has been placed in the same orientation as it was when the disk was diced.

Wirebonding the PZT is done in a similar manner to the ASIC (forward bonding, the PZT to the PCB). However, one crucial change is that the drain and source vias should be grounded. There is an earth ground port next to Westbond which can be accessed via a banana connector. As a guideline, the parameters shown in Table 4 have been known to work.

TABLE 4

| Westbond 7400B A1 Parameters for PZT | | |
| --- | --- | --- |
| Bond # | Power | Time |
| 1 (PZT) | 390 | 40 ms |
| 2 (Substrate) | 490 | 40 ms |

A successful bond may require several attempts depending on how well the PZT coupon is attached to the substrate. The more attempts that are made, the worse the mechanical structure of the PZT becomes (the silver coating will become damaged) so it is best to try to very quickly optimize the process. Bonds that fail due to foot detachment generally imply not enough power. Bonds that fail due to the wire breaking at the foot generally imply too much power.

After a successful bond is made, it is always good to do another electrical test to ensure that bonding the PZT has not damaged the ASIC.

As a final step, test wires were soldered to the vias and encapsulate the device, The test wires are 3 mil silver wires. Nate that these wires are insulated: the insulation can be removed by putting the wire close to a flame (not in the flame) and watching the plastic melt and recede.

After soldering wires, the device can now be encapsulated. The encapsulant is OG116-31 medical-grade UV curable epoxy and should be dispensed using a sewing needle. An effective method is to put a large drop of epoxy over the PZT coupon and a large drop over the ASIC. Using a clean needle, push the droplet over the board so that the entire topside of the board is coated. The epoxy should wet the board, but not spill over due to its surface tension. Once the main body of the board is coated, the vias should also be coated, as well as the side faces of the piezo. The board can then be cured in a UV chamber for roughly 5 minutes. It has been found that the test wires can occasionally contact something in the UV chamber and short the ASIC. Thus, prior to putting the board in the chamber, it is good to wrap the wires down or place it on some tape in order to isolate them from any chamber surfaces.

Following curing, the backside should be coated. In particular the exposed PZT coupon which hangs over the board as well as the backside of the test vias and the two vias on the backside of the board which connect the electrodes to the topside of the board. This part can be a little tricky due to the small space between the backside vias and the electrodes, so it is best to start with a very small amount of epoxy and place it near the edge of the board, then drag the epoxy up towards the vias. The backside of the board should be cured in the same manner as the topside. Once the board is fully encapsulated, a final electrical test should be done, and upon passing, the implantable device is now complete.

Example 2—Set-Up for Testing Implantable Devices

Testing of implantable has always been tricky due to the thinness of the test leads that extend out from the board. Clipping onto and off of these vias for I-V measurements has often resulted in pulling the leads off the body of the device. Furthermore, due to the test leads, it is difficult to perform watet-t11 nk test measurements; as exposed electronics in water would result in shorts. In order to circumvent this issue, a PCB was designed to serve as a testbed for implantable device measurements. The PCB (Bay Area Circuits, Fremont, Calif.) was made of FR-4 and 60 mil thick; it includes four vias, distributed on the board to match the layout of the version two implantable device boards.

Gold header pins (Pin Strip Header, 3M, Austin, Tex.) were soldered into the vias so that they extended from the board on both sides of the board. This enabled us to place our devices onto the test bed, and tap into the implantable by accessing the header pins. Next, to insulate the vias, plastic caps made out of polyethylene terephthalate (PETG) were 3D printed (Flashforge Creator X, FlashForge, Jinhua, China). These caps were printed with a groove so that an O-ring could be placed inside the groove and create a waterproof seal around the header pins. The caps were connected to the board and compression was created by drilling 2 mm holes through the PCB and cap using a micro-mill (47158, Harbor Freight, Camarillo, Calif.) and screwing the cap and board together. Wires extending from the testbed were soldered to the header pins and the pins were then encapsulated. To measure the effectiveness of the seal, the boards were submerged in an aqueous 6 M NaCl solution and the resistance between the pins was measured using a Keithley 2400. A MATLAB script was written to automatically record and plot the resistance over time. A drop in the resistance would indicate that the seal was broken. As an additional test, a piece of litmus paper was also put under the plastic cap with the intention that if the cap leaked, the litmus paper would change color. The pins were encapsulated using the same medical grade epoxy used to encapsulate the implantable device boards, and parylene was deposited over the epoxy on the back side of the testboards for a completely waterproof barrier. The resistance between the two neighboring pins of the testbed submerged in salt water solution as a function of time for only epoxy insulation and epoxy plus parylene insulation was measured. Without a parylene barrier, the epoxy began to leak, allowing salt water to short out the pins of the testbed.

Example 3—Implantable Devices Encapsulated in Silicon Carbide

Rather than an epoxy encapsulant, silicon carbide (SiC) may be a more effective material for insulating and protecting the implantable device. SiC is formed by the covalent bonding of Si and C, forming tetrahedrally oriented molecules with short bond length and thus, high bond strength, imparting high chemical and mechanical stability. Amorphous SiC (a-SiC) has been welcomed by the biomedical community as a coating material as it can be deposited at much lower temperatures than ordinarily required by crystalline SiC and is an electrical insulator. Deposition of a-SiC is generally performed via plasma enhanced chemical vapor deposition (PECVD) or sputtering. Ongoing research using sputtered a-SiC has shown that it is difficult to achieve a pinhole free layer of SiC. Rather, PECVD using $SiH_4$ and $CH_4$ as precursors is capable of yielding impressive, pinhole free SiC films.

Furthermore, implanted a-SiC has shown impressive biocompatibility. Previous studies have shown that a 50 μm iridium shaft coated with a-SiC implanted in the rabbit cortex for ~20 days did not show the usual chronic inflammatory response of macrophage, lymphocyte, monocyte recruited to the insertion site. See Hess et al., *PECVD silicon carbide as a thin film packaging material for microfabricated neural electrodes*, Materials Research Society Symposium Proceedings, vol. 1009, doi: 10.1557/PROC-1009-U04-03 (2007).

Figure 23:
FIG. 23 illustrates a schematic for encapsulating an implantable device in silicon carbide.
Figure 23:
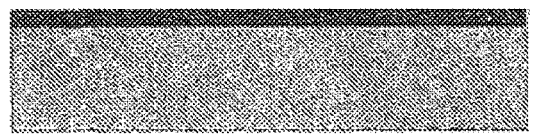
Figure 23:
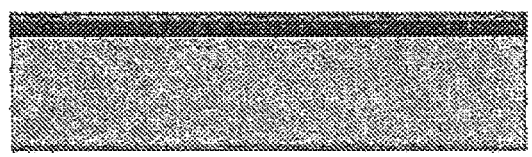
Figure 23:
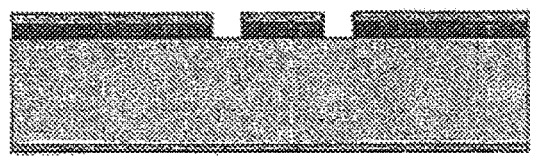
Figure 23:
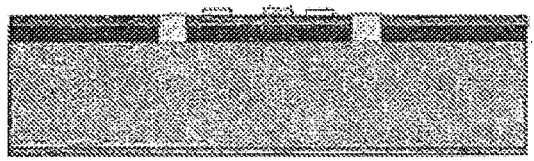
Figure 23:
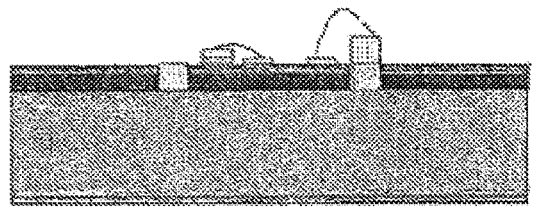
Figure 23:
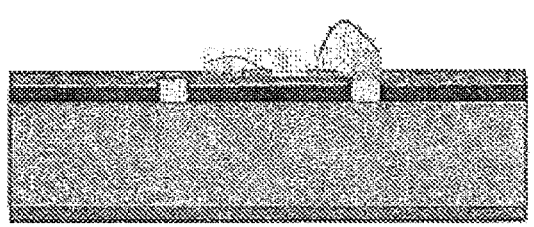
Figure 23:
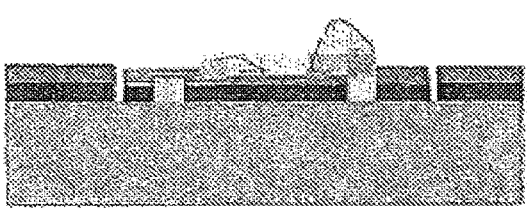
Figure 23:

It is interesting to consider an approach to implantable devices that would involve constructing the devices on silicon with a silicon carbide encapsulant for a truly chronic implant. A possible process is shown in FIG. 23. One of the largest challenges here is ensuring that the PECVD of SiC dues not depole the piezoelectric material. In order to have contamination-free films, it is important to deposit at a minimum temperature of 200° C., but below the Curie temperature of the piezoelectric transducer.

Example 4—Power Transfer to and Backscatter of a Miniaturized Ultrasonic Transducer A set of experiments were carried out with PZT due to the relative ease of obtaining PZT crystals with varying geometry. Metalized PZT sheets of several thicknesses were obtained (PSI-5A4E, Piezo Systems, Woburn, Mass. and PZT 84, APC Internationals, Mackeyville, Pa.), with a minimum PZT thickness of 127 μm. The PZT was fully encapsulated in PDMS silicon for biocompatibility.

The most commonly used method to dice PZT ceramics is to use a wafer dicing saw with an appropriate ceramic blade to cut PZT sheets into individual PZT crystals. The minimum resolution of the cut is determined by the kerf of the blade and can be as small as 30 μm.

Another possible option is to use a laser cutter. Unlike the dicing saw, laser cutting realizes the cuts by focusing a high-power laser beam onto a material, which melts, vaporizes, removes, and scribes the piece. The precision of laser cutting can be down to 10 μm and is limited by the wavelength of the laser. However, for treating sensitive samples such as PZT ceramics, the temperature at the site of cuts can be damaging to the piezoelectric performance of the material. Excimer laser cutting of ceramics uses UV laser to cut with excimer from noble gases, but such laser cutter is extremely expensive and no suitable services are currently available. As a result, a dicing saw was used to perform all the cuts.

In order to drive or extract electrical energy from the PZT, an electrical connection is made to both the top and bottom plates. The materials typically used as an electrode for PZT are silver or nickel. Silver is generally used for a wide variety of non-magnetic and AC applications and silver in the form of flakes suspended in a glass frit is usually screened onto the ceramic and fired. For high electric field DC applications, silver is likely to migrate and bridge the two plates. As a result, nickel, which has good corrosion resistance and does not electro-migrate as readily can be electroplated or vacuum deposited as an alternative.

Both materials can be soldered onto with the appropriate solder and flux. For instance, silver is soluble in tin, but a silver loaded solder can be used to prevent scavenging of silver in the electrode. Phosphor content from the nickel plating can make soldering tricky, but the correct flux can remove surface oxidation. However, when soldering, in order to avoid exceeding the Curie point and depoling the PZT sample, the soldering temperature must be between 240 and 300° C. Even at these temperatures, since the PZT is also pyroelectric, one must be careful not to exceed 2-4 seconds of soldering time.

Alternatively, an electrical connection can be made using either silver epoxy or low temperature soldering using solder paste. Standard two-part silver epoxy can provide a sufficient electrical conductivity and can be cured even at room temperature overnight. However, the joints tend to be fragile and can easily break during testing. The bond can be reinforced by using a non-conductive epoxy as an encapsulation but this additional layer presents a mechanical load to the PZT and can significantly dampen its quality factor. Low-temperature solder paste on the other hand undergoes a phase change between the temperature of 150 and 180° C. and can provide great electrical connection and a bond strength that is comparable to that achieved with flash soldering. Therefore, the low-temperature soldering approach was used.

Wafer dicing is capable of cutting PZTs into small crystals of 10's of μm. However, samples that are smaller than 1 mm in dimension are extremely difficult to handle with tweezers and bond to. In addition, due to the variation in the length of wire used to interface with top and bottom plates of PZT crystals (and therefore parasitic inductance and capacitance introduced by the wire) and the amount of solder paste dispensed across a number of samples, the impedance spectroscope measurements were inconsistent.

Figure 24:
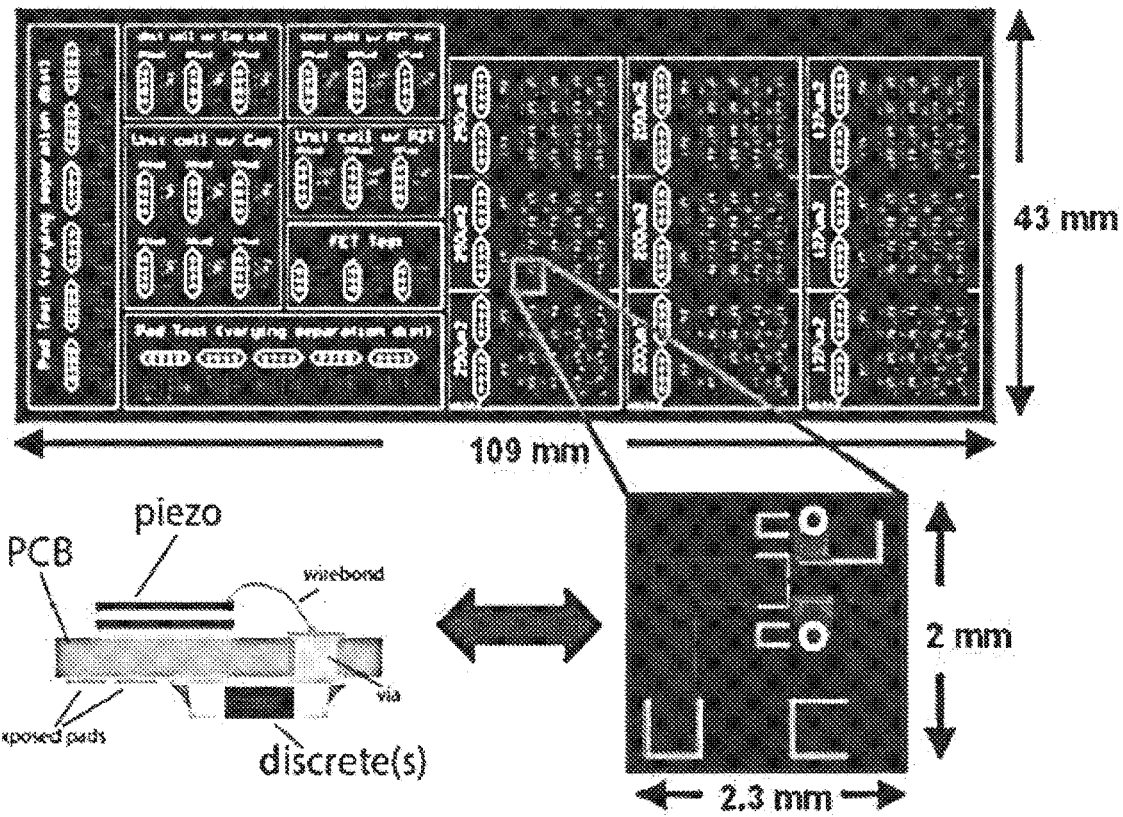
FIG. 24 shows an assembly prototype schematic and PCB.

Therefore, a 31 mil thick two-layer FR-4 PCB where all of the electrical interconnects short and de-embed out the parasitics from the wires and the board was fabricated. The fabricated board, which includes numerous test structures and a module for individually characterizing 127 μm, 200 μm, and 250 μm thick PZT crystals are shown with dimensions in FIG. 24. Each unit cell in the test module contains two pads with specified dimensions on one side of the PCB to interface with the PZT crystals and pads for discrete components for backscattering communication on the opposite side. The pitch between the unit cells is limited by the size of the discrete components and is roughly 2.3 mm×2 mm.

Figure 25:
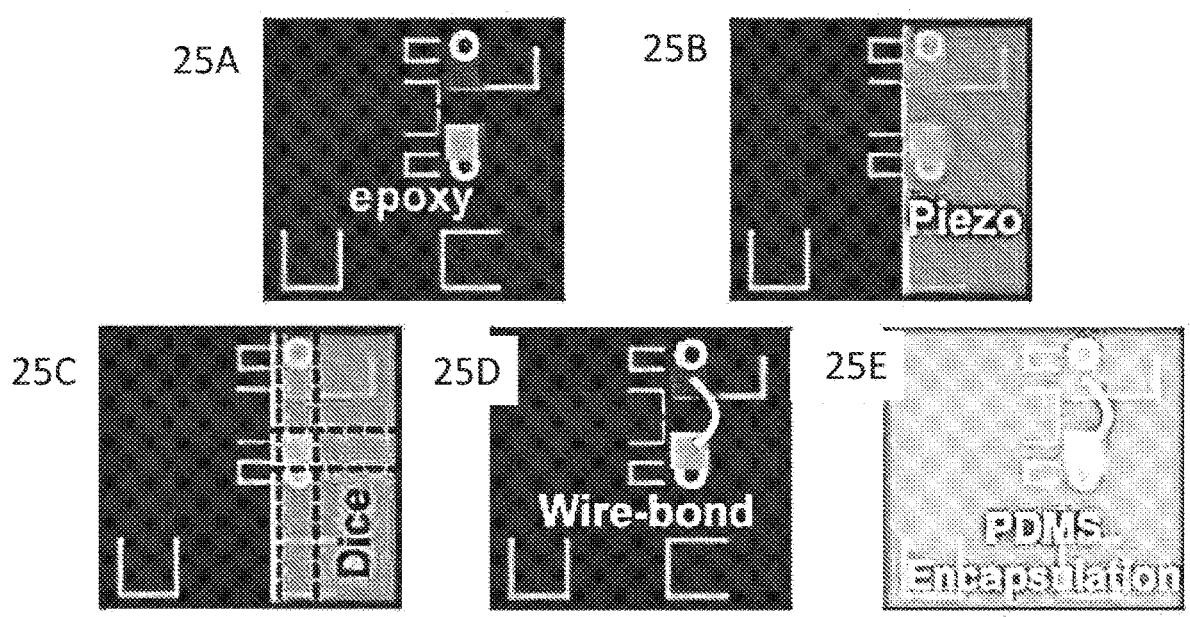
FIG. 25A-E show processing steps to ensure that the desired miniaturized ultrasonic transducer (PZT) dimension is assembled on the PCB. At FIG. 25A, epoxy solder paste is dispensed onto the board. At FIG. 25B, a piezoelectric material is attached to the PCB. At FIG. 25C, the piezoelectric material is diced to form a bulk piezoelectric ultrasonic transducer of the desired size. At FIG. 25D, the ultrasonic transducer is wirebonded to the PCB. At FIG. 25E, the PCB and ultrasonic transducer is encapsulated in PDMS.

In order to avoid directly handling tiny PZT crystals, FIG. 25A-E outline a scalable process flow to bond PZT onto the PCB. As shown in FIG. 25A, the solder paste is dispensed using a pump at a constant pressure and for a controlled amount of time on one of the pads on the top side. The pads are either 250 $\mu m^2$, 200 $\mu m^2$, or 127 $\mu m^2$ based on the thickness of the PZT used. FIG. 25B shows a PZT piece larger than the pad (that can be easily handled) is placed on top to cover the pads. The board and piezo assembly are baked in an oven to cure the solder paste. Therefore, PZT crystals are now bonded to pre-soldered bumped electrodes. FIG. 25C shows a wafer dicing saw makes a total of four cuts along the edges of the pad with the solder paste using alignment markers on the board, with non-bonded areas dropping off and leaving an array of small PZT crystals bonded to the PCB. FIG. 25D shows single wirebond makes an electrical contact between the top plate of the PZT and an electrode on the PCB, completing the circuit. Finally, FIG. 25E shows the entire assembly is encapsulated in PDMS (Sylgard 184, Dow Corning, Midland, Mich.) to protect the wirebond and provide insulation.

Since piezoelectric material is an electro-mechanical structure, its electrical and mechanical properties were characterized. The following details the test setup and techniques to perform such measurements.

Any electrical device can be modeled as a black box using a mathematical construct called two-port network parameters. The properties of the circuits are specified by a matrix of numbers and the response of the device to signals applied to its input can be calculated easily without solving for all the internal voltages and currents in the network. There are several different types of two-port network parameters, such as Z-parameters, Y-parameters, S-parameters, and ABCD-parameters, etc. and the conversion between different parameters can be easily derived. The apparatus that enables us to extract these parameters is called a vector network analyzer (VNA). A VNA incorporates directional couplers to decompose the voltage in each port into incident and reflected waves (based on impedance mismatching), and calculate the ratio between these waves to compute scattering or S-parameters.

Figure 26:
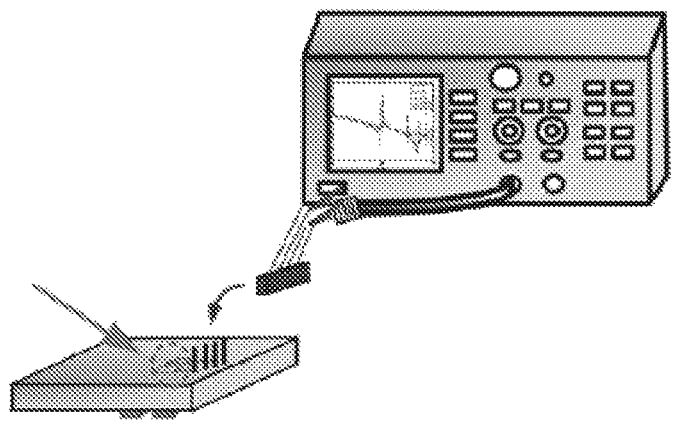
FIG. 26 shows a schematic for measuring electrical impedance with a vector network analyzer (VNA)

Before performing measurements using a VNA, one must calibrate the instrument since the internal directional couples are non-ideal. Calibration also allows us to move the reference plane of the measurement to the tips of the cable, i.e., calibrate out parasitics from the cable. There are several calibration standards but the most commonly used is open, short, and load calibration procedures. The measurement schematic is shown in FIG. 26. Alligator clips, which are soldered onto the ends of the coaxial cable, are used to interface with the top/bottom plates. The parasitics from the clips were not significant below 100 MHz.

As an example, a VNA (E5071C ENA, Agilent Technologies, Santa Clara, Calif.) was used to measure the electrical properties of a $(250~\mu m)^3$ PZT crystal. It was noted that the measured capacitance of the PZT crystal vastly differs from the capacitance expected from a simple parallel-plate capacitance model due to significant parasitic capacitances from the PCB and the fixture (clip and connector). Since the VNA coefficients from the calibration step previously outlined only moved the measurement plane to the tips of the cable, open/short/load calibration structures fabricated on the same board were used to include the board and fixture parasitics. The measured PZT response matched the expected response after calibration.

Figure 27:
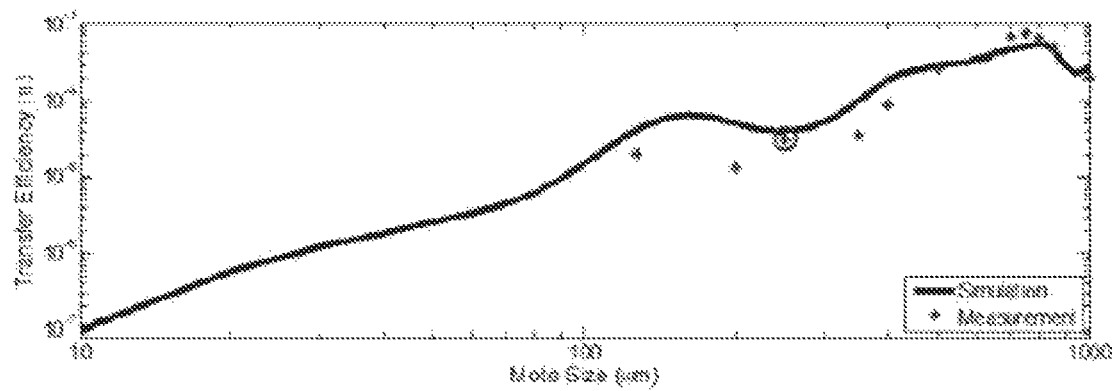
FIG. 27A shows that the measured power transfer efficiency at various bulk piezoelectric ultrasonic transducer sizes matches simulated behavior.
FIG. 27B shows that the measured impedance spectroscopy of a PZT crystal matches a simulation.
FIG. 27C show that the frequency response of harvested power of the miniaturized ultrasonic transducer is approximately 6.1 MHz.
Figure 27:
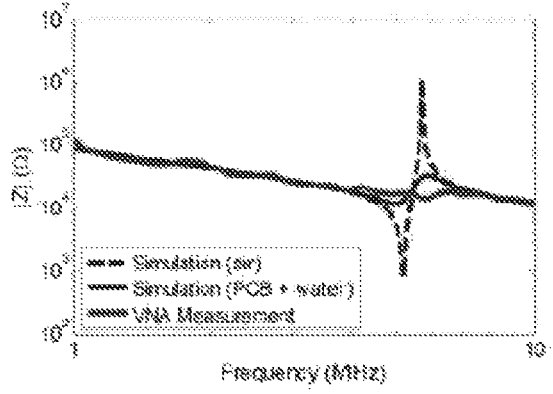
Figure 27:
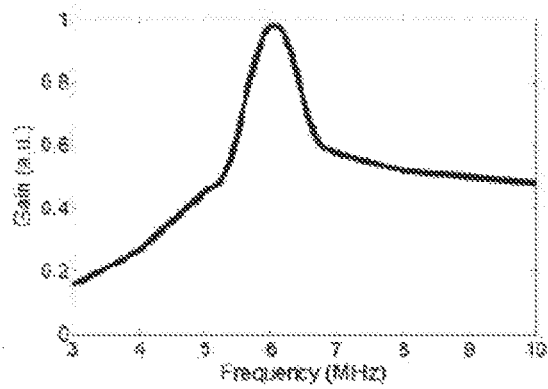

Using this calibration technique, the impedance of the PZT can be plotted as a function of frequency, as shown in FIG. 27B. From this plot, however, it is extremely difficult to determine whether there is any electro-mechanical resonance. When the simulation result with air backing (no mechanical clamping) was overlaid, it was noticed that the impedance spectroscopy matches well with the measurement at low and high frequencies, with the exception of noticeable peak at resonant frequency of roughly 6 MHz and its harmonics. Upon clamping and loading one side of PZT with PCB (FR-4), it was seen that a significant dampening of the resonant peaks from air backing. Despite a lack of observable resonance in the measurement, a small blimp around 6 MHz was observed, and the mechanical quality factor $Q_m$ can be calculated using the following equations, $$Q_m = \frac{f_a^2}{2Z_r C_p (f_a^2 - f_r^2)}$$

where $f_a$ and $f_r$ represent anti-resonant (where impedance is maximized) and resonant frequency (where impedance is minimized), $Z_r$ represents an impedance at resonance, and $C_p$ is the low-frequency capacitance. The calculated quality factor from the measurement is roughly 4.2 compared to 5.1 in simulation. According to the datasheet, the unloaded Q of the PZT is ~500, indicating that FR-4 backing and wirebonds are causing significant degradation of the quality factor. Despite the drastic reduction in the mechanical Q of the PZT crystals, experiments showed that the backscattered signal level only decreased by roughly ~19.

In the electrical characterization setup, the VNA has a built-in signal generator to provide the input necessary for characterization. In order to perform acoustic characterization of PZT, acoustic waves were generated and launched onto the sample to use as an input. This can be achieved with commercially available broadband ultrasonic transducers.

Figure 28:
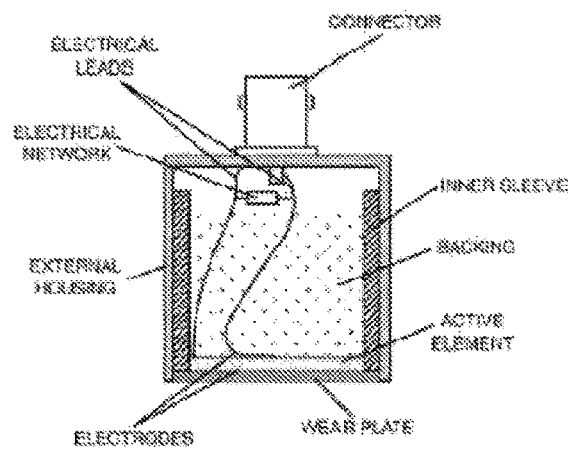
FIG. 28 is a schematic of an exemplary ultrasonic transducer that can be used as part of an interrogator.

FIG. 28 shows the composition of a representative transducer, which consists of a piezoelectric active element, backing, and wear plate. The backing is usually made from a material with high attenuation and high density to control the vibration of the transducer by absorbing the energy radiating from the back face of the active element while the wear plate is used to protect the transducer element from the testing environment and to serve as a matching layer.

Figure 29:
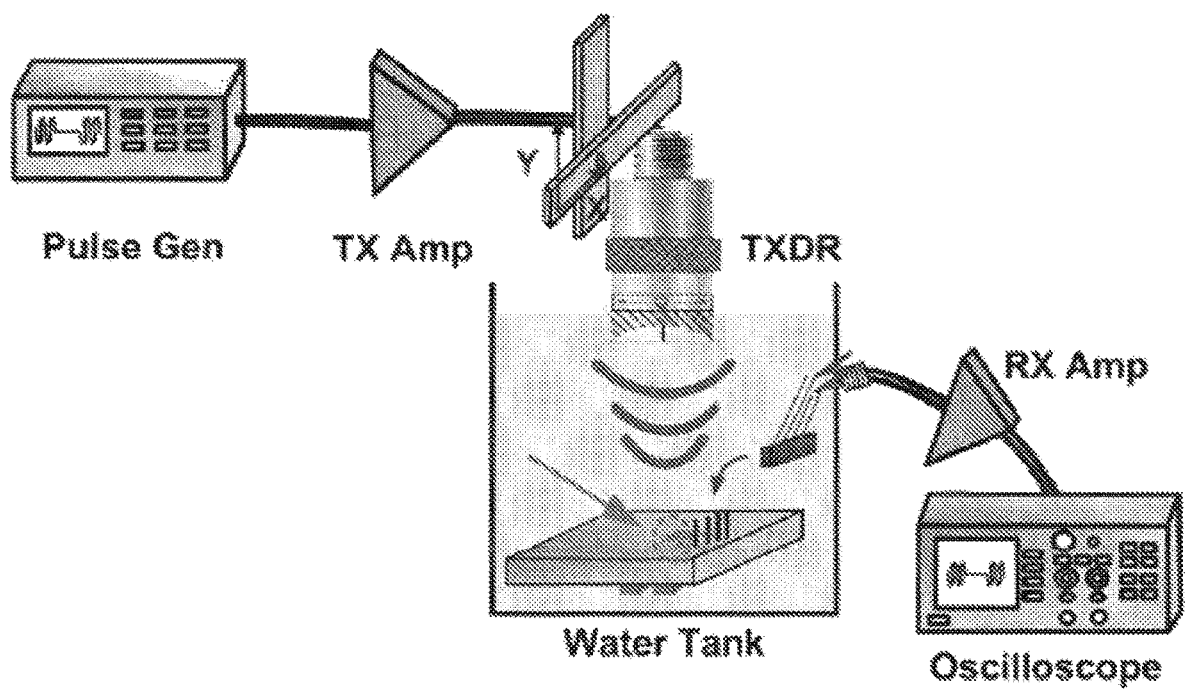
FIG. 29 is a schematic of a setup for acoustic characterization with a calibrated ultrasonic transducer for power delivery verification. The ultrasonic wave receiver is separate from the ultrasonic wave transmitter.

Ultrasonic power transfer tests were performed using the home-built setup shown in FIG. 29. A 5 MHz or 10 MHz single element transducer (6.3 mm and 6.3 mm active area, respectively, ~30 mm focal distance, Olympus, Waltham, Mass.) was mounted on a computer-controlled 2-axis translating stage (VelMex, Bloomfield, N.Y.). The transducer output was calibrated using a hybrid capsule hydrophone (HGL-0400, Onda, Sunnyvale, Calif.). Assembly prototypes were placed in a water container such that transducers could be immersed in the water at a distance of approximately 3 cm directly above the prototypes. A programmable pulse generator (33522B, Agilent Technologies Santa Clara, Calif.) and radio frequency amplifier (A150, ENI, Rochester, N.Y.) were used to drive transducers at specified frequencies with sinusoidal pulse trains of 10-cycles and a pulse-repetition frequency (PRF) of 1 kHz. The received signals were amplified with a radio frequency amplifier (BT00500-AlphaS-CW, Tomco, Stepney, Australia), connected to an oscilloscope (TDS3014B, Tektronix, Beaverton OR) to collect ultrasound signal and record them using MATLAB.

Figure 30A:
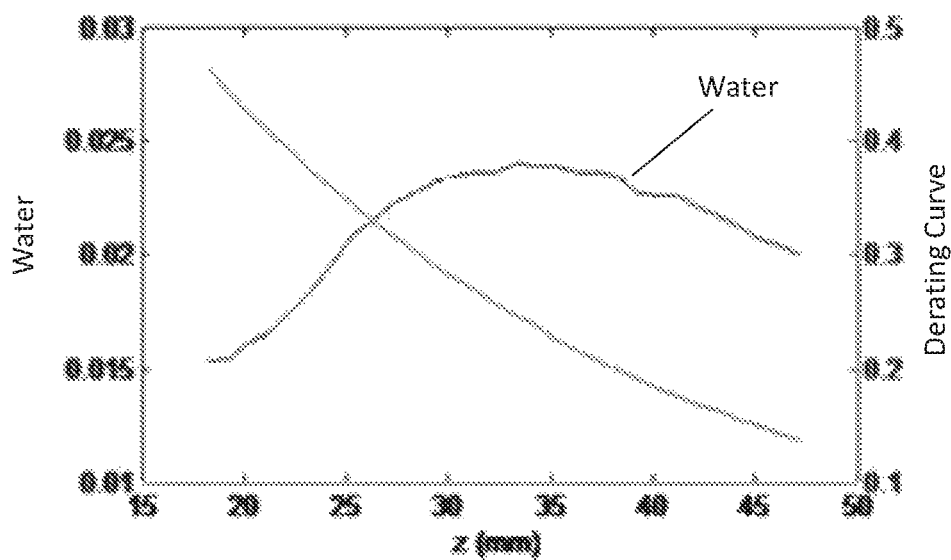
FIG. 30A shows the output power of a 5 MHz transducer as the hydrophone is moved away from the transducer's surface.
Figure 30B:
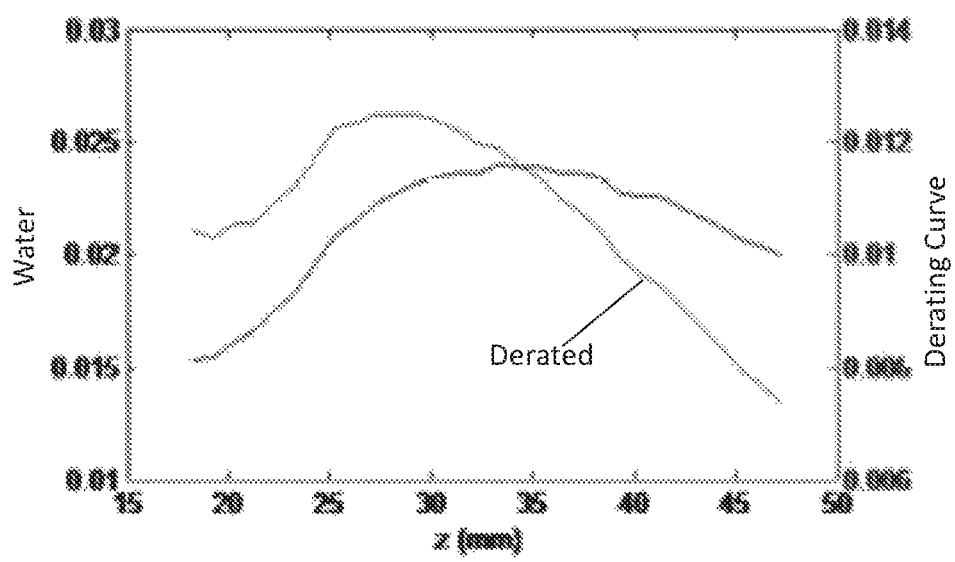
FIG. 30B shows that the de-rated peak is shifted to the left in relation to the water peak.
Figure 31A:
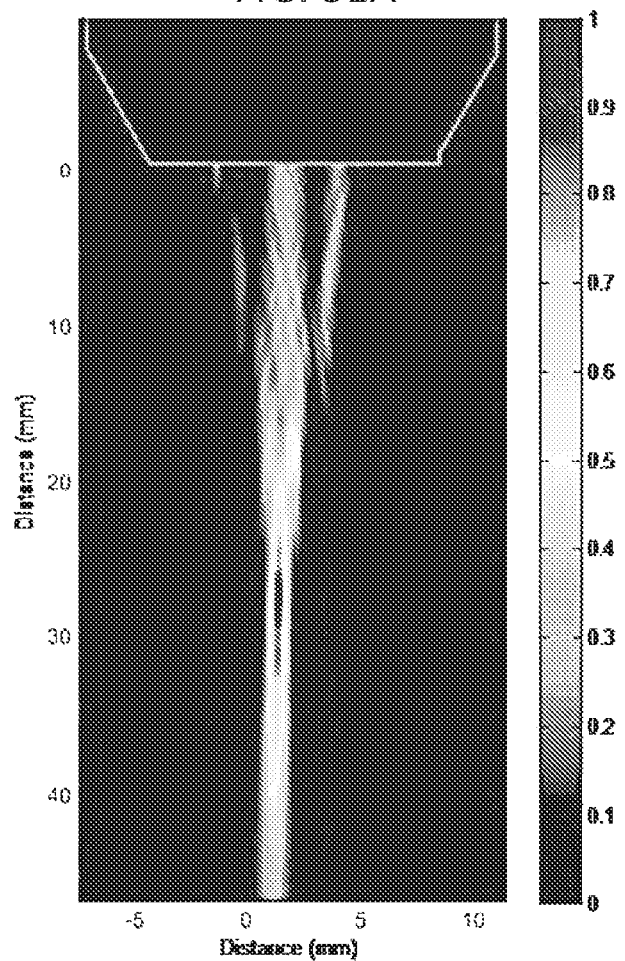
FIG. 31A shows the XZ cross-section of the transducer output, illustrating a Rayleigh distance and a clear transition from the near-field to far-field propagation.
Figure 31B:
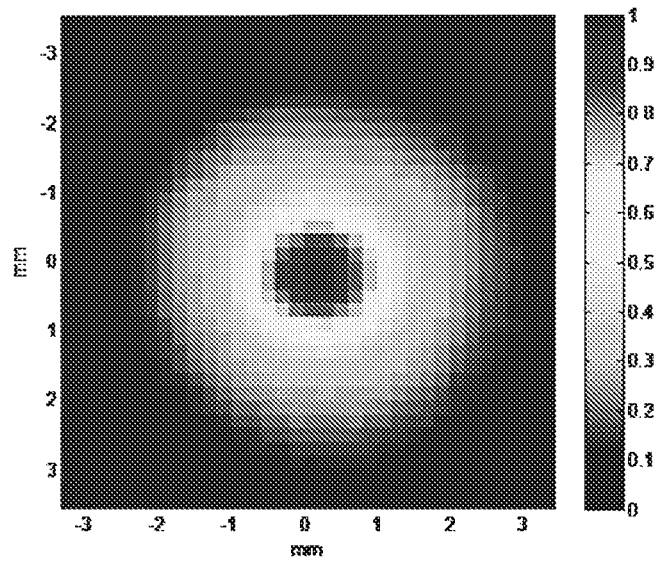
FIG. 31B shows the XY beam cross-section showing a 6 dB bandwidth of the beam at 2.2 mm.

FIGS. 30A-B show a representative measurement of the output power of the 5 MHz transducer as a function of the distance between the surface of the transducer and the hydrophone (z-axis). The peak pressure in water was obtained at ~33 mm away from the transducer's surface (FIG. 30A) while the de-rated peak (with 0.3 dB/cm/MHz) was at ~29 mm (FIG. 30B). FIG. 31A shows the de-rated XZ scan of the transducer output, which show both near-field and far-field beam patterns and a Rayleigh distance or a focal point at ~29 mm, matching the derated peak in FIG. 30B. FIG. 31B shows a XY cross-sectional scan of the beam at the focal point of ~29 mm, where the 6 dB beamwidth measured roughly 2.2 mm.

The total integrated acoustic output power of the transducer at various frequencies over the 6 dB bandwidth of the beam was nominally kept at a spatial-peak temporal-average $I_{SPTA}$ of 29.2 $\mu W/cm^2$, resulting in a total output power of ~1 $\mu W$ at the focal point, with a peak rarefaction pressure of 25 kPa and a mechanical index (MI) of 0.005. Both the de-rated $I_{sm}$ and MI were far below the FDA regulation limit of 720 $mW/cm^2$ and 1.9, respectively (FDA 2008).

FIG. 27A shows the measured power delivery efficiency of the fully assembled prototype with cable loss calibrated out for various implantable device transducer sizes as compared to analytical predictions made for this same setup. Measured results matched the simulated model behavior very closely across all transducer sizes, with the exception of a few smaller transducer dimensions, likely due to the sensitivity to transducer position and the ultrasound beamwidth. The measured efficiency of the link for the smallest PZT crystal $(127 \: \mu m)^3$ was $2.064 \times 10^{-5}$, which resulted in 20.64 pW received at the transducer nominally. A maximum of 0.51 µW can be recovered at the transducer if the transmit output power density was kept at 720 mW/cm$^2$. Such low power level harvested by the PZT is mainly due to the extreme inefficiency of broadband transducers that were used for the experiments; dedicated, custom-made transducers at each transducer dimension with optimal electrical input impedance could result in more than 2 orders of magnitude improvement in the harvested power level as predicted by the simulation model.

The frequency response of electrical voltage harvested on a $(250 \: \mu m)^3$ PZT crystal is shown in FIG. 27C. The resonant frequency was measured to be at 6.1 MHz, which matches the shift in the resonant frequency predicted for a cube due to Poisson's ratio and the associated mode coupling between resonant modes along each of the three axes of the cube. Furthermore, the calculated Q of 4 matched the electrically measured Q of the PZT.

The experimental result indicate that the analytical model for power coupling to very small PZT nodes using ultrasound is accurate down to at least ~100 µm scale and likely lower. It remains to be seen just how mall a transducer can be fabricated before loss of function. Note that measurements of even smaller nodes (<127 µm) were limited not by the prototype assembly process but by commercial availability of PZT substrates. Moving forward, the considerable volume of research and techniques that has gone into micro- and nanoelectromechanical RF resonators was be used (see Sadek et al., *Wiring nanoscale biosensors with piezoelectric nanomechanical resonators*, Nano Lett., vol. 10, pp. 1769-1773 (2010); Lin et al., *Low phase noise array-composite micromechanical wine-glass disk oscillator*, IEEE Elec. Dev. Meeting, pp. 1-4 (2005)) and thin-film piezoelectric transducer (see Trolier-McKinstry et al., *Thin film piezoelectrics for MEMS*, J. Electroceram., vol. 12, pp. 7-17 (2004)) to facilitate extremely small (10's of µm) transducers and to truly assess the scaling theory.

Example 5—Beamforming Using Interrogator Ultrasonic Transducer Array

In this example, an ultrasonic beamforming system capable of interrogating individual implantable sensors via backscatter in a distributed, ultrasound-based recording platform is presented. A custom ASIC drives a 7×2 PZT transducer array with 3 cycles of 32V square wave with a specific programmable time delay to focus the beam at the 800 µm neural dust mote placed 50 mm away. The measured acoustic-to-electrical conversion efficiency of the receive mote in water is 0.12% and the overall system delivers 26.3% of the power from the 1.8V power supply to the transducer drive output, consumes 0.75 µJ in each transmit phase, and has a 0.5% change in the backscatter per volt applied to the input of the backscatter circuit. Further miniaturization of both the transmit array and the receive mote can pave the way for a wearable, chronic sensing and neuromodulation system.

In this highly distributed and asymmetric system, where the number of implanted devices outnumbers the interrogating transceivers by an order of magnitude, beamforming can be used to efficiently interrogate a multitude of implantable devices. Research into beamforming algorithms, trade-offs, and performance in the implantable device platform has demonstrated that cooperation between different interrogators is useful for achieving sufficient interference suppression from nearby implantable devices. See Bertrand et al., *Beamforming approaches for untethered ultrasonic neural dust motes for cortical recording: a simulation study*, IEEE EMBC, 2014, pp. 2625-2628 (August 2014). This example demonstrates a hardware implementation of an ultrasonic beamforming system for the interrogator and implantable device system shown in FIG. 2A. The ASIC (see, e.g., Tang et al., *Integrated ultrasonic system for measuring body-fat composition*, 2015 IEEE International Solid-State Circuits Conference—(ISSCC) Digest of Technical Papers, San Francisco, Calif., 2015, pp. 1-3 (February 2015); Tang et al., *Miniaturizing Ultrasonic System for Portable Health Care and Fitness*, IEEE Transactions on Biomedical Circuits and Systems, vol. 9, no. 6, pp. 767-776 (December 2015)), has 7 identical channels, each with 6 bits of delay control with 5 ns resolution for transmit beam-forming, and integrates high-voltage level shifters and a receive/transmit switch that isolates any electrical feed-through.

The ASIC operates with a single 1.8V supply and generates a 32V square wave to actuate piezoelectric transducers using integrated charge pumps and level shifters. The system delivers ~32.5% of the power from the 1.8V supply to the 32V output voltage and ~81% from 32V to the output load (each transducer element is 4.6 pF). The ASIC block diagram is shown in FIG. 2A; the circuit details to enable such low energy consumption per measurement can be found in Tang et al., *Integrated ultrasonic system for measuring body-fat composition*, 2015 IEEE International Solid-State Circuits Conference—(ISSCC) Digest of Technical Papers, San Francisco, Calif., 2015, pp. 1-3 (February 2015). The ASIC is fabricated in 0.18 µm CMOS with high voltage transistors. The chip area is 2.0 mm$^2$ and includes the complete system except for the digital controller, ADCs, and two off-chip blocking capacitors.

The design of a transducer array is a strong function of the desired penetration depth, aperture size, and element size. Quantitatively, the Rayleigh distance, R, of the array can be computed as follows:

$$R = \frac{D^2}{4\lambda}$$

where D is the size of the aperture and λ is the wavelength of ultrasound in the propagation medium. By definition, Rayleigh distance is the distance at which the beam radiated by the array is fully formed; in other words, the pressure field converges to a natural focus at the Rayleigh distance and in order to maximize the received power, it is preferable to place the receiver at one Rayleigh distance where beam spreading is the minimum.

The frequency of operation is optimized to the size of the element. A preliminary study in a water tank has shown that the maximum energy efficiency is achieved with a $(800 \: \mu m)^3$ PZT crystal, which has a resonant frequency of 1.6 MHz post-encapsulation, resulting in λ ~950 µm. The pitch between each element is chosen to be an odd multiple of half wavelength in order to beamform effectively. As a result, for this demonstration of beamforming capabilities, the overall aperture is ~14 mm, resulting in the Rayleigh distance of 50 mm. At 50 mm, given the element size of 800 µm, each element is sufficiently far from the field (R=0.17 mm); therefore, the beam pattern of an individual element should be omni-directional enough to allow beamforming.

There are several transmit and receive beamforming techniques that can be implemented. In this example, time delay-and-sum transmit beamforming algorithm is chosen, such that the signals constructively interfere in the target direction. This algorithm is capable of demonstrating beam-steering and maximal power transfer to various implantable devices. In order to accommodate backscatter communication to multiple implantable devices simultaneously, more sophisticated algorithms may be required. These can include delay-and-sum beamforming, linearly constrained minimum-variance beamforming, convex-optimized beamforming for a single beam, 'multicast' beamforming w/convex optimization, maximum kurtosis beamforming, minimum variance distortionless response robust adaptive beamforming, polyadic tensor decomposition, and deconvolution of mote impulse response from multi-Rx-channel time-domain data. The detailed treatment of one aspect of this problem is described in Bertrand et al., *Beamforming approaches for untethered ultrasonic neural dust motes for cortical recording: a simulation study*, IEEE EMBC, 2014, pp. 2625-2628 (August 2014).

Each of the 7 channels is driven by 3 cycles of 32V square wave with a specific programmable time delay such that the energy is focused at the observation distance of 50 mm. The time delay applied to each channel is calculated based on the difference in the propagation distance to the focus point from the center of the array and the propagation speed of the ultrasound wave in the medium.

Ultrasim was used to characterize the propagation behavior of ultrasound wave in water with the 1D array described above. Simulated XY (FIG. 32A) and XZ (FIG. 32B) cross-sectional beam patterns closely match the measurement as shown, despite not modeling the PDMS encapsulation.

Water is used as the medium for measuring the beamforming system as it exhibits similar acoustic properties as the tissue. Pre-metalized Lead Zirconate Titanate (PZT) sheets (APC International, Mackeyville, Pa.) are diced with a wafer saw to 800 µm×800 µm×800 µm crystals (parallel capacitance of 4.6 pF each), which is the size of each transmit element. Each PZT element is electrically connected to the corresponding channel in the ASIC by using a conductive copper foil and epoxy for the bottom terminal and a wirebond for the top terminal. The array is encapsulated in PDMS (Sylgard 184, Dow Corning, Midland, Mich.) to protect the wirebond and provide insulation. The quality factor of the PZT crystal post encapsulation is ~7. The array is organized into 7 groups of 2×1 elements, with the pitch of ~5/2$\lambda$~2.3 mm. The array measures approximately 14 mm×3 mm Finally, the entire assembly is encased in a cylindrical tube with the diameter of 25 mm and the height of 60 mm and the tube is filled with water.

The transducer array's 2D beam pattern and output are calibrated using a capsule hydrophone (HGL-0400, Onda, Sunnyvale, Calif.). The hydrophone is mounted on a computer-controlled 2D translating stage (VelMex, Bloomfield, N.Y.). The hydrophone has an acceptance angle (-6 dB at 5 MHz) of 30°, which is sufficient to capture the beam given the transmission distance of 50 mm and the scan range (±4 mm).

Figure 32A:
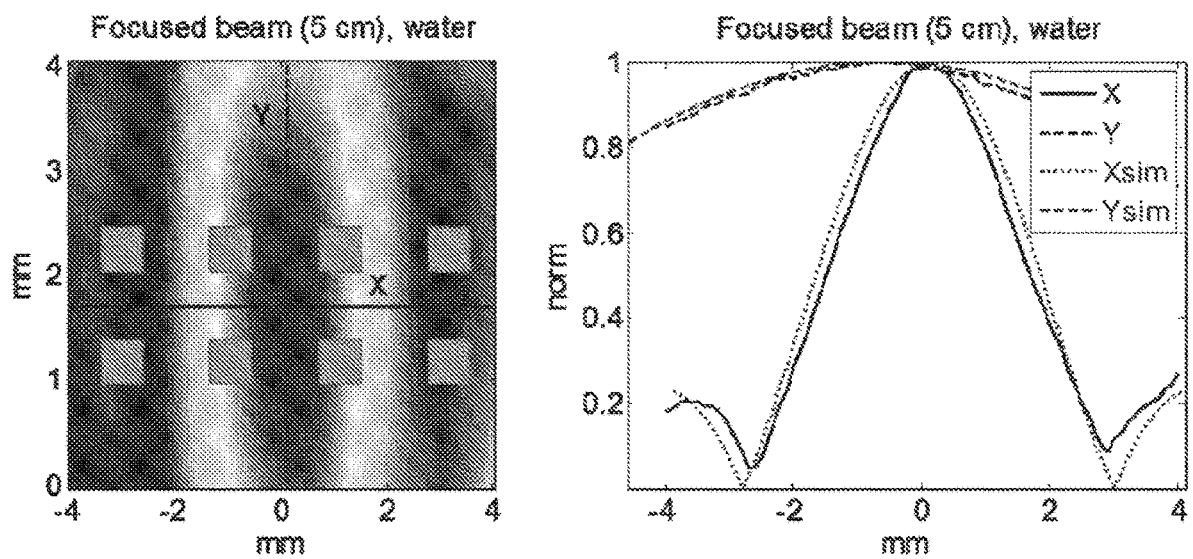
FIG. 32A shows a focused 2D beam pattern from a transducer array in the XY plane. The measured beam approximates the simulated beam in both the X and Y dimensions.
Figure 32B:
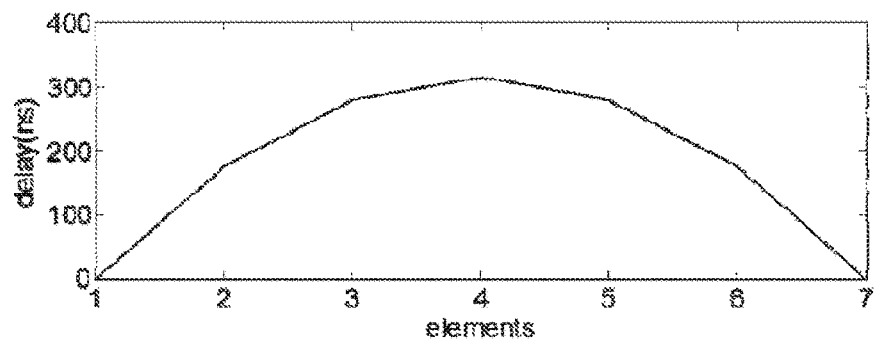
FIG. 32B shows the delay time applied to each transducer element in the ultrasonic transducer array.
Figure 32C:
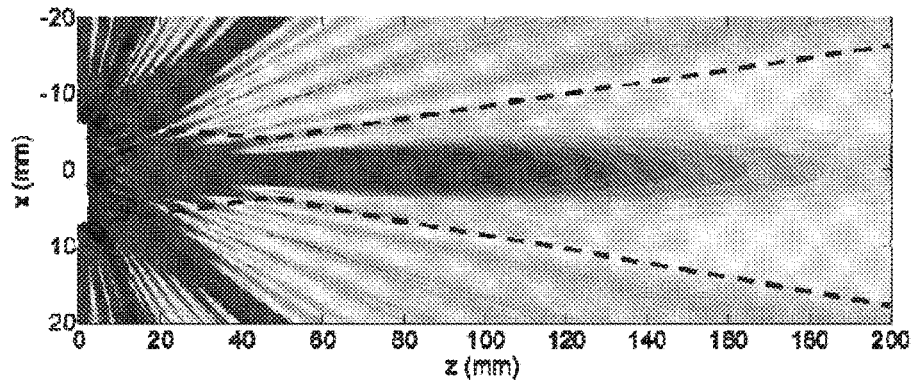
FIG. 32C shows a simulated 2D XZ cross-sectional beam pattern.

The measured XY cross-sectional beam pattern with the overlay of the array is shown in FIG. 32A. The applied delay for each transducer in the array (element) is shown in FIG. 27B. The -6 dB beamwidth at the focal point is 3.2 mm ~3$\lambda$. The flexibility of the ASIC allows for both wide and granular programming of the delays. The peak pressure level of the array at 50 mm before and after beamforming is ~6 kPa and ~20 kPa, respectively. The 3× in the transmitted output pressure wave after beamforming matches the simulation. The simulation also verifies that the Rayleigh distance of the array is at 50 mm as shown in FIG. 32C.

Figure 33A:
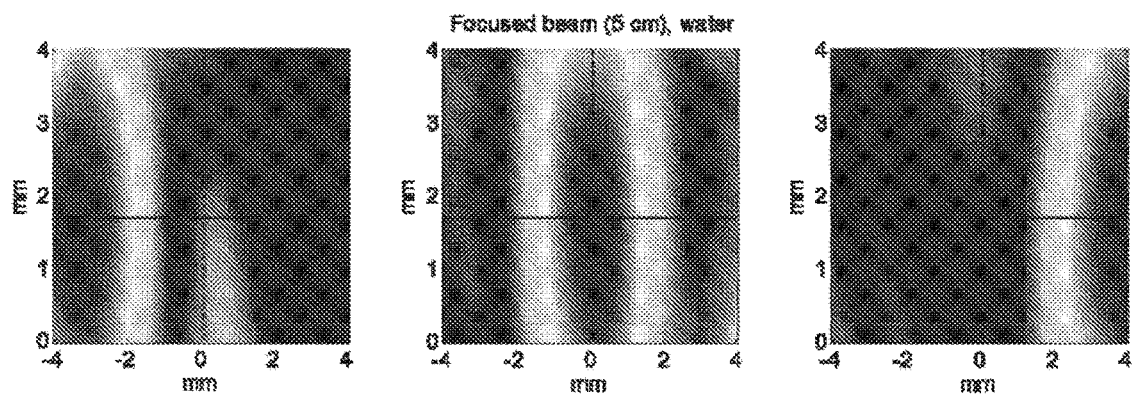
FIG. 33A shows beam steering of an ultrasonic wave beam transmitted from a transducer array. Underneath each beam pattern is the delay for each transducer in the array to obtain the measured beam pattern, as shown in FIG. 33B.
Figure 33B:
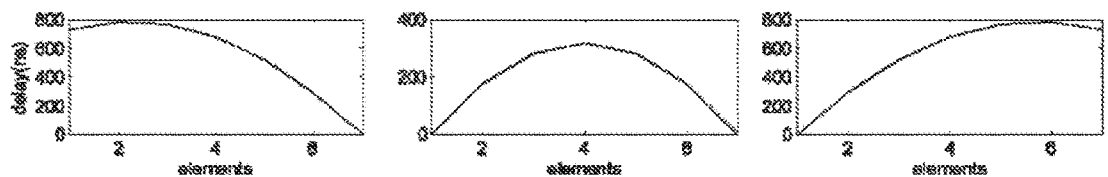
FIG. 33C shows the 1D beam pattern in the X-axis for each beam pattern shown in FIG. 33A. The measured beam pattern closely approximates the simulated beam pattern.
Figure 33C:
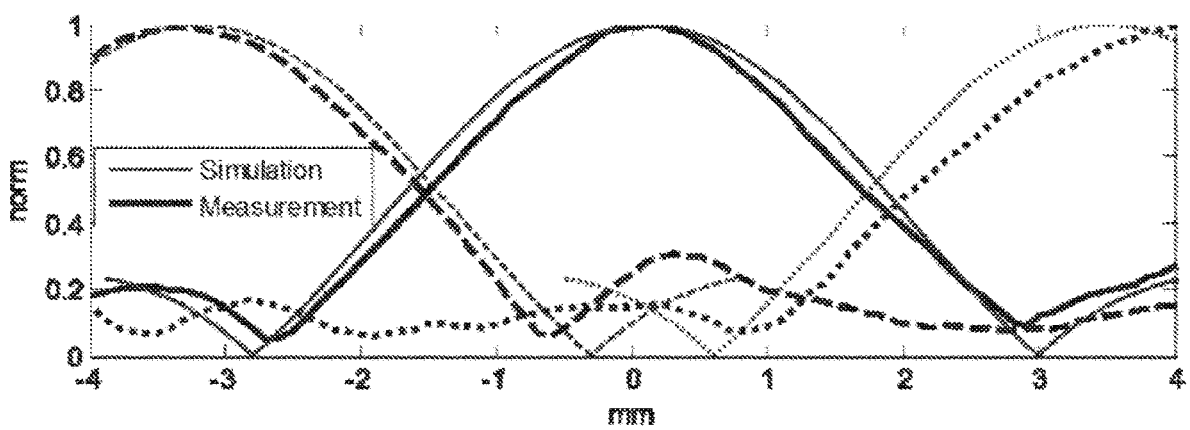

Additionally, in order to verify the capability to interrogate multiple implantable devices, it was verified the beam steering capability of the array as shown in FIG. 33A (showing beam steering at three different positions in the XY-plane), with the time delay for each beam position shown underneath in FIG. 33B. The 1D beam steering matches very closely with the simulation, as shown in FIG. 33C. Note that the beam steering range is limited to ±4 mm due to the mechanical construct of the array, rather than the electronic capability.

The hydrophone is replaced with an implantable device (with a 800 µm×800 µm×800 µm bulk piezoelectric transducer) and placed at the transmission distance of 50 mm to verify the power link. The open-circuit peak-to-peak voltage measured at the mote is 65 mV, for a transmit pulse-duration of 2.56 µs. The spatial peak average acoustic power integrated over the -6 dB beamwidth at the focal point is 750 µW, which is 0.005% of the FDA safety limit. The maximum harvestable power at the mote is 0.9 µW, resulting in the measured acoustic-to-electrical conversion efficiency of 0.12%. The measured result is in agreement with the link model (see Seo et al., *Model validation of untethered ultrasonic neural dust motes for cortical recording*, J. Neurosci. Methods, vol. 244, pp. 114-122 (2015)). The system delivers 26.3% of the power from the 1.8V power supply to the transducer drive output (defined as driving efficiency) and consumes 0.75 µJ in each transmit phase.

The ultrasonic backscatter communication capability of the system is verified by measuring the difference in the backscattered voltage level as the input to the backscatter circuit (see Seo et al., *Model validation of untethered ultrasonic neural dust motes for cortical recording*, J. Neurosci. Methods, vol. 244, pp. 114-122 (2015)), and is adjusted with a DC power supply. The transmit time and the period of the system are 3 µs and 80 µs, leaving a ~77 µs window for reception. A 2×1 element in the center of the array is used for receiving the backscatter. The output of the receive crystals is amplified and digitized for processing. The measured backscatter sensitivity is ~0.5% per volt applied to the input of the backscatter circuit, which is in agreement with the simulation. The overall performance of the system is summarized in Table 4.

TABLE 4

Summary of System Performance

| | |
|---|---|
| Supply voltage | 1.8 V |
| Output voltage | 32 V |
| Number of channels | 7 |
| Operating frequency | 1.6 MHz |
| Charge pump + level shifter efficiency | 26.3% |
| Acoustic-to-Electrical efficiency | 0.12% |
| Backscatter change | 0.5%/V |
| Energy per transmit phase | 0.75 µJ |

The measurements with the ultrasonic beamforming system suggest that transmit beamforming alone can provide sufficient signal-to-noise ratio (SNR) to enable multiple sensors interrogation in the neural dust platform. The decrease in the SNR with the miniaturization of the dust mote can be largely mitigated by implementing receive beamform. Furthermore, in order to increase the rate of interrogation, one could explore an alternative means of multiplexing, such as spatial multiplexing where multiple motes are interrogated simultaneously with the same transmit beam. However, it is important to consider the system design tradeoff between processing/communication burden to power consumption. Additionally, sufficient suppression of interferences from nearby dust motes is necessary to achieve the required SNR.

The acoustic-to-electrical efficiency at 0.12% currently dominates the efficiency $$\left(\frac{P_{harvested}}{P_{1.8V\ supply}}\right)$$

or tne overall system. Despite such low efficiency of the power link, if ~1% of the FDA safety regulation (spatial peak average of 1.9 W/cm$^2$) can be outputted, it is possible harvest up to 0.92V peak-to-peak voltage and 180 μW at the 800 μm ultrasonic transducer 50 mm away in water.

Furthermore, the low efficiency of the power link in this demonstration is attributed to such large transmission distance, as determined by the array aperture and the element size. For peripheral nerve intervention, for example, the desired transmission distance is approximately 5 mm, which includes the thickness of skin, tissue, etc. In order to be at the far field of the array, the aperture should be ~4.4 mm. Further scaling of each element can reduce the overall dimensions of the array aperture and the transmission distance down to the desired 5 mm Simulation indicates that acoustic-to-electrical efficiency up to 1% can be achieved in water with a 100 μm receive ultrasonic transducer.

Figure 34:
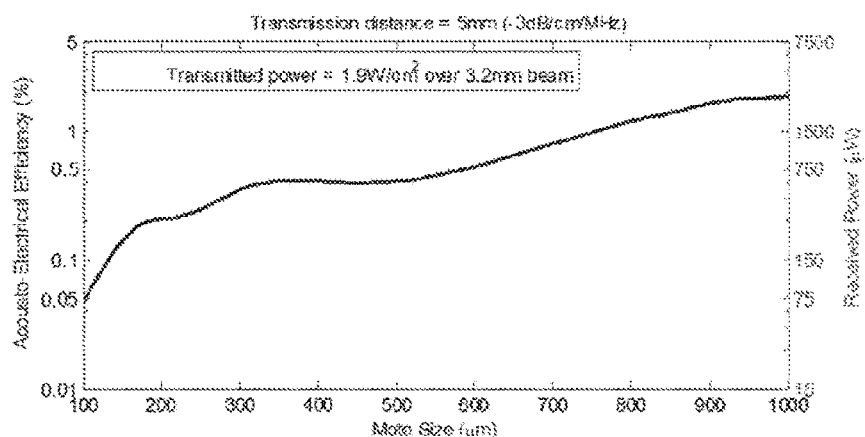
FIG. 34 shows a simulated scaling of miniaturized ultrasonic transducer link efficiency and received power at 5 mm in tissue.

For transmission in tissue, assuming 3 dB/cm/MHz loss in tissue, FIG. 34 shows the scaling of both link efficiency and received power level given operation at 1% of the FDA safety limit. Despite this rather conservative loss, at 100 μm, the simulation indicates that it is possible to harvest up to 0.6V peak-to-peak voltage and 75 μW. Therefore, wireless power transfer in tissue using this platform is feasible. Furthermore, this power level is sufficient to operate highly efficient, low-power energy harvesting circuits and charge pumps, similar to the ASIC presented here, to output voltages that are suitable for electrically stimulating nearby neurons and detecting physiological conditions using sensors.

Example 6—Tracking of Movement and Temperature Drift of Implantable Devices

An implantable device was manufactured with on a 50 μm thick polyimide flexible printed circuit board (PCB) with a ultrasonic transducer piezocrystal (0.75 mm×0.75 mm×0.75 mm) and a custom transistor (0.5 mm×0.45 mm) attached to the topside of the board with a conductive silver paste. Electrical connections between the components are made using aluminum wirebonds and conductive gold traces. Exposed gold recording pads on the bottom of the board (0.2 mm×0.2 mm) are separated by 1.8 mm and make contact on the nerve or muscle to record electrophysiological signals. Recorded signals are sent to the transistor's input through micro-vias. Additionally, some implants were equipped with 0.35 mm-wide, 25 mm-long, flexible, compliant leads with test points for simultaneous measurement of both the voltage across the piezocrystal and direct wired measurement of the extracellular potential across the electrode pair used by the ultrasonic transducer (this direct, wired recording of extracellular potential as the ground truth measurement is referred to below, which is used as a control for the ultrasonically reconstructed data). The entire implant is encapsulated in a medical grade UV-curable epoxy to protect wirebonds and provide insulation. A single implantable device measures roughly 0.8 mm×3 mm×1 mm. The size of the implants is limited only by our use of commercial polyimide backplane technology, which is commercially accessible to anyone; relying on more aggressive assembly techniques with in-house polymer patterning would produce implants not much larger than the piezocrystal dimensions (yielding a ~1 mm$^3$ implant).

Figure 35A:
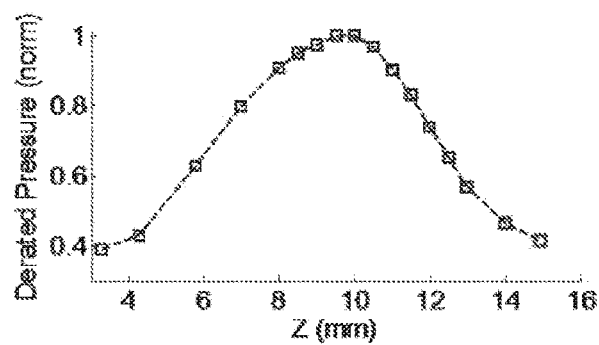
FIG. 35A shows the de-rated normalized peak pressure as a function of distance from the surface of an exemplary transducer has a de-rated focus at about 8.9 mm at 1.85 MHz.
Figure 35B:
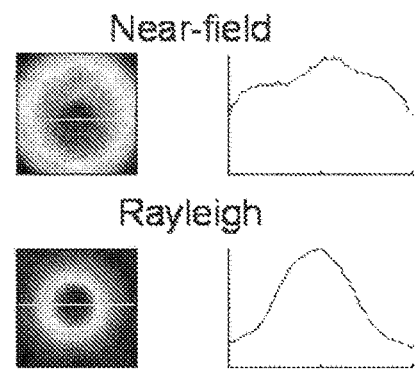
FIG. 35B shows the XY cross-sectional beam patterns and the corresponding 1D voltage plot at y=0 at near-field, Rayleigh distance, and far-field. The patterns show the beam focusing at the Rayleigh distance.
Figure 35C:
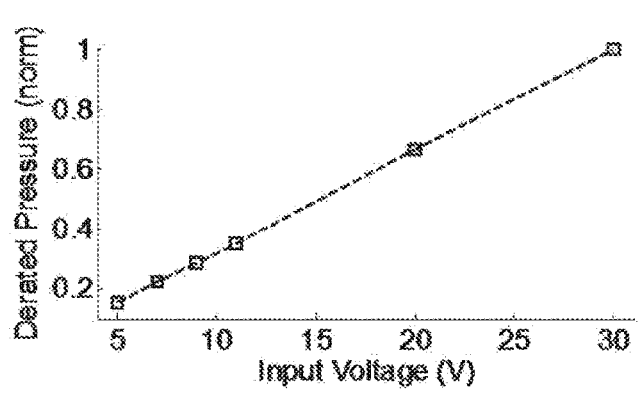
FIG. 35C shows that the transducer's output pressure was a linear function of input voltage (up to 32 V peak-to-peak).

An external, ultrasonic transceiver board interfaces with the implantable device by both supplying power (transmit (TX) mode) and receiving reflected signals (receive (RX) mode). This system is a low-power, programmable, and portable transceiver board that drives a commercially available external ultrasonic transducer (V323-SU, Olympus, Waltham, Mass.). The transceiver board exhibited a de-rated pressure focus at ~8.9 mm (FIG. 35A). The XY cross-sectional beam-pattern clearly demonstrated the transition from the near-field to far-field propagation of the beam, with the narrowest beam at the Rayleigh distance (FIG. 35B). The transducer was driven with a 5 V peak-to-peak voltage signal at 1.85 MHz. The measured de-rated peak rarefaction pressure was 14 kPa, resulting in a mechanical index (MI) of 0.01. De-rated spatial pulse peak average ($I_{SPPA}$) and spatial peak time average ($I_{SPTA}$) of 6.37 mW/cm$^2$ and 0.21 mW/cm$^2$ at 10 kHz pulse repetition were 0.0034% and 0.03% of the FDA regulatory limit, respectively (Food and Drug Administration, 2008). The transceiver board was capable of outputting up to 32 V peak-to-peak and the output pressure increased linearly with the input voltage (FIG. 35C).

Figure 36A:
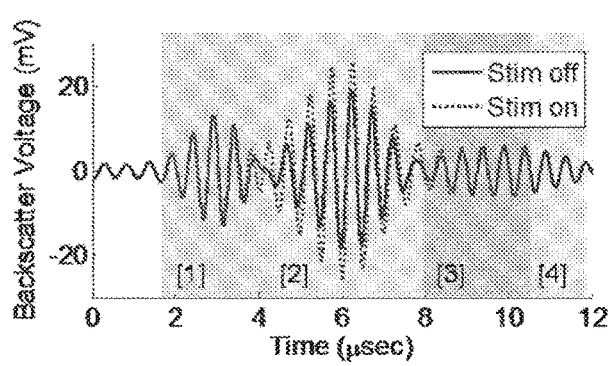
FIG. 36A (duplicate of FIG. 5E shown in different context) shows example backscatter waveform showing different regions of backscatter. The backscatter waveform is found flanked (in time) by regions which correspond to reflections arising from non-responsive regions; these correspond to reflected waveforms from other implantable device components. The measurement from the non-responsive regions (which do not encode biological data) can be used as a reference. As a result of taking this differential measurement, any movements of the entire structure relative to the external transducer during the experiment can be subtracted out.
Figure 36B:
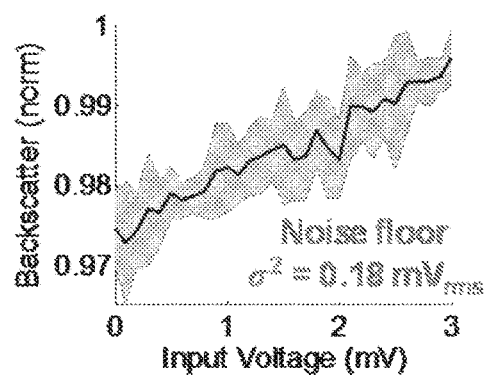
FIG. 36B is a calibration curve obtained from the custom water tank setup, which show the noise flor of 0.18 $mV_{rms}$.
Figure 36C:
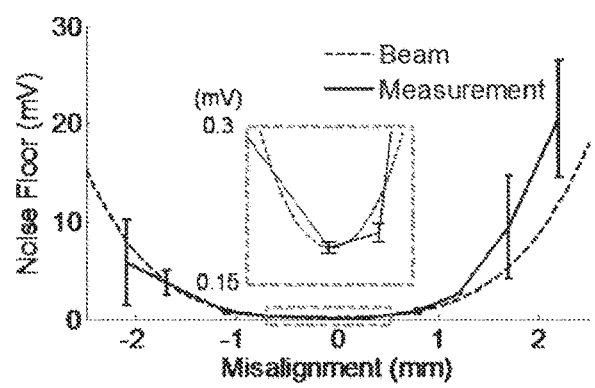
FIG. 36C shows the effect of noise floor as a function of lateral misalignment following the beam pattern power fall-off.
Figure 36D:
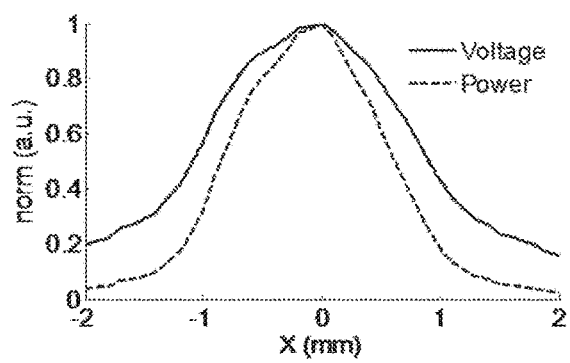
FIG. 36D shows a 1-D plot of the transducer's off-axis voltage and power drop off at y=0 at Rayleigh distance.
Figure 36E:
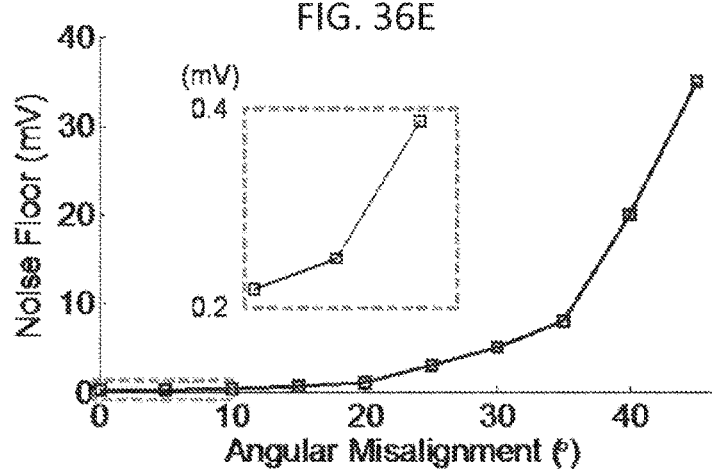
FIG. 36E shows a plot of drop in the effective noise floor as a function of angular misalignment. Angular misalignment results in a skewed beam pattern: ellipsoidal as opposed to circular. This increases the radius of focal spot (spreading energy out over a larger area); the distortion of the focal spot relaxes the constraint on misalignment.

The entire system was submerged and characterized in a custom-built water tank with manual 6 degrees-of-freedom (DOF) linear translational and rotational stages (Thorlabs Inc., Newton, N.J.). Distilled water was used as a propagation medium, which exhibits similar acoustic impedance as tissue, at 1.5 MRayls. For initial calibration of the system, a current source (2400-LV, Keithley, Cleveland, Ohio) was used to mimic extracellular signals by forcing electrical current at varying current densities through 0.127 mm thick platinum wires (773000, A-M Systems, Sequim, Wash.) immersed in the tank. The neural dust mote was submerged in the current path between the electrodes. As current was applied between the wires, a potential difference arose across the implant electrodes. This potential difference was used to mimic extracellular electrophysiological signals during tank testing. To interrogate the neural dust mote, six 540 ns pulses every 100 μs were emitted by the external transducer. These emitted pulses reflect off the neural dust mote and produce backscatter pulses back towards the external transducer. Reflected backscatter pulses were recorded by the same transceiver board. The received backscatter waveform exhibits four regions of interest; these are pulses reflecting from four distinct interfaces (FIG. 36A): 1) the water-polymer encapsulation boundary, 2) the top surface of the piezoelectric crystal, 3) the piezo-PCB boundary, and 4) the back of the PCB. As expected, the backscatter amplitude of the signals reflected from the piezoelectric crystal (second region) changed as a function of changes in potential at the recording electrodes. Reflected pulses from other interfaces did not respond to changes in potential at the recording electrodes. Importantly, pulses from the other non-responsive regions were used as a signal level reference, making the system robust to motion or heat-induced artifacts (since pulses reflected from all interfaces change with physical or thermal disturbances of the neural dust mote but only pulses from the second region change as a function of electrophysiological signals). In a water tank, the system showed a linear response to changes in recording electrode potential and a noise floor of ~0.18 mVrms (FIG. 36B). The overall dynamic range of the system is limited by the input range of the transistor and is greater than >500 mV (i.e., there is only an incremental change in the current once the transistor is fully on (input exceeds its threshold voltage) or fully off). The noise floor increased with the measured power drop-off of the beam; 0.7 mm of misalignment degraded it by a factor of two (N=5 devices, FIG. 36C). This lateral mis-alignment-induced increase in the noise floor constitutes the most significant challenge to neural recordings without a beamsteering system (that is, without the use of an external transducer array that can keep the ultrasonic beam focused on the implanted dust mote and, thus, on-axis). On axis, the implantable device converted incident acoustic power to electrical power across the load resistance of the piezo with ~25% efficiency. FIG. 36D plots the off-axis drop-off of voltage and power at one Rayleigh distance for the transducer used in this example. Likewise, FIG. 36E plots the change in effective noise floor as a function of angular misalignment.

Example 7—Digital Communication Link Between Implantable Device and Interrogator A system including an implantable device and an interrogator having a transducer array is validated with a bench-top setup mimicking an in-vivo environment. Ultrasound coupling gel serves as a tissue phantom due to its acoustic impedance which is similar to that of target biological tissues (approximately 1.5 MRayl). An implantable device with a bulk piezoelectric transducer with direct connections to the two electrodes contacting the transducer is placed in the tissue phantom, and the interrogator transducer array is coupled to the gel. Both elements are attached to precision controlled stages for accurate positioning. The transducer array is placed 14 mm away from the dust mote, which corresponds to a 18.6 μs round-trip time of flight assuming an acoustic velocity of 1,540 m/s in ultrasound coupling gel. The transducer array is excited with six 1.8 MHz, 0-32 V rectangular pulses, and the backscatter signal is digitized with 2000 samples at 17 Msps and 12-bits of resolution. For time-domain backscatter inspection, complete backscatter waveforms are filtered in real time on the device and sent to the client through a wired, serial connection. In normal operation, the complete modulation extraction algorithm is applied to the backscatter data on the device in real-time, compressing the backscatter signal to four bytes. The processed data is transmitted through BLUETOOTH® wireless technology's SSP protocol to a remote client and streamed through the GUI in real-time.

Figure 37A:
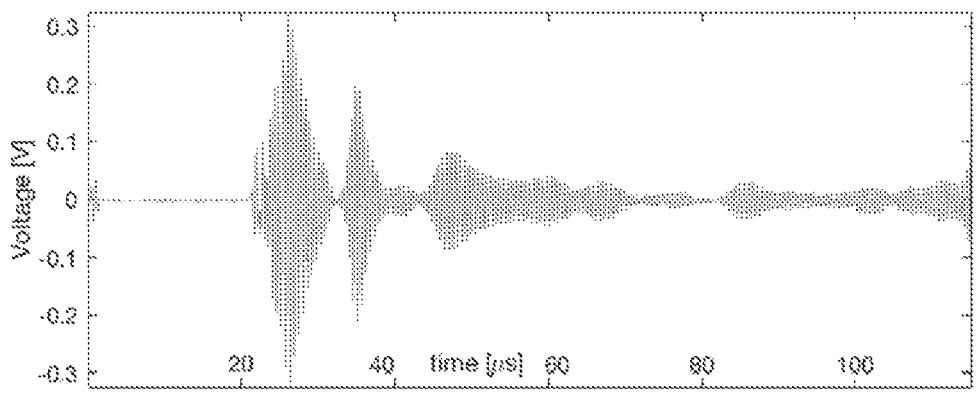
FIG. 37A shows ultrasonic backscatter from an implantable device, with the implantable device implanted inn ultrasound coupling gel used to mimic tissue. The backscatter includes a transmit feedthrough and ring-down centered at 26 microseconds, and the miniaturized ultrasonic transducer backscatter centered around 47 microseconds.
Figure 37B:
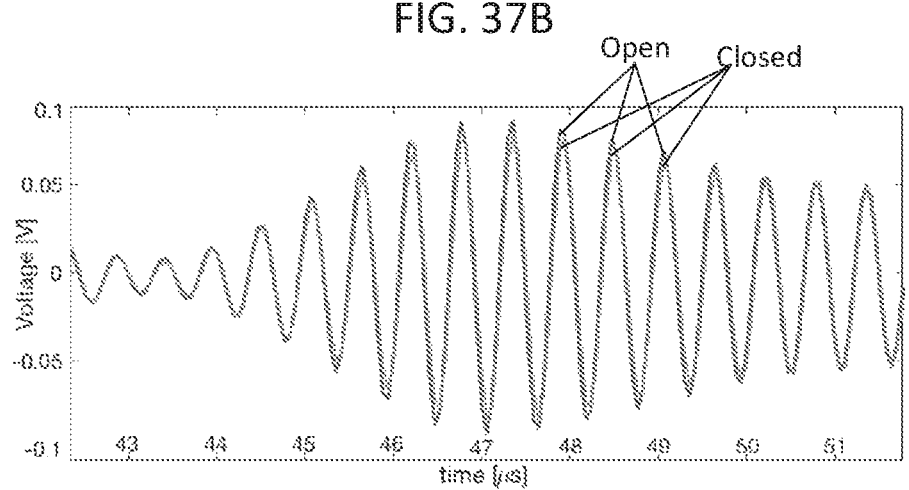
FIG. 37B shows a close-up on the backscatter region from the miniaturized ultrasonic transducer (the responsive region), which shows amplitude modulation as a result of a signal input to the implantable device.

FIG. 37A shows the filtered backscatter signals collected with the described experimental setup. Signals are collected while the dust mote piezocrystal electrodes are in the shorted and opened configurations. The change in impedance due to the switch activity results in a backscatter peak amplitude that is 11.5 mV greater in the open switch configuration, a modulation depth of 6.45%. (FIG. 37B). The long duration of the echo from the mote indicates transducer ringing despite a damping backing layer. While the under-damped transducer system response does spread out the backscatter signal in the time-domain, demodulation is successful as long as the backscatter from the implanted device is captured within the ROI.

Figure 39:
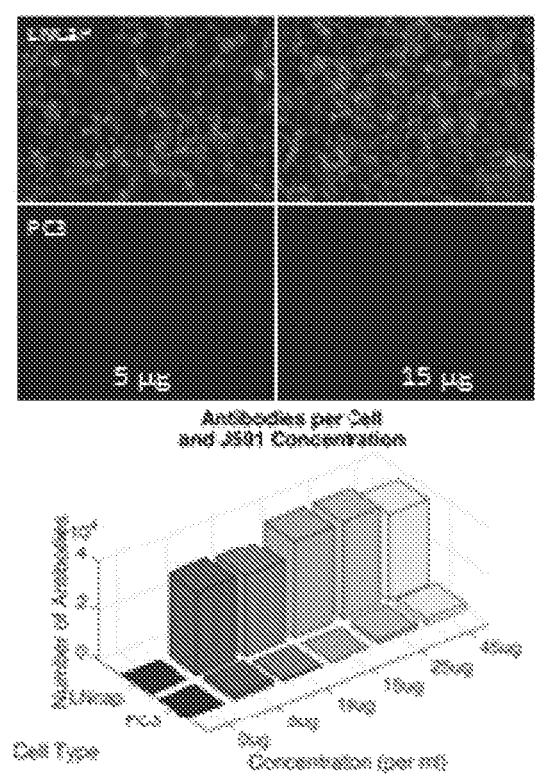
FIG. 39 shows PSMA over-expressing prostate cancer cells (LNCaPs) and non-PSMA expressing cells (PC3) stained with J591 anti-SMA antibody with increasing concentration (stained with secondary anti-human FITC) and nuclear counterstain (DAPI) LNCaPs stain strongly, while minimal background staining is seen with PC3. Quantification of antibody binding per cell shows 35,000 antibodies per cell with LNCaP and 2,000 antibodies per cell with PC3.

Using pulse-amplitude-modulated non-return to zero level coding, a backscatter sensor mote is modulated to send a predetermined 11-character ASCII message ("hello world"). The modulation of the device's acoustic impedance is achieved by shunting the piezoelectric transducer across a digitally controlled switch where a high level corresponds to the open configuration and a low level corresponds to the closed configuration. FIG. 39 shows the modulated values on the transducer and the corresponding extracted modulation values of the interrogator. The absolute value and noise margin of the extracted signal values depend on a variety of factors such as mote distance, orientation, and size; however, the extracted waveform remains representative of the modulated signal on the dust mote, varying by a linear scaling factor.

Wirelessly transmitting the extracted backscatter value of the implanted device modulated by "hello world" demonstrates the device's real time communication link with implanted devices. Interrogation of a two state backscatter system provides a robust demonstration of the system's wireless communication link with both an implantable sensor and a remote client. This wireless communication link invites developments toward closed-loop neuromodulation systems to connect the brain with external devices.

Example 7—Oncology Dust Used to Detect Prostate Cancer Recurrence

While the Oncology Dust platform can be applied to any tumor type with a targeted biologic, leveraging an ever-increasing number of cancer specific molecules, the present example demonstrates it in prostate cancer, where 50-70% of the 34,000 to 68,000 men diagnosed annually with high risk disease have recurrence within 7 years. 50% of these high-risk patients that recur within 3 years of surgery will develop, and subsequently die from, metastatic prostate cancer within 5 years. Therefore, recurrent cancer must be identified, localized and definitively treated in the short window of time before it disseminates, necessitating a new approach to cancer monitoring. Leveraging a known biomarker (prostate membrane specific antigen, PSMA) and a pre-clinically validated anti-PSMA antibody (J591]), an approach to cancer detection includes the following aspects:

(1) Label tumor cells using targeted, short-range radiolabeled biologics. Prostate cancers can be specifically bound using an anti-PSMA antibody J591. Addressing one of the key challenges in imaging microscopic disease in vivo is the detection of $10^4$-$10^5$ tumor cells amidst a large background of $10^9$-$10^{11}$ normal cells, masking the tumor signal. Beta (electron) emitting radiolabel (P32) can be used for imaging, whose range is limited by its energy. By virtue of the particle only traveling a set distance, each sensor only "sees" a small volume around it (dramatically reducing background) while a mesh or network of sensors acts in parallel to image the entire at-risk area.

(2) An implantable sensor network to localize tumor cells in vivo: To differentiate tumor (originating from a single point in space) from background (which is uniform), a sub-millimeter implantable sensor using an IC platform, comprised of two high-speed, high-sensitivity back-to-back radiation detector arrays that measure and analyze the trajectories of all incoming particles, computing and transmitting the location of the tumor focus, was implemented. Reconstructing the incoming path of each incident electron requires single particle detection. Communication of tumor location to the clinician via ultrasound eliminates the need for a bulky, time-limited biocompatible battery. Building on sub-millimeter technology, both power and data are communicated to the clinician via ultrasound.

Building on this, an implantable sensor for tumor detection may be realized through the following: (1) A Radiolabeled Antibody: In order to accurately identify small (~100,000) numbers of recurrent or residual prostate cancer cells amidst billions of normal cells, a highly specific molecular label capable of binding tumor cells in vivo is used. Labeling tumor cells using a targeted antibody conjugated to a beta-emitting antibody is an essential step in conveying the presence of a tumor cell to the sensor. Using a model system of prostate cancer, which over expresses PSMA, the humanized antibody J591 has been shown to specifically bind to prostate cancer both in vitro and in vivo.

Radiolabeling J591 conjugates: To enable identification of the tumor signal amidst the normal tissue background, the expected signal from both the tumor and the surrounding background tissue is quantified. This can be done by quantifying binding of J591 (a fully humanized anti-PSMA antibody) to two prostate cancer cells lines, in vitro: the PSMA over-expressing LNCaP, and non-PSMA expressing PC3s.

Figure 38:
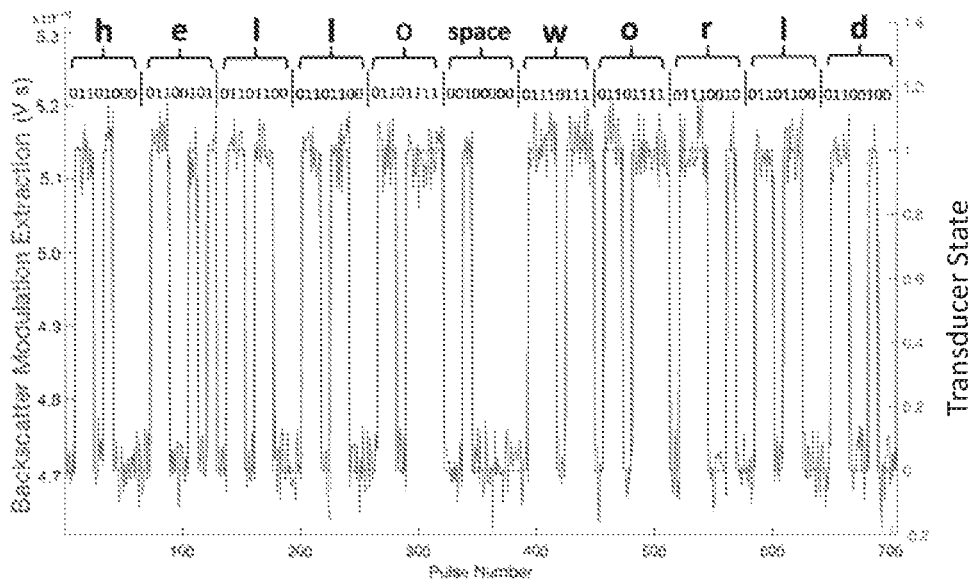
FIG. 38 shows digital data corresponding to ASCII characters 'hello world' wirelessly ready from the implantable device through pulse amplitude backscatter modulation with unipolar encoding.

FIG. 38 shows LNCaP and PC3 cells incubated with increasing concentrations of J591 (5-45 µg/ml) and anti-human-FITC (secondary). At a concentration of 5 µg/ml, binding is 35,000 antibodies/cell for LNCaP and 2,000 antibodies/cell for PC3. An alternative molecule targeting PSMA also binds prostate cancer cells in vivo, can be used. Unlike the commercially available ProstaScint antibody, whose large structure prevents efficient bio-distribution and labeling, the small molecular peptidomimetic has good biodistribution and high specificity, binding to the tumor 9 times more than the non-specific binding to normal organs.

In vivo quantification of antibody binding. To establish the binding specificity and biodistribution of each compound in vivo, a prostate animal model injected with radiolabeled anti-PSMA ligand. PSMA overexpressing 22RV1 cells and PC-3 cells are subcutaneously implanted in different locations within the same nude mouse. To determine bio-distribution of the compound, the initial radiolabel will be F18, a gamma emitter, enabling real-time whole animal imaging with PET. To establish the optimal amount of anti-PSMA agent to inject, the difference in binding between 22RV1 and PC-3 cells, quantified by SUVmax will be assessed. 1, 10, and 50 nanomoles of F18-antiPSMA agent (J591 and peptidomimetic) are injected into mice sacrificed at 24, 48, and 96 hrs (total 36 mice+2 sham), and imaged with whole animal PET/SPECT every 12 hours to quantify the bio-distribution. This data will identify the optimal timing and dose of the injection. After sacrifice, the tumors (22RV1 and PC-3) will be extracted, weighed and the radioactivity quantified, enabling determination of the number of bound molecules for each cell type.

The invention claimed is:

1. An implantable device, comprising:
an array comprising a plurality of pixels, each pixel comprising a radiation-sensitive diode configured to generate an electrical signal upon encountering radiation;

an integrated circuit configured to receive the electrical signal and digitally modulate a current based on the received electrical signal, wherein the integrated circuit comprises a digital circuit and a modulation circuit, and the digital circuit transmits a digitized signal to the modulation circuit based on the electrical signal generated by the radiation-sensitive diode; and an ultrasonic transducer configured to emit digitized ultrasonic backscatter based on the digitally modulated current encoding information relating to the encountered radiation.

2. The implantable device of claim 1, wherein the magnitude of the electrical signal is based on the energy of the encountered radiation.

3. The implantable device of claim 1, wherein the implantable device comprises two or more arrays each comprising a plurality of pixels, each pixel comprising a radiation-sensitive diode configured to generate an electrical signal upon encountering radiation.

4. The implantable device of claim 3, wherein the arrays in the plurality of arrays are stacked.

5. The implantable device of claim 3, wherein the arrays in the plurality of arrays are separated by about 1 mm or less.

6. The implantable device of claim 4, wherein the implantable device is configured to determine a directional vector for the encountered radiation.

7. The implantable device of claim 4, wherein the implantable device is configured to determine a plurality of directional vectors for the encountered radiation; and, based on the plurality of directional vectors for the encountered radiation, determine a location of origin of the encountered radiation.

8. The implantable device of claim 7, wherein the location of origin is a radiolabeled cell, a radiolabeled cluster of cells, a radiolabeled molecule, or a radiation beam.

9. The implantable device of claim 7, wherein the location of origin is a radiolabeled cancer.

10. The implantable device of claim 1, wherein each pixel within the array is assigned a unique address.

11. The implantable device of claim 1, wherein the implantable device is configured to filter radiation below a predetermined energy threshold.

12. The implantable device of claim 11, wherein radiation is filtered based on the magnitude of the electrical signal generated by the radiation sensitive diode upon encountering the radiation.

13. The implantable device of claim 11, wherein the implantable device comprises three or more arrays comprising a plurality of pixels comprising a radiation-sensitive diode, and wherein the radiation is filtered based on a changed directional vector between the three or more arrays.

14. The implantable device of claim 1, wherein the implantable device comprises a memory configured to store information related to the encountered radiation.

15. The implantable device of claim 1, wherein the implantable device comprises a clock, and wherein the information related to the encountered radiation comprises information related to the time the radiation-sensitive diode encountered the radiation.

16. The implantable device of claim 1, wherein the diode is covered by a scintillator material.

17. The implantable device of claim 1, wherein the ultrasonic transducer is configured to receive ultrasonic waves that power the implantable device.

18. A system comprising one or more implantable devices according to claim 1, and an interrogator comprising one or more ultrasonic transducers configured to transmit ultrasonic waves to the one or more implantable devices or receive ultrasonic backscatter from the one or more implantable devices.

\* \* \* \* \*